US007198915B2

(12) United States Patent
Tirrell et al.

(10) Patent No.: US 7,198,915 B2
(45) Date of Patent: *Apr. 3, 2007

(54) OVEREXPRESSION OF AMINOACYL-TRNA SYNTHETASES FOR EFFICIENT PRODUCTION OF ENGINEERED PROTEINS CONTAINING AMINO ACID ANALOGUES

(75) Inventors: David A. Tirrell, Pasadena, CA (US); Kristi Lynn Kiick, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 475 days.

This patent is subject to a terminal disclaimer.

(21) Appl. No.: 10/612,713

(22) Filed: Jul. 1, 2003

(65) Prior Publication Data

US 2004/0058415 A1   Mar. 25, 2004

Related U.S. Application Data

(63) Continuation of application No. 09/767,515, filed on Jan. 23, 2001, now Pat. No. 6,586,207.

(60) Provisional application No. 60/207,627, filed on May 26, 2000.

(51) Int. Cl.
| | |
|---|---|
| C12N 15/09 | (2006.01) |
| C12N 15/63 | (2006.01) |
| C12N 15/64 | (2006.01) |
| C12N 15/85 | (2006.01) |
| C12P 21/00 | (2006.01) |
| C12P 21/02 | (2006.01) |
| C12Q 1/68 | (2006.01) |
| C07K 2/00 | (2006.01) |

(52) U.S. Cl. .................. 435/69.1; 435/455; 435/320.1
(58) Field of Classification Search ..................... None
See application file for complete search history.

(56) References Cited

U.S. PATENT DOCUMENTS

| | | | | |
|---|---|---|---|---|
| 5,110,906 | A * | 5/1992 | Maddon et al. | 530/350 |
| 5,370,995 | A | 12/1994 | Hennecke et al. | 435/69.1 |
| 5,627,033 | A * | 5/1997 | Smith et al. | 435/6 |
| 5,879,905 | A * | 3/1999 | RajBhandary | 435/69.1 |
| 6,221,640 | B1 * | 4/2001 | Tao et al. | 435/183 |
| 6,586,207 | B2 * | 7/2003 | Tirrell et al. | 435/69.1 |

OTHER PUBLICATIONS

Dardel et al., J. Bacteriol., 1984, vol. 160, No. 3, pp. 1115-1122.*
Kiick et al. Tetrahedron, 2000, vol. 56, pp. 9487-9493.*
Bain, J.D. et al. Nature 1992, 356, 537-539. (Exhibit 1).
Berent et al., Biotech (1985) 3:208-220. (Exhibit 2).
Boles, J.O. et al Nature Struct. Biol. 1994, 1, 283-284. (Exhibit 3).
Cohen et al., 1972 Proc Acad Sci USA 69:2110-2114. (Exhibit 4).
Cornish, V.W.; Mendel, D.; Schultz, P.G. Angew. Chem. Int. Ed. Engl. 1995, 34, 621-634. (Exhibit 5).
Dardel, F.; Panvert, M.; Fayat, G. Mol. Gen. Genet. 1990, 223, 121-133. (Exhibit 6).
Duewel, H.; Daub, E.; Robinson, R.; Honek, J.F. Biochemistry 1997, 36, 3404-3416. (Exhibit 7).
Graham et al., 1973 Virol 52:456-467. (Exhibit 8).
Hendrickson, W.A.; Horton, J.R.; Lemaster, D.M. EMBO J. 1990, 9, 1665-1672. (Exhibit 9).
Hirel, P.H.; Schmitter, J.M.; Dessen, P.; Fayat, G.; Blanquet, S. Proc. Natl Acad. Sci. USA 1989, 86, 8247-8251. (Exhibit 10).
Horlacher, J. et al. Proc. Natl. Acad. Sci. USA 1995, 92, 6329-6333. (Exhibit 11).
Ibba, M.; Soll, D. Science 1999, 286, 1893-1897. (Exhibit 12).
Kim, H.Y.; Ghosh, G.; Schulman, L.H.; Brunie, S. Jakubowski, H. Proc. Natl. Acad. Sci. USA 1993, 90, 11553-11557. (Exhibit 13).
Kool, E.T. Biopolymers 1998, 48, 3-17. (Exhibit 14).
Krejchi, M.T.; Atkins, E.D.T.; Waddon, A.J.; Fournier, M.J.; Mason, T.L.; Tirrell, D.A. Science 1994. 265, 1427-1432. (Exhibit 15).
Liu, D.R.; Maghery, T.J.; Pastrnak, M.; Schultz, P.G. Proc. Natl. Acad. Sci. USA, 1997, 94, 10092-10097. (Exhibit 16).
Liu, D.R.; Schultz, P.G. Proc. Natl. Acad. Sci. 1999, 96, 4780-4785. (Exhibit 17).
Luo, D., J. Leautey, M. Grunberg-Manago, H. Putzer, J. Bacteriol. 1997, 179, 2472-2478. (Exhibit 18).
Lutz, M.J.; Held, H.A.; Hottiger, M.; Hubscher, U.; Benner, S.A. Nuc. Acids Res. 1996, 24, 1308-1313. (Exhibit 19).
Mahal, L. K., K. J. Yarema, C. R. Bertozzi, Science 1997, 276, 1125-1128. (Exhibit 20).
Matray, T.J.; Kool, E.T. Nature 1999, 309, 704-708. (Exhibit 21).
Morales, J.C.; Kool, E.T. Nature Struct. Biol. 1998, 5, 950-954. (Exhibit 22).
Noren, C.J.; Anthony-Cahill, S.J.; Griffith, M.C.; Schultz, P.G. Science 1989, 244, 182-188. (Exhibit 23).
Nowak, M.W. et al. Science, 1995, 268, 439-442. (Exhibit 24).
Petka, W.A.; Hardin, J.L.; McGrath, K.P.; Tirrell, D.A. Science 1998, 281, 389-392. (Exhibit 25).
Piccirilli, J.A.; Krauch, T.; Moroney, S.E.; Benner, S.A. Nature, 1990, 343, 33-37. (Exhibit 26).
Sanger, F., S. Nicklen, A. R. Coulson, Proc. Natl. Acad. Sci. USA 1977, 74, 5463-5467. (Exhibit 27).
Saxon, E. and Bertozzi, C.R. Science 2000, 287, 2007-2010. (Exhibit 28).
Sherman, J. M., M. J. Rogers, D. Soll, Nuc. Acids. Res. 1992, 20, 2847-2852.(Exhibit 29).
Southern, J Mol Biol (1975) 98:503-517. (Exhibit 30).
Swanson, R., P. Hoben, M. Sumner-Smith, H. Uemura, L. Watson, D. Soll, Science 1988, 242, 1548-1551. (Exhibit 31).
Wei, Y.; Hendrickson, W.A.; Crouch, R.J.; Satow, Y. Science 1990, 249, 1398-1405. (Exhibit 32).

(Continued)

Primary Examiner—David Guzo
(74) Attorney, Agent, or Firm—Seed IP Law Group PLLC

(57) ABSTRACT

Methods for producing modified polypeptides containing amino acid analogues are disclosed, as well as compositions comprising purified dihydrofolate reductase polypeptides, produced by the methods of the invention. In certain aspects, methionine residues of the compositions are replaced with homoallyglycine, homoproparglycine, norvaline, norleucine, cis-crotyiglycine, trans-crotylglycine, 2-aminoheptanoic acid, 2-butynyiglycine and allyglycine.

11 Claims, 28 Drawing Sheets

OTHER PUBLICATIONS

Wigler et al., 1979 *Proc Natl Acad Sci USA* 76:1373-76. van Hest, J.C.M.; Tirrell, D.A. *FEBS Lett.* 1998, 428, 68-70. (Exhibit 33).
Zhang, G, Yu, S.M.; Conticello, V.; Kayser, C.; Fournier, M.J.; Mason, T.L.; Tirrell, D.A. *Nature* 1997, 389, 187-190. (Exhibit 34).
Bain, J., et al., "Biosynthetic Site-specific Incorporation of a Non-natural Amino Acid into a Polypeptide," *J. Am. Chem. Soc.*, *111*:8013-8014, 1989.
Barton, D., et al., "Synthesis of Novel a-Amino-Acids and Derivatives Using Radical Chemisrty: Synthesis of L- and D-a-Amino-Adipic Acids, L-a-aminopimelic Acid and Appropriate Unsaturated Derivatives," *tetrahedron*, 43:4297-4308, 1987.
Bradley, D., et al., tRNA$_2^{Gln}$Su$^+$2 Mutants that Increase Amber Suppression, *J Bacteriol.*, *145*(2):704-12, Feb. 1981.
Brick, P., et al., "Structure of Tyrosyl-tRNA Synthetase Refined at 2 3 Å Resolution. Interaction of the Enzyme with the Tyrosyl Adenylate Intermediate," *J. Mol. Biol.*, *208*(1):83-98, 1989.
Budisa, N., et al., "Bioincorporation of Telluromethionine into Proteins:a Promising New Approach for X-ray Structure Analysis of Proteins," *J Mol Biol.*, *270*(4):616-23, Jul. 25, 1997.
Budisa, N., et al., "High-level Biosynthetic Substitution of Methionine in Proteins by its Analogs 2-aminohexanoic Acid, Selenomethionine, Telluromethionine and Ethionine in Escherichia coli," *Eur. J. Biochem*, 230(2):788-796, 1995.
Budisa, N., et al., "Residue-specific Bioincorporation of Non-natural, Biologically Active Amino Acids into Proteins as Possible Drug Carriers: Structure and Stability of the Perthiaproline Mutant of Annexin V," *Proc Natl Acad Sci U S A*, 95(2):455-9, Jan. 20, 1998.
Budisa, N., et al., "Toward the Experimental Codon Reassignment in Vivo: Protein Building with an Expanded Amino Acid Repertoire," *FASEB J.*, *13*(1):41-51, Jan 1999.
Christie, B., et al., "Synthesis of Optically Pure Pipecolates from L-Asparagine. Application to the Total Synthesis of (+)-Apovincamine through Amino Acid Decarbonylation and Iminium Ion Cyclization," *J. Org. Chem.*, *50*:1239-1246, 1985.
Cornish, V., et al., "Site-specific Protein Modification Using a Ketone Handle," *J. Am. Chem. Soc.*, 118:8150-8151, 1996.
Doctor, B., et al., "Species Specificity Of Amino Acid Acceptor Ribonucleic Acid And Aminoacyl Soluble Ribonucleic Acid Synthetases," *J Biol Chem.*, 238:677-81, Nov. 1963.
Döring, V., et al., "Enlarging the Amino Acid set of Escherichia coli by Infiltration of the Valine Coding Pathway," *Science*, *292*(5516):501-4, Apr. 20, 2001.
Dougherty, D., "Unnatural Amino Acids as Probes of Protein Structure and Function," *Curr Opin Chem Biol.*, *4*(6):645-52, Dec. 2000.
Ellman, J., et al., "Biosynthetic Method for Introducing Unnatural Amino Acids Site-Specifically Into Proteins," *Methods Enzymol.*, *202*:301-36, 1991.
Ellman, J., et al., "Site-specific Iincorporation of Novel Backbone Structures into Proteins," *Science*, *255*(5041):197-200, Jan. 10, 1992.
England, P., et al., "Backbone Mutations in Transmembrane Domains of a Ligand-gated Ion Channel: Implications for the Mechanism of Gating," *Cell*, *96*(1):89-98, Jan. 8, 1999.
Fechter, P., et al., "Major Tyrosine Identity Determinants in Methanococcus Jannaschii and Saccharomyces cerevisiae tRNA(Tyr) are Conserved but Expressed Differently," *Eur J Biochem.*, *268*(3):761-7, Feb. 2001.
Francisco, J., et al., "Production and Fluorescence-activated Cell Sorting of Escherichia coli Expressing a Functional Antibody Fragment on the External Surface," *Proc Natl Acad Sci U S A.*, *90*(22):10444-8, Nov. 15, 1993.
Friedman, O., et al., "Synthesis of Derivatives of Glutamine as Model Substrates for Anti-Tumor Agents," *J. Am. Chem. Soc.*, *81*:3750-3752, 1959.
Furter, R., "Expansion of the Genetic Code: Site-directed p-fluoro-phenylalanine Incorporation in Escherichia coli.," *Protein Sci.*, 7(2):419-26, Feb. 1998.

Gabriel, K., et al., "A Set of Plasmids Constitutively Producing Different RNA levels in Escherichia coli," *J Mol Biol.*, *290*(2):385-9, Jul. 9, 1999.
Gallivan, J., et al., "Site-specific Incorporation of Biotinylated Amino Acids to Identify Surface-exposed Residues in Integral Membrane Proteins," *Chem Biol.*, *4*(10):739-49, Oct. 1997.
Gay, G., et al., "Modification of the Amino Acid Specificity of Tyrosyl-tRNA Synthetase by Protein Engineering," *FEBS Letters*, *318*:167-171, 1993.
Giegé, R., et al., "Aspartate Identity of Transfer RNAs," *Biochimie* *78*(7):605-23, 1996.
Giegé, R., et al., "Universal Rules and Idiosyncratic Features in tRNA Identity," *Nucleic Acids Res.*, *26*(22):5017-35, Nov. 15, 1998.
Guckian, K., "Highly Precise Shape Mimicry by a Difluoro-toluene Deoxynucleoside, a Replication-Competent Substitute for Thymidine," *Angew Chem. Int. Ed. Engl.* 36(24):2825-2828, 1997.
Hamano-Takaku, F., et al., "A Mutant Escherichia coli Tyrosyl-tRNA Synthetase Utilizes the Unnatural Amino Acid Azatyrosine more Efficiently than Tyrosine," *J Biol Chem.*, *275*(51):40324-8, Dec. 22, 2000.
Hartley, R., "Barnase and Barstar. Expression of its Cloned Inhibitor Permits Expression of a Cloned Ribonuclease," *J Mol Biol.*, *202*(4):913-5, Aug. 20, 1988.
Hohsaka, T., et al., "Efficient Incorporation of Nonnatural Amino Acids with Large Aromatic Groups into Streptavidin in In Vitro Protein Synthesizing Systems," *J. Am. Chem. Soc.*, *121*:34, 1999.
Ibba, M., et al., "Relaxing the Substrate Specificity of an Aminoacyl-tRNA Synthetase Allows in vitro and in vivo Synthesis of Proteins Containing Unnatural Amino Acids," *FEBS Lett.*, *364*(3):272-5, May 15, 1995.
Ibba, M., et al., "Substrate Specificity is determined by Amino acid Binding Pocket Size in Escherichia coli Phenylalanyl-tRNA Synthetase," *Biochemistry*, *33*(23):7107-12, Jun. 14, 1994.
Ibba, M., "Strategies for in vitro and in vivo Translation with Non-natural Amino Acids," *Biotechnol Genet Eng Rev.* 13:197-216, Dec. 1995.
Jakubowski, H., et al., "Editing of Errors in Selection of Amino Acids for Protein Synthesis.," *Microbiol Rev.*, *56*(3):412-29, Sep. 1992.
Jeruzalmi, D., et al., "Structure of T7 RNA Polymerase Complexed to the Rranscriptional Inhibitor T7 Lysozyme," *EMBO J.*, *17*(14):4101-13, Jul. 15, 1998.
Kiick, K., et al.,"Protein Engineering by in Vivio Incorporation of Non-Natural Amino Acids: Control of Incorporation of Methionine Analogues by Methionyl-tRNA Synthetase," *Tetrahedron*, 56:9487-9493, 2000.
King, F., et al., "A New Synthesis of Glutamine and of γDipeptides of Glutamic Acid from Phthalylated Intermediates," *J. Chem. Soc.*, 4:3315-3319, 1949.
Kleeman, T., et al., "Human Tyrosyl-tRNA Synthetase Shares Amino Acid Sequence Homology with a Putative Cytokine," *J Biol Chem.*, 272(22):14420-5, May 30, 1997.
Kleina, L., et al., "Construction of Escherichia coli Amber Suppressor tRNA Genes. II. Synthesis of Additional tRNA Genes and Improvement of Suppressor Efficiency," *J Mol Biol.*, *213*(4):705-17, Jun. 20, 1990.
Kool, E., "Synthetically Modified DNAs as Substrates for Polymerases," *Curr Opin Chem Biol.*, *4*(6):602-8, Dec. 2000.
Koskinen, et al., Synthesis of 4-Substituted Prolines for Conformationally Constrained Amino Acid Analogues,: *J. Org. Chem.* 54:1859-1866, 1989.
Kowal, A., et al., "Exploiting Unassigned Codons in Micrococcus Luteus for tRNA-based Amino Acid Mutagenesis," *Nucleic Acids Res.*, *25*(22):4685-9, Nov.15, 1997.
Kowal, A., et al., "Twenty-first Aminoacyl-tRNA Synthetase-suppressor tRNA Pairs for Possible Use in Site-specific Incorporation of Amino Acid Analogues into Proteins in Eukaryotes and in Eubacteria," *Proc Natl Acad U S A.*, *98*(5):2268-73, Feb. 27, 2001.
Lee, J-Y., et al., "Novel Biological Process for L-DOPA Production from L-Tyrosine by p-hydroxyphenylacetate 3-hydroxylase," *Biotechnology letters*, *20*(5):479-482, May 1998.

Liu, D. et al., "Characterization of an 'orthogonal' Suppressor tRNA Derived from E. coli tRNA$_2^{Gln}$," *Chem Biol.*, *4*(9):685-91, Sep. 1997.

Lorinez, M., et al., "Enzyme-generated Intracellular Fluorescence for Single-cell Reporter Gene Analysis Utilizing Escherichia Coli Beta-glucuronidase," *Cytometry*, *24*(4):321-9, Aug. 1, 1996.

Lu, T., et al., "Probing Ion Permeation and Gating in a K⁺Channel with Backbone Mutations in the Selectivity Filter," *Nat Neurosci.*, *4*(3):239-46, Mar. 2001.

Ma, C., et al., "In Vitro Protein Engineering Using Synthetic tRNA$^{Ala}$ with Different Anticodons," *Biochemistry*, *32*(31):7939-45, Aug. 10, 1993.

Matsoukas, J., et al., "Differences in Backbone Structure Between Angiotensin II Agonists and Type I Antagonists," *J Med Chem.*, *38*(23):4660-9, Nov. 10, 1995.

McMinn, D., et al., "Efforts Toward Expansion of the Genetic Alphabet: DNA Polymerase Recognition of a Highly Stable, Self-Pairing Hydrophobic Base," *J. Am. Chem. Soc.*, *121*:11585-11586, 1999.

Meggers, E., et al., "A Novel Copper-Mediated DNA Base Pair," *J. Am. Chem. Soc.*, *122*:10714-15, 2000.

Mendel, D., et al., "Site-directed Mutagenesis with an Expanded Genetic Code," *Annu Rev Biophys Biomol Struct.*, *24*:435-62, 1995.

Miller, J., et al., "Flash Decaging of Tyrosine Sidechains in an Ion Channel," *Neuron*, *20*(4):619-24, Apr. 1998.

Minks, C., et al., "Noninvasive Tracing of Recombinant Proteins with Fluorophenylalanine-fingers," *Anal Biochem.*, *284*(1):29-34, Aug. 15, 2000.

Moore, B., et al., "Quadruplet Codons: Implications for Code Expansion and the Specification of Translation Step Size," *J Mol Biol.*, *298*(2):195-209, Apr. 28, 2000.

Nickitenko, A., et al., 2 Å Resolution Structure of DppA, a Periplasmic Dipeptide Transport/Chemosensory Receptor, *Biochemistry*, *34*(51):16585-95, Dec. 26, 1995.

Nilsson, B., et al., "A Synthetic IgG-binding Domain Based on Staphylococcal Protein A," *Protein Eng.*, *1*(2):107-13, Feb-Mar 1987.

O'Mahony, D., et al., "Glycine tRNA Mutants with Normal Anticodon Loop Size Cause-1 Frameshifting," *Proc Natl Acad Sci U S A.*, *86*(20):7979-83, Oct. 1989.

Ogawa, A., et al., "Efforts Toward the Expansion of the Genetic Alphabet: Information Storage and Replication with Unnatural Hydrophobic Base Pairs," *J. Am. Chem. Soc. 122*:3274-3287, 2000.

Ogawa, A., et al., "Rational Design of an Unnatural Base Pair with Increased Kinetic Selectivity", *J. Am. Chem. Soc.*, *122*:8803-8804, 2000.

Ohno, S., et al., "Co-expression of Yeast Amber Suppressor tRNA$^{Tyr}$ and Tyrosyl-tRNA Synthetase in Escherichia coli: Possibilty to Expand the Genetic Code," *J Biochem (Tokyo). 124*(6):1065-8, Dec. 1, 1998.

Pastmak, M., et al., "A New Orthogonal Supressor tRNA/aminoacyl-tRNA Synthetase Pair for Evolving an Organism with an Expanded Genetic Code," *Helv. Chim. Acta, 83*:2277-2286, 2000.

Pastmak, M., et al., "Phage Selection for Site-specific Incorporation of Unnatural Amino Acids into Proteins In Vivo," *Bioorg Med Chem.*, *9*(9):2373-9, 2001.

Saks, M., et al., "An Engineered Tetrahymena tRNA$^{Gln}$ for in Vivo Incorporation of Unnatural Amino Acids into Proteins by Nonsense Suppression," *J Biol Chem.*, *271*(38):23169-75, Sep. 20, 1996.

Santoro, S., et al., "An Efficient System for the Evolution of Aminoacyl-tRNA Synthetase Specificity," *Nat. Biotechnol.*, *20*(10):1044-8, Oct. 20, 2000.

Sayers, J., et al., "5'-3' Exonucleases in Phosphorothioate-based Oligonucleotide-directed Mutagenesis," *Nucleic Acids Res.*, *16*(3):791-802, Feb. 11, 1988.

Shao, J., et al., "Unprotected Peptides as Building Blocks for the Synthesis of Peptide Dendrimers with Oxime, Hydrazone, and Thiazolidine Linkages," *J. Am. Chem. Soc.*, *117*(14):3893-3899, 1995.

Sharma, N., et al., "Efficient Introduction of Aryl Bromide Functionality into Proteins in Vivo," *FEBS Lett.*, *467*(1):37-40, Feb.4, 2000.

Sieber, V., et al., "Libraries of Hybrid Proteins from Distantly Related Sequences," *Nat Biotechnol.*, *19*(5):456-60, May 2001.

Sprinzl, M., et al., "Complication of tRNA Sequences and Sequences of tRNA Genes," *Nucleic Acids Res.*, *26*(1):148-53, Jan. 1, 1998.

Steer, B., et al., "Major Anticodon-binding Region Missing from an Archaebacterial tRNA Synthetase," *J Biol Chem.*, *274*(50):35601-6, Dec. 10, 1999.

Subasinghe, N., et al., "Quisqualic Acid Analogues: Synthesis of β-heterocyclic 2-aminopropanoic Acid Derivatives and their Activity at a Novel Quisqualate-sensitized Site," *J Med Chem.*, *35*(24):4602-7, Nov. 27, 1992.

Sussman, J., et al., "Crystal Structure of Yeast Phenylalanine Transfer RNA. I. Crystallographic Refinement," *J Mol Biol.*, *123*(4):607-30, Aug. 5, 1978.

Switzer, C., et al., "Enzymatic Incorporation of a New Base Pair into DNA and RNA,." *J. Am. Chem. Soc.*, *111*:8322-8323, 1989.

Tae, E., et al., "Efforts Toward Expansion of the Genetic Alphabet: Replication of DNA with Three Base Pairs," *J Am Chem Soc.*, *123*(30):7439-40, Aug. 1, 2001.

Tang, Y., et al., "Fluorinated Coiled-Coil Proteins Prepared In Vivo Display Enhanced Thermal and Chemical Stability," *Angew Chem Int Ed Engl.*, *40*(8):1494-1496, Apr. 17, 2001.

Turcatti, G., et al., "Probing the Structure and Function of the Tachykinin Neurokinin-2 Receptor through Biosynthetic Incorporation of Fluorescent Amino Acids at Specific Sites," *J Biol Chem.*, *271*(33):19991-8, Aug. 16, 1996.

Van Hest, J., et al., "Efficient Incorporation of Unsaturated Methionine Analogues into Proteins in Vivo," *J. Am. Chem. Soc.*, *122*:1282-1288, 2000.

Van Hest, J., et al., "Efficient Introduction of Alkene Functionally into Proteins in vivo," *FEBS Lett.*, *428*(1-2):68-70, May 22, 1998.

Wakasugi, K., et al., "Genetic Code in Evolution: Switching Species-specific Aminoacylation with a Peptide Transplant," *EMBO J.*, *17*(1):297-305, Jan. 2, 1998.

Wang, L., et al., "A New Functional Suppressor tRNA/aminoacyl-tRNA Synthetase Pair for the in Vivo Incorporation of Unnatural Amino Acids into Proteins," *J. Am. Chem. Soc.*, *122*:5010-5011, 2000.

Wang, L., et al., "A General Approach for the Generation of Orthogonal tRNAs," *Chem Biol.*, *8*(9):883-90, Sep. 2001.

Wang, L., et al., "Expanding the Genetic code of Escherichia coli," *Science*, *292*(5516):498-500, Apr. 20, 2001.

Wang, L., et al., "Expanding the genetic code," *Chem Commun (Camb).*, (1):1-11, Jan. 7, 2002.

Whelihan, E., et al., "Rescuing an Essential Enzyme-RNA Complex with a Non-essential Appended Domain," *EMBO J.*, *16*(10):2968-74, May 15, 1997.

Yarus, M., "Translational Efficiency of Transfer RNA's: Uses of an Extended Anticodon," *Science*, *218*(4573):646-52, Nov. 12, 1982.

Zlokarnik, G., et al., "Quantitation of Transcription and Clonal Selection of Single Living Cells with Beta-lactamase as Reporter," *Science*, *279*(5347):84-8, Jan. 2, 1998.

* cited by examiner

1. Methionine
2. Homoallylglycine
3. Homopropargylglycine
4. Cis-crotylglycine
5. Trans-crotylglycine
6. 6,6,6-trifluoro-2-amino hexanoic acid
7. 2-amino heptanoic acid
8. Norvaline
9. Norleucine
10. o-allylserine
11. 2-butynylglycine
12. Allylglycine
13. Propargylglycine

| Analogue (Side chain shown) | | $k_{cat}/K_m$ ($s^{-1} \mu M^{-1}$) | Relative Value | Incorporated by conventional host? |
|---|---|---|---|---|
| Met | (side chain) | $5.47 \times 10^{-1}$ | 1 | Y |
| Aha | (side chain) | $1.4 \times 10^{-3}$ | 1/390 | Y |
| Hpg | (side chain) | $1.08 \times 10^{-3}$ | 1/500 | Y |
| Norl | (side chain) | $5.22 \times 10^{-4}$ | 1/1050 | Y |
| Hag | (side chain) | $2.96 \times 10^{-4}$ | 1/1850 | Y |
| Tcg | (side chain) | $1.16 \times 10^{-4}$ | 1/4700 | N |
| 2bg | (side chain) | $3.9 \times 10^{-5}$ | 1/13825 | N |
| Norv | (side chain) | $1.2 \times 10^{-5}$ | 1/46100 | N |
| Ccg | (side chain) | $3.2 \times 10^{-6}$ | 1/171000 | N |
| Ag | (side chain) | $1.2 \times 10^{-6}$ | 1/456000 | N |

FIG. 10

| Analogue | $K_m$ (μM) | $k_{cat}$ (s$^{-1}$) | $k_{cat}/K_m$ (s$^{-1}$μM$^{-1}$) | Protein Yield, mg/L |
|---|---|---|---|---|
| 1 | 24.3 ± 2 | 13.3 ± 0.2 | 5.47x10$^{-1}$ | 35 |
| 3 | 2415 ± 170 | 2.60 ± 0.3 | 1.08x10$^{-3}$ | 35 |
| 9 | 4120 ± 900 | 2.15 ± 0.6 | 5.22x10$^{-4}$ | 20 |
| 2 | 4555 ± 200 | 1.35 ± 0.1 | 2.96x10$^{-4}$ | 10 |
| 5 | 15,675 ± 250 | 1.82 ± 0.6 | 1.16x10$^{-4}$ | 0 |

FIG. 15

| | | | | | |
|---|---|---|---|---|---|
| CTCGAGAAAT | CATAAAAAAT | TTATTTGCTT | TGTGAGCCGA | TAACAATTAT | AATAGATTCA | 60
| ATTGTGAGCG | GATAACAATT | TCACACAGAA | TTCATTAAAG | AGGAGAAATT | AACTATGAGA | 120
| GGATCGCATC | ACCATCACCA | TCACGGATCC | GGCATCATGG | TTCGACCATT | GAACTCGATC | 180
| GTCGCCGTGT | CCCAAAATAT | GGGGATTGGC | AAGAACGGAG | ACCTACCCTG | GCCTCCGCTC | 240
| AGGAACGAGT | TCAAGTACTT | CCAAAGAATG | ACCACAACCT | CTTCAGTGAA | AGGTAAACAG | 300
| AATCTGGTGA | TTATGGGTAG | GAAAACCTGG | TTCTCCATTC | CTGAGAAGAA | TCGACCTTTA | 360
| AAGGACAGAA | TTAATATAGT | TCTCAGTAGA | GAACTCAAAG | AACCACCACG | AGGAGCTCAT | 420
| TTTCTTGCCA | AAAGTTTGGA | TGATGCCTTA | AGACTTATTG | AACAACCGGA | ATTGGCAAGT | 480
| AAAGTAGACA | TGGTTTGGAT | AGTCGGAGGC | AGTTCTGTTT | ACCAGGAAGC | CATGAATCAA | 540
| CCAGGCCACC | TTAGACTCTT | TGTGACAAGG | AAATATAAA | CTTCTCCCAG | TGACACGTTT | 600
| TTCCCAGAAA | TTGATTTGGG | GAAATATAAA | AGTTTGAAG | AATACCCAGG | CGTCCTCTCT | 660
| GAGGTCCAGG | AGGAAAAAGG | CATCAAGTAT | TCTACGAGAA | TCTACAGCAG | GAAAGGTTGG | 720
| AAGATCTTAA | GCTTAATTAG | CTGAGCTTGG | ACTCCTGTTG | ATAGATCCAG | TAATGACCTC | 780
| AGAACTTCAT | CTGGATTTGT | TCAGAACGCT | CGGTTGCCGC | CGGGCGTTT | TTATTGGTGA | 840
| GAATCCAAGC | TAGCTCTAGA | GACGTCCGGC | CGGAGCTCCA | CCCCTTTTCA | GGCCGGTGGC | 900
| GAGTCACTTA | CTTAACATTT | TCCCATTTGG | TACTATCTAA | AAAATTCTGG | CTATTAAGAA | 960
| GTAATGCCTA | CTATGACTCA | AGTCGCGAAG | AAAATTCTGG | TGACGTGCGC | ACTGCCGTAC | 1020
| GCTAACGGCT | CAATCCACCT | CGGCCATATG | CTGGAGCACA | TCCAGGCTGA | TGTCTGGGTC | 1080
| CGTTACCAGC | GAATGCGCGG | CCACGAGGTC | AACTTCATCT | GCGCCGACGA | TGCCCACGGT | 1140
| ACACCGATCA | TGCTGAAAGC | GGTATCACCC | GGTATCACCC | CGGAGCAGAT | GATTGGCGAA | 1200
| ATGAGTCAGG | AGCATCAGAC | CGAAGAGAA | TGATTTCGCA | GGCTTTAACA | TCAGCTATGA | CAACTATCAC | 1260
| TCGACGCACA | GCGAAGAGAA | CCGCCAGTTG | TCAGCAGTTG | TCAGCAGTTG | CCTGAAAGAA | 1320
| AACGGTTTTA | TTAAAAACCG | AGGCACCTGC | CAGCACCTGC | AGCACCTGC | AGGCATGTTC | 1380
| CTGCCGGACC | GTTTGTGAA | CGGCACCTGC | CAGCACCTGC | AGCACCTGC | AGGCATGTTC | 1440
| GATAACTGCG | AAGTCTGCGG | CGCGACCTAC | AGCCCGACTG | AACCCGACTG | AATCGATCGA | GCCGAAATCG | 1500
| GTGGTTTCTG | GCGCTACGCC | GATTCTGAAC | GTAATGCGGT | ACTTCTTCTT | TGATCTGCCC | 1560

FIG. 19-1

| | | | | |
|---|---|---|---|---|
| TCTTTCAGCG | AAATGTTGCA | GGCATGGACC | CGCAGCGGTG | CGTTGCAGGA | GCAGGTGGCA | 1620 |
| AATAAAATGC | AGGAGTGGTT | TGAATCTGGC | CTGCAACAGT | GGGATATCTC | CCGCGACGCC | 1680 |
| CCTTACTTCG | GTTTTGAAAT | TCCGAACGCG | CCGGGCAAAT | ATTTCTACGT | CTGGCTGGAC | 1740 |
| GCACCGATTG | GCTACATGGG | TTCTTTCAAG | AATCTGTGCG | ACAAGCGCGG | CGACAGCGTA | 1800 |
| AGCTTCGATG | AATACTGGAA | GAAAGACTCC | ACCGCCGAGC | TGTACCACTT | CATCGGTAAA | 1860 |
| GATATTGTTT | ACTTCCACAG | CCTGTTCTGG | CCTGCCATGC | TGGAAGGCAG | CAACTTCCGC | 1920 |
| AAGCCGTCCA | ACCTGTTTGT | TCATGGCTAT | GTGACGGTGA | ACGGCGCAAA | GATGTCCAAG | 1980 |
| TCTCGCGGCA | CCTTTATTAA | AGCCAGCACC | TGGCTGAATC | ATTTTGACGC | AGACAGCCTG | 2040 |
| CGTTACTACT | ACACTGCGAA | ACTCTCTTCG | CGCATTGATG | ATATCGATCT | CAACCTGGAA | 2100 |
| GATTTCGTTC | AGCGTGTGAA | TGCCGATATC | GTTAACAAAG | TGGTTAACCT | GGCCTCCCGT | 2160 |
| AATGCGGGCT | TTATCAACAA | GCGTTTTGAC | GGCGTGCTGG | CAAGCGAACT | GGCTGACCCG | 2220 |
| CAGTTGTACA | AAACCTTCAC | TGATGCCGCT | GAAGTGATTG | GTGAAGCGTG | GGAAAGCCGT | 2280 |
| GAATTTGGTA | AAGCCGTGCG | CGAAATCATG | GCGCTGGCTG | ATCTGGCTAA | CCGCTATGTC | 2340 |
| GATGAACAGG | CTCCGGTGGT | GGTGGCGAAA | CAGGAAGGCC | GCGATGCCGA | CCTGCAGGCA | 2400 |
| ATTGCTCAA | CCTGTTCCGC | CCTGTCGATGA | GTGCTGATGA | CTTACCTGAA | GCCGGTACTG | 2460 |
| CCGAAACTGA | TGGGCATCAA | AGAAGCATTC | CTCAATACGG | AACTGACCTG | GGATGGTATC | 2520 |
| CAGCAACCGC | CCGAGCGTGC | CAAAGTGAAT | CCGTTCAAGG | CGCTGTATAA | CCGCATCGAT | 2580 |
| ATGAGGCAGG | TGCTGGGCCA | GGTGGAAGCT | TCTAAATGAG | AAGTAAAAGC | CGCTGCCGCG | 2640 |
| CCGGTAACTG | TTGAAGCACT | AGATGATCCG | ATTCAGGAAA | CCATCACCTT | TGACGACTTC | 2700 |
| GCTAAAGTTG | GCCCGCTGGC | GCCCGCGCGT | GAAAACGCAG | AGTTTGTTGA | AGTTCTGAC | 2760 |
| AAACTGCTGC | ACCTGCGCGT | ACCTGCGCGT | GGATCTCGGC | GGTGAAAAAC | CTCCGGTATT | 2820 |
| CGTTCTGCTT | ACCCGGATCC | GCCTGACGCT | GCAGGCACTG | ATTGGTCGTC | GGTGGCTAAC | 2880 |
| CTGGCACCAC | GTAAAATGCG | CTTCGGTATC | TCTCGGTATC | TGGTGATGGC | TGCCGGTCCT | 2940 |
| GGCGGGAAAG | ATATTTTCCT | GCTAAGCGCG | GATGCATCGA | CAGCCTTTTG | TCATCAGGTG | 3000 |
| AAATAATCCC | CCTTCAAGGC | GCTGCATGCT | CTAAGGC | CTTTATAAAT | TCCTAAAGTT | 3060 |
| GTTTTCTTGC | GATTTTGTCT | CTCTCTAACC | CGCATAAATA | CTGGTAGCAT | CTGCATTCAA | 3120 |

FIG. 19-2

| | | | | |
|---|---|---|---|---|
| CTGGATAAAA | TTACAGGGAT | GCAGAATGAG | ACACTTTATC | TATCAGGACG | AAAAATCACA | 3180
| TAAATTCAGG | GCAGTTGAGC | AACAGGGAAA | CGAGTTGCAT | ATCAGTTGGG | GAAAAGTTGG | 3240
| CACCAAAGGC | AAAGCCAGAT | AAAAAGTTTT | TCAGATGCTG | CGGCAGCGGC | AAAAGCGGAG | 3300
| CCCGACCTCG | AGGGGGGGCC | CGGTACCCGG | CCGGACGTCT | CTAGAGCTAG | CTTGGCGAGA | 3360
| TTTTCAGGAG | CTAAGGAAGC | TAAAATGGAG | AAAAAAATCA | CTGGATATAC | CACCGTTGAT | 3420
| ATATCCCAAT | GGCATCGTAA | AGAACATTTT | GAGGCATTTC | AGTCAGTTGC | TCAATGTACC | 3480
| TATAACCAGA | CCGTTCAGCT | GGATATTACG | GCCTTTTTAA | AGACCGTAAA | GAAAAATAAG | 3540
| CACAAGTTTT | ATCCGGCCTT | TATTCACATT | CTTGCCCGCC | TGATGAATGC | TCATCCGGAA | 3600
| TTTCGTATGG | CAATGAAAGA | CGGTGAGCTG | GTGATATGGG | ATAGTGTTCA | CCCTTGTTAC | 3660
| ACCGTTTTCC | ATGAGCAAAC | TGAAACGTTT | TCATCGCTCT | GGAGTGAATA | CCACGACGAT | 3720
| TTCCGCAGT | TTCTACACAT | ATATTCGCAA | GATGTGGCGT | GTTACGGTGA | AAACCTGGCC | 3780
| TATTTCCCTA | AAGGGTTTAT | TGAGAATATG | TTTTTCGTCT | CAGCCAATCC | CTGGGTGAGT | 3840
| TTCACCAGTT | TTGATTTAAA | CGTTGGCCAAT | ATGGACAACT | TCTTCGCCCC | CGTTTTCACC | 3900
| ATGGGCAAAT | ATTATACGCA | AGGCGACAAG | GTGCTGATGC | CGCTGGCGAT | TCAGGTTCAT | 3960
| CATGCCGTCT | GTGATGGCTT | CCATGTCGCG | AGAATGCTTA | ATGAATTACA | ACAGTACTGC | 4020
| GATGAGTGGC | AGGGCGGGGC | GTAATTTTTT | TAAGGCAGTT | ATTGGTGCCC | TTAAACGCCT | 4080
| GGGTAATGA | CTCTCTAGCT | TGAGGCATCA | AATAAAACGA | AAGGCTCAGT | CGAAAGACTG | 4140
| GGCCTTTCGT | TTTATCTGTT | GTTTGTCGGT | GAACGCTCTC | CTGAGTAGGA | CAAATCCGCC | 4200
| GCTCTAGAGC | TGCCTCGCGC | GTTTCGGTGA | TGACGGTGAA | AACCTCTGAC | ACATGCAGCT | 4260
| CCCGGAGACG | GTCACAGCTT | GTCTGTAAGC | GGATGCCGGG | AGCAGACAAG | CCCGTCAGGG | 4320
| CGCGTCAGCG | GGTGTTGGCG | GGTGTCGGGG | CGCAGCCATG | ACCCAGTCAC | GTAGCGATAG | 4380
| CGGAGTGTAT | ACTGGCTTAA | CTATGCGGCA | TCAGAGCAGA | TTGTACTGAG | AGTGCACCAT | 4440
| ATGCGGTGTG | AAATACCGCA | CAGATGCGTA | AGGAGAAAAT | ACCGCATCAG | GCGCTCTTCC | 4500
| GCTTCCTCGC | TCACTGACTC | GCTGCGCTCG | GTCTGTCGGC | TGCGGCGAGC | GGTATCAGCT | 4560
| CACTCAAAGG | CGGTAATACG | GTTATCCACA | GAATCAGGGG | ATAACGCAGG | AAAGAACATG | 4620
| TGAGCAAAAG | GCCAGCAAAA | GGCCAGGAAC | CGTAAAAAGG | CCGCGTTGCT | GGCGTTTTTC | 4680

FIG. 19-3

```
CATAGGCTCC GCCCCCCTGA CGAGCATCAC AAAAATCGAC GCTCAAGTCA GAGGTGGCGA 4740
AACCCGACAG GACTATAAAG ATACCAGGCG TTTCCCCCTG GAAGCTCCCT CGTGCGCTCT 4800
CCTGTTCCGA CCCTGCCGCT TACCGGATAC CTGTCCGCCT TTCTCCCTTC GGGAAGCGTG 4860
GCGCTTTCTC AATGCTCACG CTGTAGGTAT CTCAGTTCGG TGTAGGTCGT TCGCTCCAAG 4920
CTGGGCTGTG TGCACGAACC CCCCGTTCAG CCCGACCGCT GCGCCTTATC CGGTAACTAT 4980
CGTCTTGAGT CCAACCCGGT AAGACACGAC TTATCGCCAC TGGCAGCAGC CACTGGTAAC 5040
AGGATTAGCA GAGCGAGGTA TGTAGGCGGT GCTACAGAGT TCTTGAAGTG GTGGCCTAAC 5100
TACGGCTACA CTAGAAGGAC AGTATTTGGT ATCTGCGCTC TGCTGAAGCC AGTTACCTTC 5160
GGAAAAAGAG TTGGTAGCTC TTGATCCGGC AAACAAACCA CCGCTGGTAG CGGTGGTTTT 5220
TTTGTTTGCA AGCAGCAGAT TACGCGCAGA AAAAAAGGAT CTCAAGAAGA TCCTTTGATC 5280
TTTTCTACGG GGTCTGACGC TCAGTGGAAC GAAAACTCAC GTTAAGGGAT TTTGGTCATG 5340
AGATTATCAA AAAGGATCTT CACCTAGATC CTTTTAAATT AAAAATGAAG TTTTAAATCA 5400
ATCTAAAGTA TATATGAGTA AACTTGGTCT GACAGTTACC AATGCTTAAT CAGTGAGGCA 5460
CCTATCTCAG CGATCTGTCT ATTTCGTTCA TCCATAGCTG CCTGACTCCC CGTCGTGTAG 5520
ATAACTACGA TACGGGAGGG CTTACCATCT GGCCCCAGTG CTGCAATGAT ACCGCGAGAC 5580
CCACGCTCAC CGGCTCCAGA TTTATCAGCA ATAAACCAGC CAGCCGGAAG GGCCGAGCGC 5640
AGAAGTGGTC CTGCAACTTT ATCCGCCTCC ATCCAGTCTA TTAATTGTTG CCGGGAAGCT 5700
AGAGTAAGTA GTTCGCCAGT TAATAGTTTG CGCAACGTTG TTGCCATTGC TACAGGCATC 5760
GTGGTGTCAC GCTCGTCGTT TGGTATGGCT TCATTCAGCT CCGGTTCCCA ACGATCAAGG 5820
CGAGTTACAT GATCCCCCAT GTTGTGCAAA AAAGCGGTTA GCTCCTTCGG TCCTCCGATC 5880
GTTGTCAGAA GTAAGTTGGC CGCAGTGTTA TCACTCATGG TTATGGCAGC ACTGCATAAT 5940
TCTCTTACTG TCATGCCATC CGTAAGATGC TTTTCTGTGA CTGGTGAGTA CTCAACCAAG 6000
TCATTCTGAG AATAGTGTAT GCGGCGACCG AGTTGCTCTT GCCCGGCGTC AATACGGGAT 6060
AATACCGCGC CACATAGCAG AACTTTAAAA GTGCTCATCA TTGGAAAACG TTCTTCGGGG 6120
CGAAAACTCT CAAGGATCTT ACCGCTGTTG AGATCCAGTT CGATGTAACC CACTCGTGCA 6180
CCCAACTGAT CTTCAGCATC TTTTACTTTC ACCAGCGTTT CTGGGTGAGC AAAAACAGGA 6240
```

FIG. 19-4

```
AGGCAAAATG CCGCAAAAAA GGGAATAAGG GCGACACGGA AATGTTGAAT ACTCATACTC 6300
TTCCTTTTTC AATATTATTG AAGCATTTAT CAGGGTTATT GTCTCATGAG CGGATACATA 6360
TTTGAATGTA TTTAGAAAAA TAAACAAATA GGGGTTCCGC GCACATTTCC CCGAAAAGTG 6420
CCACCTGACG TCTAAGAAAC CATTATTATC ATGACATTAA CCTATAAAAA TAGGCGTATC 6480
ACGAGGCCCT TTCGTCTTCA C                                          6501
```

```
CTCGAGAAAT CATAAAAAAT TTATTTGCTT TGTGAGCGGA TAACAATTAT AATAGATTCA   60
ATTGTGAGCG GATAACAATT TCACACAGAA TTCATTAAAG AGGAGAAATT AACTATGAGA  120
GGATCGCATC ACCATCACCA TCACGGATCC GGCATCATGG TTCGACCATT GAACTCGATC  180
GTCGCCGTGT CCCAAATAT GGGGATTGGC AAGAACGGAG ACCTACCCTG GCCTCCGCTC  240
AGGAACGAGT TCAAGTACTT CCAAAGAATG ACCACAACCT CTTCAGTGGA AGGTAAACAG  300
AATCTGGTGA TTATGGGTAG GAAAACCTGG TTCTCCATTC CTGAGAAGAA TCGACCTTTA  360
AAGGACAGAA TTAATATAGT TCTCAGTAGA GAACTCAAAG AACCACCACG AGGAGCTCAT  420
TTTCTTGCCA AAGTTTGGA TGATGCCTTA AGACTTATTG AACAACCGGA ATTGGCAAGT  480
AAAGTAGACA TGGTTTGGAT AGTCGGAGGC AGTTCTGTTT ACCAGGAAGC CATGAATCAA  540
CCAGGCCACC TTAGACTCTT TGTGACAAGG ATCATGCAGG AATTTGAAAG TGACACGTTT  600
TTCCCAGAAA TTGATTTGGG GAAATATAAA CTTCTCCCAG AATACCCAGG CGTCCTCTCT  660
GAGGTCCAGG AGGAAAAAGG CATCAAGTAT AAGTTTGAAG TCTACGAGAA GAAAGGTTGG  720
AAGATCTTAA GCTTAATTAG CTGAGCTTGG ACTCCTGTTG ATAGATCCAG TAATGACCTC  780
AGAACTCCAT CTGGATTTGT TCAGAACGCT CGGTTGCCGC CGGGCGTTTT TTATTGGTGA  840
GAATCCAAGC TAGCTCTAGA GACGTCCGGA CGGAGCTCCA CCGCGGTGGC GGCCGCTCTA  900
GAGTCACTTA CTTAACATTT TCCCATTTGG TACTATCTAA CCCCTTTTCA CTATTAAGAA  960
GTAATGCCTA CTATGACTCA AGTCGCGAAG AAAATTCTGG TGACGTGCGC ACTGCCGTAC 1020
GCTAACGGCT CAATCCACCT CGGCCATATG CTGGAGCACA TCCAGGCTGA TGTCTGGGTC 1080
CGTTACCAGC GAATGCGCGG CCACGAGGTC AACTTCATCT GCGCCGACGA TGCCACGGGT 1140
ACACCGATCA TGCTGAAAGC TCAGCAGCTT GGTATCACCC CGGAGCAGAT CAACTATCAC 1200
ATGAGTCAGG AGCATCAGAC TGATTTCGCA GGCTTTAACA TCAGCTATGA CCTGAAAGAA 1260
TCGACGCACA GCGAAGAGAA CCGCCAGTTG TCAGAACTTA TCTACTCTCG CCTGAAAGAA 1320
AACGGTTTTA TTAAAAACCG CACCATCTCT CAGCTGTACG ATCCCGAAAA AGGCATGTTC 1380
CTGCCCGACC GTTTGTGAA AGGCACCTGC AATCCCCGGA TCAATACGGC 1440
GATAACTGCG AAGTCTGCGG CGCGACCTAC AGCCCGACTG AACTGATCGA GCCGAAATCG 1500
GTGGTTTCTG GCGCTACGCC GGTAATGCGT GATTCTGAAC ACTTCTTCTT TGATCTGCCC 1560
```

| | | | | |
|---|---|---|---|---|
| TCTTTCAGCG | AAATGTTGCA | GGCATGGACC | CGCAGCGGTG | CGTTGCAGGA | GCAGGTGGCA | 1620 |
| AATAAAATGC | AGGAGTGGTT | TGAATCTGGC | CTGCAACAGT | GGGATATCTC | CCGCGACGCC | 1680 |
| CCTTACTTCG | GTTTTGAAAT | TCCGAACGCG | CCGGGCAAAT | ATTTCTACGT | CTGGCTGGAC | 1740 |
| GCACCGATTG | GCTACATGGG | TTCTTTCAAG | AATCTGTGCG | ACAAGCGCGG | CGACAGCGTA | 1800 |
| AGCTTCGATG | AATACTGGAA | GAAAGACTCC | ACCGCCGAGC | TGTACCACTT | CATCGGTAAA | 1860 |
| GATATTGTTT | ACTTCCACAG | CCTGTTCTTC | CCTGCCATGC | TGGAAGGCAG | CAACTTCCGC | 1920 |
| AAGCCGTCCA | ACCTGTTTGT | TCATGGCTAT | GTGACGGTGA | ACGGCGCAAA | GATGTCCAAG | 1980 |
| TCTCGCGGCA | CCTTTATTAA | AGCCAGCACC | TGGCTGAATC | ATTTTGACGC | AGACAGCCTG | 2040 |
| CGTTACTACT | ACACTGCGAA | ACTCTCTTCG | CGCATTGATG | ATATCGATCT | CAACCTGGAA | 2100 |
| GATTTCGTTC | AGCGTGTGAA | TGCCGATATC | GTTAACAAAG | TGGTTAACCT | GGCCTCCCGT | 2160 |
| AATGCGGGCT | TTATCAACAA | GCGGTTTTGA | GGCGTGCTGG | CAAGCGAACT | GGCTGACCCG | 2220 |
| CAGTTGTACA | AAACCTTCAC | TGATGCCGCT | GAAGTGATTG | GTGAAGCGTG | GGAAAGCCGT | 2280 |
| GAATTTGGTA | AAGCCGTGCG | CGAAATCATG | GCGCTGGCTG | ATCTGGCTAA | CCGCTATGTC | 2340 |
| GATGAACAGG | CTCCGTGGGT | GGTGGCGAAA | CAGGAAGGCC | GCGATGCCGA | CCTGCAGGCA | 2400 |
| ATTGCTCAA | TGGGCATCAA | CCTGTTCCGC | GTGCTGATGA | CTTACCTGAA | GCCGGTACTG | 2460 |
| CCGAAAACTGA | CCGAGCGTGC | AGAAGCATTC | CTCAATACGG | AACTGACCTG | GGATGGTATC | 2520 |
| CAGCAACCGC | TGCTGGGCCA | CAAAGTGAAT | CCGTTCAAGG | CGCTGTATAA | CCGCATCGAT | 2580 |
| ATGAGGCAGG | TTGAAGCACT | GGTGGAAGCC | TCTAAATGAG | AAGTAAAAGC | CGCTGCCGCG | 2640 |
| CCGGTAACTG | GCCCGCTGGC | AGATGATCCG | ATTCAGGAAA | CCATCACCTT | TGACGACTTC | 2700 |
| GCTAAAGTTG | ACCTGCGCGT | GGCGCTGATT | GAAAACGCAG | AGTTTGTTGA | AGGTTCTGAC | 2760 |
| AAACTGCTGC | GCCTGACGCT | GGATCTCGGC | GGTGAAAAAC | GCAATGTCTT | CTCCGGTATT | 2820 |
| CGTTCTGCTT | ACCCGGATCC | GCAGGCACTG | ATTGGTCGTC | ACACCATTAT | GGTGGCTAAC | 2880 |
| CTGGCACCAC | GTAAAATGCG | CTTCGGTATC | TCTGAAGGCA | TGCCGGTCCT | TCATCAGGTG | 2940 |
| GGCGGGAAAG | ATATTTTCCT | GCTAAGCCCG | GATGCCGGTG | CTAAACCGGG | TCATCAGGTG | 3000 |
| AAATAATCCC | CCTTCAAGGC | GCTGCATCGA | CAGCCTTTTG | CTTTATAAAT | TCCTAAAGTT | 3060 |
| GTTTTCTTGC | GATTTTGTCT | CTCTCTAACC | CGCATAAATA | CTGGTAGCAT | CTGCATTCAA | 3120 |

FIG. 20-2

```
CTGGATAAAA TTACAGGGAT GCAGAATGAG ACACTTTATC TATCAGGACG AAAAATCACA 3180
TAAATTCAGG GCAGTTGAGC AACAGGGAAA CGAGTTGCAT ATCAGTTGGG GAAAAGTTGG 3240
CACCAAAGGC AAAGCCAGAT AAAAAGTTTT TCAGATGCTG CGGCAGCGGC AAAAGCGGAG 3300
CCCGACCTCG AGGGGGGGCC CGGTACCCGG CCCGACGTCT CTAGAGCTAG CTTGGCGAGA 3360
TTTCAGGAG CTAAGGAAGC TAAAATGGAG AAAAAAATCA CTGGATATAC CACCGTTGAT 3420
ATATCCCAAT GGCATCGTAA AGAACATTTT GAGGCATTTC AGTCAGTTGC TCAATGTACC 3480
TATAACCAGA CCGTTCAGCT GGATATTACG GCCTTTTTAA AGACCGTAAA GAAAAATAAG 3540
CACAAGTTTT ATCCGGCCTT TATTCACATT CTTGCCCGCC TGATGAATGC TCATCCGGAA 3600
TTTCGTATGG CAATGAAAGA CGGTGAGCTG GTGATATGGG ATAGTGTTCA CCCTTGTTAC 3660
ACCGTTTTCC ATGAGCAAAC TGAAACGTTT TCATCGCTCT GGAGTGAATA CCACGACGAT 3720
TTCCGGCAGT TTCTACACAT GATGTGGCGT GTTACGGTGA AAACCTGCC CTGGGTGAGT 3780
TATTTCCCTA AAGGGTTTAT TGAGAATATG TTTTTCGTCT CAGCCAATCC CGTTTTCACC 3840
TTCACCAGTT TTGATTTAAA CGTGGCCAAT ATGGACAACT TCTTCGCCCC CGTTTGCCCC 3900
ATGGGCAAAT ATTATACGCA AGGCGACAAG GTGCTGATGC CGCTGGCGAT TCAGGTTCAT 3960
CATGCCGTCT GTGATGGCTT CCATGTCGGC AGAATGCTTA ATGAATTACA ACAGTACTGC 4020
GATGAGTGGC AGGGCGGGGC GTAATTTTT TAAGGCAGTT ATTGGTGCCC TTAAACGCCT 4080
GGGTAATGA CTCTCTAGCT TGAGGCATCA AATAAAACGA AAGGCTCAGT CGAAAGACTG 4140
GGCCTTTCGT TTTATCTGTT GTTTGTCGGT GAACGCTCTC CTGAGTAGGA CAAATCCGCC 4200
GCTCTAGAGC TGCCTCGCGC GTTTCGGTGA TGACGGTGAA AACCTCTGAC ACATGCAGCT 4260
CCCGGAGACG GTCACAGCTT GTCTGTAAGC GGATGCCGGG AGCAGACAAG CCCGTCAGGG 4320
CGCGTCAGCG GGTGTTGGCG GGTGTCGGGG CGCAGCCATG ACCCAGTCAC GTAGCGATAG 4380
CGGAGTGTAT ACTGGCTTAA CTATGCGGCA TCAGAGCAGA TTGTACTGAG AGTGCACCAT 4440
ATGCGGTGTG AAATACCGCA CAGATGCGTA AGGAGAAAAT ACCGCATCAG GCGCTCTTCC 4500
GCTTCCTCGC TCACTGACTC GCTGCGCTCG GTCTGTCGGG TGCGGCGAGC GGTATCAGCT 4560
CACTCAAAGG CGGTAATACG GTTATCCACA GAATCAGGGG ATAACGCAGG AAAGAACATG 4620
TGAGCAAAAG GCCAGCAAAA GGCCAGGAAC CGTAAAAAGG CCGCGTTGCT GGCGTTTTTC 4680
```

FIG. 20-3

```
CATAGGCTCC GCCCCCTGA CGAGCATCAC AAAAATCGAC GCTCAAGTCA GAGGTGGCGA 4740
AACCCGACAG GACTATAAAG ATACCAGGCG TTTCCCCCTG GAAGCTCCCT CGTGCGCTCT 4800
CCTGTTCCGA CCCTGCCGCT TACCGGATAC CTGTCCGCCT TTCTCCCTTC GGGAAGCGTG 4860
GCGCTTTCTC AATGCTCACG CTGTAGGTAT CTCAGTTCGG TGTAGGTCGT TCGCTCCAAG 4920
CTGGGCTGTG TGCACGAACC CCCCGTTCAG CCCGACCGCT GCGCCTTATC CGGTAACTAT 4980
CGTCTTGAGT CCAACCCGGT AAGACACGAC TTATCGCCAC TGGCAGCAGC CACTGGTAAC 5040
AGGATTAGCA GAGCGAGGTA TGTAGGCGGT GCTACAGAGT TCTTGAAGTG GTGGCCTAAC 5100
TACGGCTACA CTAGAAGGAC AGTATTTGGT ATCTGCGCTC TGCTGAAGCC AGTTACCTTC 5160
GGAAAAAGAG TTGGTAGCTC TTGATCCGGC AAACAAACCA CCGCTGGTAG CGGTGGTTTT 5220
TTTGTTTGCA AGCAGCAGAT TACGCGCAGA AAAAAAGGAT CTCAAGAAGA TCCTTTGATC 5280
TTTTCTACGG GGTCTGACGC TCAGTGGAAC GAAAACTCAC GTTAAGGGAT TTTGGTCATG 5340
AGATTATCAA AAAGGATCTT CACCTAGATC CTTTTAAATT AAAAATGAAG TTTTAAATCA 5400
ATCTAAAGTA TATATGAGTA AACTTGGTCT GACAGTTACC AATGCTTAAT CAGTGAGGCA 5460
CCTATCTCAG CGATCTGTCT ATTTCGTTCA TCCATAGCTG CCTGACTCCC CGTCGTGTAG 5520
ATAACTACGA TACGGGAGGG CTTACCATCT GGCCCCAGTG CTGCAATGAT ACCGCGAGAC 5580
CCACGCTCAC CGGCTCCAGA TTTATCAGCA ATAAACCAGC CAGCCGGAAG GGCCGAGCGC 5640
AGAAGTGGTC CTGCAACTTT ATCCGCCTCC ATCCAGTCTA TTAATTGTTG CCGGGAAGCT 5700
AGAGTAAGTA GTTCGCCAGT TAATAGTTTG CGCAACGTTG TTGCCATTGC TACAGGCATC 5760
GTGGTGTCAC GCTCGTCGTT TGGTATGGCT TCATTCAGCT CCGGTTCCCA ACGATCAAGG 5820
CGAGTTACAT GATCCCCCAT GTTGTGCAAA AAAGCGGTTA GCTCCTTCGG TCCTCCGATC 5880
GTTGTCAGAA GTAAGTTGGC CGCAGTGTTA TCACTCATGG TTATGGCAGC ACTGCATAAT 5940
TCTCTTACTG TCATGCCATC CGTAAGATGC TTTTCTGTGA CTGGTGAGTA CTCAACCAAG 6000
TCATTCTGAG AATAGTGTAT GCGGCGACCG AGTTGCTCTT GCCCGGCGTC AATACGGGAT 6060
AATACCGCGC CACATAGCAG AACTTTAAAA GTGCTCATCA TTGGAAAACG TTCTTCGGGG 6120
CGAAAACTCT CAAGGATCTT ACCGCTGTTG AGATCCAGTT CGATGTAACC CACTCGTGCA 6180
CCCAACTGAT CTTCAGCATC TTTTACTTTC ACCAGCGTTT CTGGGTGAGC AAAAACAGGA 6240
```

FIG. 20-4

```
AGGCAAAATG CCGCAAAAAA GGGAATAAGG GCGACACGGA AATGTTGAAT ACTCATACTC 6300
TTCCTTTTTC AATATTATTG AAGCATTTAT CAGGGTTATT GTCTCATGAG CGGATACATA 6360
TTTGAATGTA TTTAGAAAAA TAAACAAATA GGGGTTCCGC GCACATTTCC CCGAAAAGTG 6420
CCACCTGACG TCTAAGAAAC CATTATTATC ATGACATTAA CCTATAAAAA TAGGCGTATC 6480
ACGAGGCCCT TTCGTCTTCA C                                          6501
```

FIG. 20-5

OVEREXPRESSION OF AMINOACYL-TRNA SYNTHETASES FOR EFFICIENT PRODUCTION OF ENGINEERED PROTEINS CONTAINING AMINO ACID ANALOGUES

This application is a continuation of U.S. application Ser. No. 09/767,515 filed Jan. 23, 2001, now issued as U.S. Pat. No. 6,586,207; which claims priority under 35 USC § 119(e) of U.S. application Ser. No. 60/207,627 filed May 26, 2000, now abandoned. The disclosure of each of the prior applications is considered part of and is incorporated by reference in the disclosure of this application.

This invention was made with Government support under NSF Grant Nos. NSF DMR-9996048 and US Army Research Grant DAAG55-98-1-0518. The Government has certain rights in this invention.

Throughout this application various publications are referenced. The disclosures of these publications in their entireties are hereby incorporated by reference into this application in order to more fully describe the state of the art to which this invention pertains.

FIELD OF INVENTION

The present invention relates to novel compositions and methods, for incorporating amino acid analogues into proteins in vivo, by overexpression of aminoacyl-tRNA synthetases.

BACKGROUND OF INVENTION

Expanding the scope of biological polymerizations to include non-natural monomers, is an area of growing interest, with important theoretical and practical consequences. An early and critically important example of such studies was the demonstration that "dideoxy" nucleotide monomers can serve as substrates for DNA polymerases. Advances in DNA sequencing (F. Sanger, S. Nicklen, A. R. Coulson, *Proc. Natl. Acad. Sci. USA* 1977, 74, 5463–5467), DNA base pairing models (M. J. Lutz, S. A. Benner, S. Hein, G. Breipohl, E. Uhlmann, *J. Am. Chem. Soc.* 1997, 119, 3177–3178; J. C. Morales, E. T. Kool, *Nature Struct. Biol.* 1998, 5, 950–954), materials synthesis (W. H. Park, R. W. Lenz, S. Goodwin, *Macromolecules* 1998, 31, 1480–1486; Y. Doi, S. Kitamura, H. Abe, *Macromolecules* 1995, 28, 4822–4828), and cell surface engineering (K. J. Yarema, L. K. Mahal, R. E. Bruehl, E. C. Rodriguez, C. R. Bertozzi, *J. Biol. Chem.* 1998, 273, 31168–31179; L. K. Mahal, K. J. Yarema, C. R. Bertozzi, *Science* 1997, 276, 1125–1128; Saxon, E. and Bertozzi, C. R. *Science* 2000, 287, 2007–2010) have resulted from the recognition of non-natural monomers by the enzymes that control these polymerizations.

Recent investigations have shown the incorporation of modified or completely "synthetic" bases into nucleic acids (Matray, T. J.; Kool, E. T. *Nature* 1999, 399, 704; Kool, E. T. *Biopolymers* 1998, 48, 3; Morales, J. C.; Kool, E. T. *Nature Struct. Biol.* 1998, 5, 950; Guckian, K. M.; Kool, E. T.; *Angew. Chem. Int. Ed. Eng* 1998, 36, 2825; Liu, D. Y.; Moran, S.; Kool, E. T. *Chem. Biol.* 1997, 4, 919; Moran, S.; Ren, R. X. F.; Kool, E. T. *Proc. Natl. Acad. Sci. USA* 1997, 94, 10506; Moran, S. et al. *J. Am. Chem. Soc.* 1997, 119, 2056; Benner, S. A. et al. *Pure Appl. Chem.* 1998, 70, 263; Lutz, M. J.; Horlacher J.; Benner, S. A. *Bioorg. Med. Chem. Lett.* 1998, 8, 1149; Lutz, M. J.; Held, H. A.; Hottiger, M.; Hubscher, U.; Benner, S. A. *Nuc. Acids Res.* 1996, 24, 1308; Horlacher, J. et al. *Proc. Natl. Acad. Sci. USA* 1995, 92, 6329; Switzer, C. Y.; Moroney, S. E.; Benner, S. A. *Biochemistry* 1993, 32, 10489; Lutz, M. J.; Horlacher, J.; Benner, S. A. *Bioorg. Med. Chem. Lett.* 1998, 8, 499; Switzer, C.; Moroney, S. E.; Benner, S. A. *J. Am. Chem. Soc.* 1989, 111, 8322; Piccirilli, J. A.; Krauch, T.; Moroney, S. E.; Benner, S. A. *Nature* 1990, 343–33), while materials researchers have exploited the broad substrate range of the poly(β-hydroxyalkanoate) (PHA) synthases to prepare novel poly(β-hydroxyalkanoate)s (PHAs) with unusual physical properties (Kim, Y. B.; Rhee, Y. H.; Lenz, R. W. *Polym. J* 1997, 29, 894; Hazer, B.; Lenz, R. W.; Fuller, R. C. *Polymer* 1996, 37, 5951; Lenz, R. W.; Kim, Y. B.; Fuller, R. C. *FEMS Microbiol. Rev.* 1992, 103, 207; Park, W. H.; Lenz, R. W.; Goodwin, S. *Macromolecules* 1998, 31, 1480; Ballistreri, A. et al. *Macromolecules* 1995, 28, 3664; Doi, Y.; Kitamura, S.; Abe, H. *Macromolecules* 1995, 28, 4822): Novel polymeric materials with unusual physical and/or chemical properties are also useful in polymer chemistry. The last several decades have shown many advances in synthetic polymer chemistry that provide the polymer chemist with increasing control over the structure of macromolecules (Szwarc, M. *Nature* 1956, 178, 1168–1169 Szwarc, M. *Nature* 1956, 178, 1168–1169; Faust, R.; Kennedy, J. P. *Polym. Bull.* 1986, 15, 317–323; Schrock, R. R. *Acc. Chem. Res.* 1990, 23, 158–165; Corradini, P. *Macromol. Symp.* 1995, 89, 1–11; Brintzinger, H. H.; Fischer, D.; Mulhaupt, R.; Rieger, B.; Waymouth, R. M. *Angew. Chem. Int. Ed. Engl.* 1995, 34, 1143–1170; Dias, E. L.; SonBinh, T. N.; Grubbs, R. H. *J. Am. Chem. Soc.* 1997, 119, 3887–3897; Chiefari, J. et al. *Macromolecules* 1998, 31, 5559–5562). However, none of these methods have provided the level of control that is the basis of the exquisite catalytic, informational, and signal transduction capabilities of proteins and nucleic acids (Ibba, M.; Soll, D. *Science* 1999, 286, 1893–1897). There remains a need for control over protein synthesis to design and produce artificial proteins having advantageous properties.

For this reason, the design and synthesis of artificial proteins that exhibit novel and potentially useful structural properties have been investigated. Harnessing the molecular weight and sequence control provided by in vivo synthesis would permit control of folding, functional group placement, and self-assembly at the angstrom length scale. Proteins that have been produced by in vivo methods exhibit predictable chain-folded lamellar architectures (Krejchi, M. T.; Atkins, E. D. T.; Waddon, A. J.; Fournier, M. J.; Mason, T. L.; Tirrell, D. A. *Science* 1994, 265, 1427–1432; Parkhe, A. D.; Fournier, M. J.; Mason, T. L.; Tirrell, D. A. *Macromolecules* 1993, 26(24), 6691–6693; McGrath, K. P.; Fournier, M. J.; Mason, T. L.; Tirrell, D. A. *J. Am. Chem. Soc.* 1992, 114, 727–733; Creel, H. S.; Fournier, M. J.; Mason, T. L.; Tirrell, D. A. *Macromolecules* 1991, 24, 1213–1214), unique smectic liquid-crystalline structures with precise layer spacings (Yu, S. M.; Conticello, V.; Zhang, G.; Kayser, C.; Fournier, M. J.; Mason, T. L.; Tirrell, D. A. *Nature* 1997, 389, 187–190), and controlled reversible gelation (Petka, W. A.; Hardin, J. L.; McGrath, K. P.; Wirtz, D.; Tirrell, D. A. *Science* 1998, 281, 389–392). The demonstrated ability of these protein polymers to form unique macromolecular architectures will be of importance for engineering materials with interesting liquid-crystalline, crystalline, surface, electronic, and optical properties.

Novel chemical and physical properties that can be engineered into protein polymers may be expanded by the precise placement of amino acid analogues. Efforts to incorporate novel amino acids into proteins in vivo have relied on the ability of the translational apparatus to recognize amino acid analogues that differ in structure and functionality from the natural amino acids. The in vivo incorporation of amino acid analogues into proteins is controlled most stringently by the aminoacyl-tRNA synthetases (AARS), the class of enzymes that safeguards the fidelity of amino acid incorporation into proteins (FIG. 1). The DNA message is translated into an amino acid sequence via the pairing of the codon of the messenger RNA (mRNA) with the complementary anticodon of the aminoacyl-tRNA. Aminoacyl-tRNA synthetases control the fidelity of amino acid attachment to the tRNA. The discriminatory power of the aminoacyl-tRNA synthetase places severe limits on the set of amino acid structures that can be exploited in the engineering of natural and artificial proteins in vivo.

Several strategies for circumventing the specificity of the synthetases have been explored. Introduction of amino acid analogues can be achieved relatively simply via solid-phase peptide synthesis (Merrifield, R. B. *Pure & Appl. Chem.* 1978, 50, 643–653). While this method circumvents all biosynthetic machinery, the multistep procedure is limited to synthesis of peptides less than or equal to approximately 50 amino acids in length, and is therefore not suitable for producing protein materials of longer amino acid sequences.

Chemical aminoacylation methods, introduced by Hecht and coworkers (Hecht, S. M. *Acc. Chem. Res.* 1992, 25, 545; Heckler, T. G.; Roesser, J. R.; Xu, C.; Chang, P.; Hecht, S. M. *Biochemistry* 1988, 27, 7254; Hecht, S. M.; Alford, B. L.; Kuroda, Y.; Kitano, S. *J. Biol. Chem.* 1978, 253, 4517) and exploited by Schultz, Chamberlin, Dougherty and others (Cornish, V. W.; Mendel, D.; Schultz, P. G. *Angew. Chem. Int. Ed. Engl.* 1995, 34, 621; Robertson, S. A.; Ellman, J. A.; Schultz, P. G. *J. Am. Chem. Soc.* 1991, 113, 2722; Noren, C. J.; Anthony-Cahill, S. J.; Griffith, M. C.; Schultz, P. G. *Science* 1989, 244, 182; Bain, J. D.; Glabe, C. G.; Dix, T. A.; Chamberlin, A. R. *J. Am. Chem. Soc.* 1989, 111, 8013; Bain, J. D. et al. *Nature* 1992, 356, 537; Gallivan, J. P.; Lester, H. A.; Dougherty, D. A. *Chem. Biol.* 1997, 4, 740; Turcatti, et al. *J. Biol. Chem.* 1996, 271, 19991; Nowak, M. W. et al. *Science,* 1995, 268, 439; Saks, M. E. et al. *J. Biol. Chem.* 1996, 271, 23169; Hohsaka, T. et al. *J. Am. Chem. Soc.* 1999, 121, 34), avoid the synthetases altogether, but provide low protein yields.

Alteration of the synthetase activities of the cell is also possible, either through mutagenesis or through introduction of heterologous synthetases (Ibba, M.; Hennecke, H. *FEBS Lett.* 1995, 364, 272; Liu, D. R.; Maghery, T. J.; Pastrnak, M.; Schultz, P. G. *Proc. Natl. Acad. Sci. USA,* 1997, 94, 10092; Furter, R. *Protein Sci.* 1998, 7, 419; Ohno, S. et al., *J. Biochem.* 1998, 124, 1065; Liu, D. R.; Schultz, P. G. *Proc. Natl. Acad. Sci.* 1999, 96, 4780; Wang, L.; Magliery, T. J.; Liu, D. R.; Schultz, P. G. *J. Am. Chem. Soc.* 2000, 122, 5010–5011; Pastrnak, M.; Magliety, T. J.; Schultz, P. G. *Helv. Chim. Acta* 2000, 83, 2277–2286).

In some instances, the ability of the wild-type synthetases to accept amino acid analogues has been exploited. For example, wild-type synthetases have been shown to activate and charge substrates other than the canonical, proteinogenic amino acids (Cowie, D. B.; Cohen, G. N. *Biochim. Biophys. Acta.* 1957, 26, 252; Richmond, M. H. *Bacteriol Rev.* 1962, 26, 398; Horton, G.; Boime, I. *Methods Enzymol.* 1983, 96, 777; Wilson, M. J.; Hatfield, D. L. *Biochim. Biophys. Acta* 1984, 781, 205). This approach offers important advantages with respect to synthetic efficiency, in that neither chemical acylation of tRNA nor cell-free translation is required. The simplicity of the in vivo approach, its relatively high synthetic efficiency, and its capacity for multisite substitution, make it the method of choice for production of protein materials whenever possible.

The capacity of the wild-type translational apparatus has been previously demonstrated to utilize amino acid analogues bearing fluorinated (Richmond, M. H. *J. Mol. Biol.* 1963, 6, 284; Fenster, E. D.; Anker, H. S. *Biochemistry* 1969, 8, 268; Yoshikawa, E.; Fournier, M. J.; Mason, T. L.; Tirrell, D. A. *Macromolecules* 1994, 27, 5471), unsaturated (Van Hest, J. C. M.; Tirrell, D. A. *FEBS Lett.* 1998, 428, 68; Deming, T. J.; Fournier, M. J.; Mason, T. L.; Tirrell, D. A. *J. Macromol. Sci.—Pure Appl. Chem.* 1997, A34, 2134), electroactive (Kothakota, S.; Mason, T. L.; Tirrell, D. A.; Fournier, M. J. *J. Am. Chem. Soc.* 1995, 117, 536), and other useful side chain functions. The chemistries of the above functional groups are distinct from the chemistries of the amine, hydroxyl, thiol, and carboxylic acid functional groups characteristic of proteins; this makes their incorporation particularly attractive for targeted chemical modification of proteins.

For example, alkene functionality introduced into artificial proteins via dehydroproline can be quantitatively modified via bromination and hydroxylation (Deming, T. J.; Fournier, M. J.; Mason, T. L.; Tirrell, D. A. *J. Macromol. Sci. Pure Appl. Chem.* 1997, A34, 2143–2150). Alkene functionality, introduced by incorporation of other amino acid analogues, should be useful for chemical modification of proteins by olefin metathesis (Clark, T. D.; Kobayashi, K.; Ghadiri, M. R. *Chem. Eur. J.* 1999, 5, 782–792; Blackwell, H. E.; Grubbs, R. H. *Angew. Chem. Int. Ed. Engl.* 1998,. 37, 3281–3284), palladium-catalyzed coupling (Amatore, C.; Jutand, A. *J. Organomet. Chem.* 1999, 576, 255–277; Tsuji, J. *Palladium Reagents and Catalysts: Innovations in Organic Synthesis*; John Wiley and Sons: New York, 1995; Schoenberg, A.; Heck, R. F. *J. Org. Chem.* 1974, 39, 3327–3331), and other chemistries (Trost, B. M.; Fleming, I., Eds. *Comprehensive Organic Synthesis*; Pergamon Press; Oxford, 1991). The incorporation of fluorinated functional groups into proteins has imparted to protein films the low surface energy characteristic of fluoropolymers; contact angles of hexadecane on fluorinated protein polymers (70°) are much higher than those on unfluorinated controls (17°) (Yoshikawa, E.; Fournier, M. J.; Mason, T. L.; Tirrell, D. A. *Macromolecules* 1994, 27, 5471–5475).

Methionine (1) (FIG. 1) is a possible target for substitution by amino acid analogues, with its hydrophobicity and polarizability, make it an important amino acid for regulating protein structure and protein-protein recognition processes (T. Yuan, A. M. Weljie, H. J. Vogel, *Biochemistry* 1998, 37, 3187–3195; H. L. Schenck, G. P. Dado, S. H. Gellman, *J. Am. Chem. Soc.* 1996, 118, 12487–12494; Maier, K. L.; Lenz, A. G., Beck-Speier, I.; Costabel, U. *Methods Enzymol.* 1995, 251, 455–461). Replacement of methionine by its analogues may therefore permit purposeful manipulation of these properties.

Several analogues of methionine (1), specifically selenomethionine, telluromethionine, norleucine, trifluoromethionine and ethionine (Hendrickson, W. A.; Horton, J. R.; Lemaster, D. M. *EMBO J.* 1990, 9, 1665; Boles, J. O. et al *Nature Struct. Biol.* 1994, 1, 283; Cowie, D. B.; Cohen, G. N.; Bolton, E. T.; de Robichon-Szulmajster, H. *Biochim. Biophys. Acta* 1959, 34, 39; Duewel, H.; Daub, E.; Robinson, R.; Honek, J. F. *Biochemistry* 1997, 36, 3404; Budisa, N.; Steipe, B.; Demange, P.; Eckerskorn, C.; Kellerman, J.; Huber, R. *Eur. J. Biochem.* 1995, 230, 788), have been shown to exhibit translational activity in bacterial hosts. Incorporation of selenomethionine in place of methionine has long been known to facilitate protein structure determination by x-ray crystallography (Wei, Y.; Hendrickson, W. A.; Crouch, R. J.; Satow, Y. *Science* 1990, 249, 1398–1405).

However, only a limited number of amino acid analogues have been shown to conclusively exhibit translational activity in vivo, and the range of chemical functionality accessible via this route remains modest. These circumstances dictate a need for a systematic search for new amino acid analogues and strategies that will allow the engineering of proteins with novel chemical and physical properties.

SUMMARY OF INVENTION

The present invention seeks to overcome these and other disadvantages in the prior art by providing a novel method for incorporating amino acid analogues into polypeptides of interest in vivo by expanding the scope of amino acid analogues that are incorporated and increasing protein yields. Preferably, the production of modified polypeptides can be in a host-vector system in which a natural amino acid in the wild-type polypeptide is replaced with a selected amino acid analogue by overexpressing an aminoacyl-tRNA synthetase corresponding to the natural amino acid so replaced.

In addition, the present invention provides novel host-vector systems. The host-vector system produces an aminoacyl-tRNA synthetase in an amount in excess of the level of a naturally occurring aminoacyl-tRNA synthetase. The system also produces a polypeptide of interest in an amount in excess of the level produced by a naturally occurring gene encoding the polypeptide of interest.

Nucleic acids encoding the expression vectors, hosts, and methods of integrating a desired amino acid analogue into target polypeptides are also provided.

The invention further provides purified dihydrofolate reductase polypeptides, produced by the methods of the invention, in which the methionine residues have been replaced with homopropargylglycine (2-amino-hexynoic acid), homoallylglycine (2-amino-hexenoic acid), cis-crotylglycine (cis-2-amino-4-hexenoic acid), trans-crotylglycine (trans-2-amino-4-hexenoic acid), norleucine, 6,6,6-trifluoro-2-amino hexanoic acid, 2-amino-heptanoic acid, norvaline, o-allylserine, 2-butynylglycine, allylglycine or propargylglycine. The formation of the modified polypeptides demonstrate the ease and efficiency of the methods of the invention for incorporating amino acid analogues such as, methionine analogues, into proteins such as, dihydrofolate reductase.

Using the methods of the invention, it is possible to produce entirely new polypeptides containing amino acid analogues having unusual properties.

BRIEF DESCRIPTION OF THE FIGURES

FIG. 10 is a table detailing kinetic parameters for methionine analogues in the. ATP-$PP_i$ exchange reaction and analogue's ability to support protein biosynthesis in cultures of a conventional bacterial host supplemented with the analogues, as described in Example II, infra.

FIG. 15 is a table of the kinetic parameters for methionine analogues in the ATP-$PP_i$ exchange reaction and protein yields for bacterial cultures supplemented with the analogues, as described in Example III, infra.

FIG. 19 depicts the sequence of pQE15-MRS (SEQ ID NO.: 1).

FIG. 20 depicts the sequence of pQE15-W305F (SEQ ID NO.:2)

DETAILED DESCRIPTION OF THE INVENTION

Figure 1:
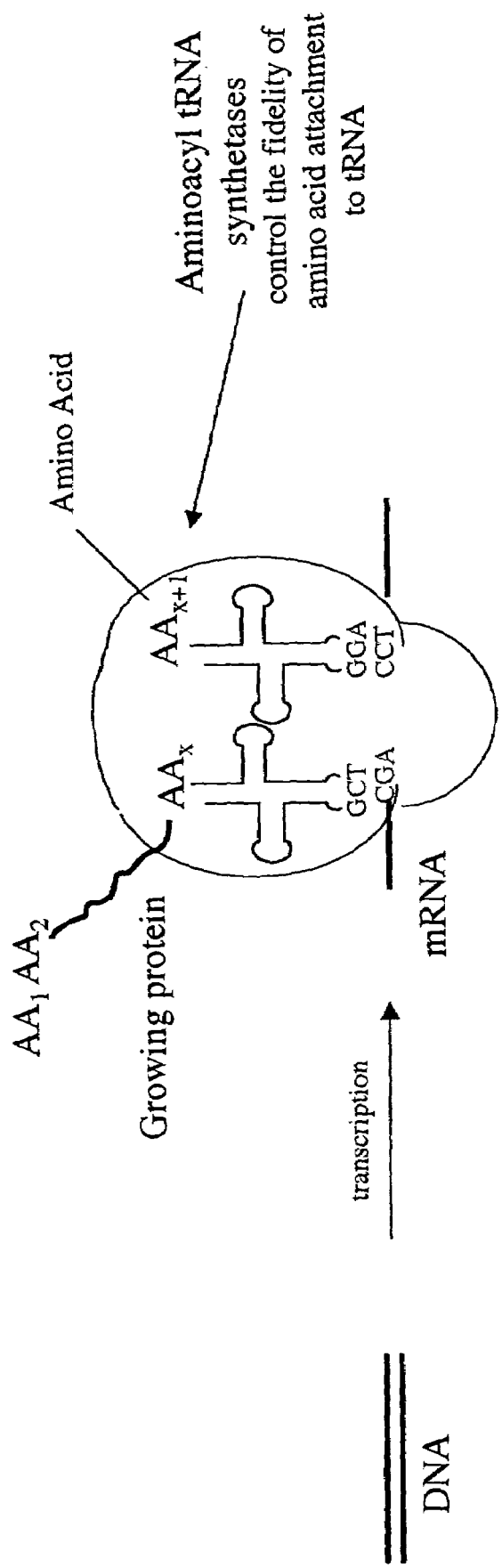
FIG. 1 depicts a schematic diagram of in vivo protein synthesis.

As used in this application, the following words or phrases have the meanings specified.

Definitions

As used herein, a polypeptide refers to a peptide or protein having natural amino acids.

As used herein, modified polypeptides are polypeptides having amino acid analogues incorporated into their amino acid sequence.

As used herein, a "natural amino acid" is one of the 20 naturally occurring amino acids, namely glycine, alanine, valine, leucine, isoleucine, serine, threonine, aspartic acid, glutamic acid, asparagine, glutamine, lysine, arginine, cysteine, methionine, phenylalanine, tyrosine, tryptophan, histidine and proline.

As used herein, the term "amino acid analogue" refers to a compound that has a structure analogue to a natural amino acid but mimics the structure and/or reactivity of a natural amino acid. This includes all amino acids but the natural 20 amino acids are referred to as amino acid analogues even if they are naturally present (e.g. hydroxyproline).

As used herein, the term "peptide" refers to a class of compounds composed of amino acids chemically bound together with amide linkages (CONH). Peptide as used herein includes oligomers of amino acids and small and large peptides, including polypeptides.

As used herein, "polypeptides" embrace all peptides and those polypeptides generally defined as proteins and also those that are glycosylated, e.g. glycoproteins.

METHODS OF THE INVENTION

The present invention is based on the discovery that incorporation of amino acid analogues into polypeptides can be improved in cells that overexpress aminoacyl-tRNA synthetases that recognize amino acid analogues as substrates. "Improvement" is defined as either increasing the scope of amino acid analogues (i.e. kinds of amino acid analogues) that are incorporated or by increasing the yield of the modified polypeptide. Overexpression of the aminoacyl-tRNA synthetase increases the level of aminoacyl-tRNA synthetase activity in the cell. The increased activity leads to an increased rate of incorporation of amino acid analogues into the growing peptide, thus the increased rate of synthesis of the polypeptides, thereby increasing the quantity of polypeptides containing amino acid analogues, i.e. modified polypeptides, produced.

In general, the methods of the invention comprises introducing into a host cell, a vector having nucleic acids encoding an aminoacyl-tRNA synthetase, and nucleic acids encoding a polypeptide of interest to produce a host-vector system. The nucleic acids, encoding the aminoacyl-tRNA synthetase, and the nucleic acids encoding the polypeptide of interest, may be located in the same or different vectors. The vectors include expression control elements which direct the production of the aminoacyl-tRNA synthetase, and the polypeptide of interest. The expression control elements (i.e. regulatory sequences) can include inducible promotors, constitutive promoters, secretion signals, enhancers, transcription terminators, and other transcriptional regulatory elements.

In the host-vector system, the production of an aminoacyl-tRNA synthetase can be controlled by a vector which comprises expression control elements that direct the production of the aminoacyl-tRNA synthetase. Preferably, the production of aminoacyl-tRNA synthetase is in an amount in excess of the level of naturally occurring aminoacyl-tRNA synthetase, such that the activity of the aminoacyl-tRNA synthetase is greater than naturally occurring levels.

In the host-vector system, the production of a polypeptide of interest can be controlled by a vector which comprises expression control elements for producing the polypeptide of interest. Preferably, the polypeptide of interest so produced is in an amount in excess of the level produced by a naturally occurring gene encoding the polypeptide of interest.

The host-vector system can be constitutively overexpressing the aminoacyl-tRNA synthetase and induced to overexpress the polypeptide of interest by contacting the host-vector system with an inducer, such as isopropyl-β-D-thiogalactopyranoside (IPTG). The host-vector system can also be induced to overexpress the aminoacyl-tRNA synthetase and/or the protein of interest by contacting the host-vector system with an inducer, such as IPTG. Other inducers include stimulation by an external stimulation such as heat shock.

Using the methods of the invention, any natural amino acid can be selected for replacement by an amino acid analogue in the polypeptide of interest. An amino acid analogue is preferably an analogue of the natural amino acid to be replaced. To replace a selected natural amino acid with an amino acid analogue in a polypeptide of interest, an appropriate corresponding aminoacyl-tRNA synthetase must be selected. For example, if an amino acid analogue will replace a methionine residue, then preferably a methionyl tRNA synthetase is selected.

The host-vector system is grown in media lacking the natural amino acid and supplemented with an amino acid analogue, thereby producing a modified polypeptide that has incorporated at least one amino acid analogue. This method is superior to existing methods as it improves the efficiency of incorporation of amino acid analogues into polypeptides of interest and increases the quantity of modified polypeptides so produced.

In an embodiment of the invention, where the host-vector system is an auxotrophic system, the host-vector system is initially grown in media which includes all essential amino acids, induced to express the polypeptide of interest, and subsequently after induction, is grown in media lacking the natural amino acid and supplemented with an amino acid analogue, thereby producing a modified polypeptide that has incorporated at least one amino acid analogue.

For example, the method of the invention can be practiced by: (1) growing the host-vector system under suitable conditions having the natural amino acid and under conditions such that the host-vector system overexpresses the aminoacyl-tRNA synthetse; (2) collecting and washing cells to remove presence of the natural amino acid; (3) resuspending the cells in media medium which lacks the natural amino acid and has an amino acid analogue; (4) inducing the expression of the polypeptide of interest; (5) growing the cells in a medium which lacks the natural amino acid and has an amino acid analogue under conditions such that the host-vector system overexpresses the aminoacyl-tRNA synthetase and the polypeptide molecule of interest; and (6) isolating the modified polypeptide of interest.

In an embodiment of the invention, the polypeptide of interest is dihydrofolate reductase, the natural amino acid is methionine, the aminoacyl-tRNA synthetase is methionyl tRNA synthetase, and the amino acid analogues of methionine are 6,6,6-trifluoromethionine, homoallyglycine, homopropargylycine, norvaline, norleucine, cis-crotylglycine, trans-crotylglycine, 2-aminoheptanoic acid, 2-butynylglycine, allylglycine, azidoalanine and azidohomoalanine.

Polypeptides of Interest

In accordance with the invention, the polypeptides may be from any source whether natural, synthetic, semi-synthetic, or recombinant. These include hormones, enzymes and protein fibers. Of these proteins, well-known examples are insulin, interferons, growth hormones, serum albumin and epidermal growth factor.

The polypeptides of interest can be those which wild-type cells cannot naturally produce. In view of the diversity of the modified polypeptides that can be produced using the methods of the invention, it is preferable that the polypeptide of interest be different from those produced by wild type cells.

Natural Amino Acids

Natural amino acids are amino acid residues that will be replaced in a polypeptide of interest by a desired amino acid analogue using the methods of the invention.

Amino acids constituting a natural amino acid residue may be selected from the 20 natural amino acids, namely glycine, alanine, valine, leucine, isoleucine, serine, threonine, aspartic acid, glutamic acid, asparagine, glutamine, lysine, arginine, cysteine, methionine, phenylalanine, tyrosine, tryptophan, histidine and proline, that constitute the amino acid sequence of a polypeptide of interest.

Aminoacyl-tRNA Synthetases

Aminoacyl-tRNA synthetases can be from any source whether natural, synthetic, semi-synthetic or recombinant (mutated or genetically engineered). Accordingly, the aminoacyl-tRNA synthetases can be from any eukaryotic or prokaryotic cell. Aminoacyl-tRNA synthetases can have originated from the same or different cell as the host cell. Types of aminoacyl-tRNA synthetases can include but are not limited to glycine, alanine, valine, leucine, isoleucine, serine, threonine, aspartic acid, glutamic acid, asparagine, glutamine, lysine, arginine, cysteine, methionine, phenylalanine, tyrosine, tryptophan, histidine and proline t-RNA synthetases. In accordance with the invention, selection of an appropriate aminoacyl-tRNA synthetase depends on the natural amino acid so selected to be replaced by an amino acid analogue. For example, if an amino acid analogue will replace methionine, then a methionyl tRNA synthetase is used.

It may be possible to use genetically engineered aminoacyl-tRNA synthetases that recognize amino acid analogues and are able to facilitate the incorporation of that amino acid analogue into a polypeptide. For example, hydroxy acids can be incorporated to form an ester linkage in place of an amide linkage of polypeptides.

Aminoacyl-tRNA synthetases can be mutated or genetically engineered to enhance properties of the enzyme to facilitate the incorporation of the amino acid analogues into polypeptides of interest. For example, the editing function of the aminoacyl-tRNA synthetases can be eliminated.

Nucleic acid sequences encoding the appropriate aminoacyl-tRNA synthetase are used in the methods of the invention.

Amino Acid Analogues

The amino acid analogues incorporated into polypeptides using the methods of this invention are different from the twenty naturally occurring counterparts in their side chain functionality. The amino acid analogue can be a close analogue of one of the twenty natural amino acids, or it can introduce a completely new functionality and chemistry. The amino acid analogue can replace an existing amino acid in a protein (substitution).

There may be a variety of amino acid analogues that can be added to a medium according to the present invention. Suitable amino acid analogues include, but are not limited to, molecules having fluorinated, electroactive, conjugated, azido, carbonyl, alkyl and unsaturated side chain functionalities. The following are representative examples of amino acid analogues:

Amino acid analogues which are modifications of natural amino acids in the side chain functionality, such that the imino groups or divalent non-carbon atoms such as oxygen or sulfur of the side chain of the natural amino acids have been substituted by methylene groups, or, alternatively, amino groups, hydroxyl groups or thiol groups have been substituted by methyl groups, olefin, or azido groups, so as to eliminate their ability to form hydrogen bonds, or to enhance their hydrophobic properties (e.g. methionine to norleucine).

Amino acid analogues which are modifications of natural amino acids in the side chain functionality, such that the methylene groups of the side chain of the natural amino acids have been substituted by imino groups or divalent non-carbon atoms or, alternatively, methyl groups have been substituted by amino groups, hydroxyl groups or thiol groups, so as to add ability to form hydrogen bonds or to reduce their hydrophobic properties (e.g. leucine to 2-aminoethylcysteine, or isolecine to o-methylthreonine).

Amino acid analogues which are modifications of natural amino acids in the side chain functionality, such that a methylene group or methyl groups have been added to the side chain of the natural amino acids to enhance their hydrophobic properties (e.g. Leucine to gamma-Methylleucine, Valine to beta-Methylvaline (t-Leucine)).

Amino acid analogues which are modifications of natural amino acids in the side chain functionality, such that a methylene groups or methyl groups of the side chain of the natural amino acids have been removed to reduce their hydrophobic properties (e.g. Isoleucine to Norvaline).

Amino acid analogues which are modifications of natural amino acids in the side chain functionality, such that the amino groups, hydroxyl groups or thiol groups of the side chain of the natural amino acids have been removed or methylated to eliminate their ability to form hydrogen bonds (e.g. Threonine to o-methylthreonine or Lysine to Norleucine).

Optical isomers of the side chains of natural amino acids (e.g. Isoleucine to Alloisoleucine);

Amino acid analogues which are modifications of natural amino acids in the side chain functionality, such that the substituent groups have been introduced as side chains to the natural amino acids (e.g. Asparagine to beta-fluoroaspargine).

Amino acid analogues which are modifications of natural amino acids where the atoms of aromatic side chains of the natural amino acids have been replaced to change the hydrophobic properties, electrical charge, fluorescent spectrum or reactivity (e.g. Phenylalanine to Pyridylalanine, Tyrosine to p-Aminophenylalanine).

Amino acid analogues which are modifications of natural amino acids where the rings of aromatic side chains of the natural amino acids have been expanded or opened so as to change hydrophobic properties, electrical charge, fluorescent spectrum or reactivity (e.g. Phenylalanine to Naphthylalanine, Phenylalanine to Pyrenylalanine).

Amino acid analogues which are modifications of the natural amino acids in which the side chains of the natural amino acids have been oxidized or reduced so as to add or remove double bonds (e.g. Alanine to Dehydroalanine, Isoleucine to Beta-methylenenorvaline).

Amino acid analogues which are modifications of proline in which the five-membered ring of proline has been opened or, additionally, substituent groups have been introduced (e.g. Proline to N-methylalanine).

Amino acid analogues which are modifications of natural amino acids in the side chain functionality, in which the second substituent group has been introduced at the alpha-position (e.g. Lysine to alpha-difluoromethyllysine).

Amino acid analogues which are combinations of one or more alterations, as described supra (e.g. Tyrosine to p-Methoxy-m-hydroxyphenylalanine).

Amino acid analogues which differ in chemical structures from natural amino acids but can serve as substrates for aminoacyl-tRNA synthetase by assuming a conformation analogous to natural amino acids when bound to this enzyme. (e.g. Isoleucine to Furanomycin)

Types of amino acid analogues of methionine are 6,6,6-trifluoromethionine, homoallyglycine, homoproparglycine, norvaline, norleucine, cis-crotylglycine, trans-crotylglycine, 2-aminoheptanoic acid, 2-butynylglycine, allylglycine, azidoalanine and azidohomoalanine.

Vectors

In accordance with the methods of the invention, suitable expression vectors which may be used include, but are not limited to, viral particles, baculovirus, phage, plasmids, phagemids, cosmids, phosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Such vectors can be chromosomal, nonchromosomal or synthetic DNA sequences.

Large numbers of suitable vectors are known to those of skill in the art, and are commercially available. The following vectors are provided by way of example; Bacterial: pQE70, pQE60, pQE-9, pQE15 (Qiagen, Valencia, Calif.), psiX174, pBluescript SK, pBluescript KS, (Stratagene, La Jolla, Calif.); pTRC99a, pKK223-3, pKK233-3, pDR540, pRIT2T (Pharmacia, Uppsala, Sweden); Eukaryotic: pWLNEO, pXT1, pSG (Stratagene, La Jolla, Calif.) pSVK3, pBPV, PMSG, pSVLSV40 (Pharmacia, Uppsala, Sweden).

A preferred vector for expression may be an autonomously replicating vector comprising a replicon that directs the replication of the nucleic acids within the appropriate host cell. The preferred vectors also include an expression control element, such as a promoter sequence, which enables transcription of the inserted sequences and can be used for regulating the expression (e.g., transcription and/or translation) of an operably linked sequence in an appropriate host cell such as *Escherichia coli*. Methods for generating vectors are well known in the art, for example, see Maniatis, T., et al., 1989 *Molecular Cloning, A Laboratory Manual*, Cold Spring Harbor Laboratory, Cold Spring Harbor, N.Y., incorporated by reference herein.

Expression control elements are known in the art and include, but are not limited to, inducible promoters, constitutive promoters, secretion signals, enhancers, transcription terminators, and other transcriptional regulatory elements. Other expression control elements that are involved in translation are known in the art, and include the Shine-Dalgarno sequence, and initiation and termination codons. The preferred vector also includes at least one selectable marker gene that encodes a gene product that confers drug resistance, such as resistance to ampicillin or tetracyline. The vector also comprises multiple endonuclease restriction sites that enable convenient insertion of exogenous DNA sequences.

The preferred vectors for generating polypeptides of interest are those compatible to prokaryotic host cells. Prokaryotic cell expression vectors are well known in the art and are available from several commercial sources. For example, a pQE vector (e.g., pQE15, available from Qiagen Corp., Valencia, Calif.) may be used to express polypeptides of interest, containing natural amino acids and modified polypeptides, including those containing amino acid analogues, in bacterial host cells.

The nucleic acids derived from a microorganism(s) may be inserted into the vector by a variety of procedures. In general, the nucleic acids can be inserted into an appropriate restriction endonuclease site(s) by procedures known in the art. Such procedures and others are deemed to be within the scope of those skilled in the art.

The nucleic acid sequence encoding the aminoacyl-tRNA synthetase or polypeptide of interest in the expression vector may be operatively linked to an appropriate expression control sequence(s) (promoter) to direct mRNA synthesis. Bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I.

Selection of the appropriate vector and its correlative promoter is well within the level of ordinary skill in the art. The expression vector may also contain a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers. Chemical or temperature sensitive promoters can be used for inducing the expression of either the aminoacyl-tRNA synthetase or the target protein.

In addition, the expression vectors preferably contain one or more selectable marker genes to provide a phenotypic trait for selection of transformed host cells, such as dihydrofolate reductase or neomycin resistance for eukaryotic cell culture, or tetracycline or ampicillin resistance in *E. coli*.

Inducers

In accordance with the methods of the invention when the expression control element is an inducible promotor, the promoter may be induced by an external stimulus, such as by adding a compound (e.g. IPTG) or by heat shocking to initiate the expression of the gene.

Level of Expression

In accordance with the methods of the invention, the production of the aminoacyl-tRNA synthetase and/or the polypeptide of interest is preferably in an amount in excess of the level (any increase that is meaningful or confers a benefit) produced by a naturally occurring gene encoding the aminoacyl-tRNA synthetase and/or the polypeptide of interest.

The increase in the level of aminoacyl-tRNA synthetase and/or the polypeptide of interest can be measured by monitoring an increase in protein expression by gel electrophoresis, western blot analysis, or other relevant methods of protein detection (Maniatis, T., et al., 1989 *Molecular Cloning, A Laboratory Manual*, Cold Spring Harbor Laboratory, Cold Spring Harbor, N.Y.).

The increase in the level of aminoacyl-tRNA synthetase can also be determined by measuring the ATP-$PP_i$ exchange activity (Mellot, P.; Mechulam, Y.; LeCorre, D.; Blanquet, S.; Fayat, G. *J. Mol. Biol.* 1989, 208, 429; Blanquet, S.; Fayat, G.; Waller, J.-P. *Eur. J. Biochem.* 1974, 44, 343; Ghosh, G.; Pelka, H.; Schulman, L. H. *Biochemistry* 1990, 29, 2220) of cell lysates.

Fusion Genes

In accordance with the methods of the invention, a fusion gene includes a sequence encoding a polypeptide of the invention operatively fused (e.g., linked) to a non-related sequence such as, for example, a tag sequence to facilitate isolation and/or purification of the expressed gene product (Kroll, D. J., et al., 1993 *DNA Cell Biol* 12:441–53). The pQE expression vectors used in this invention express proteins fused to a poly-Histidine tag that facilitates isolation and/or purification of the expressed gene.

Host Cells

In accordance with the methods of the invention, types of host cells include, but are not limited to, bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

A preferred embodiment of a host cell is an auxotroph. Auxotrophs depend upon the external environment to supply certain amino acids, for example, a methionine auxotroph depends on methionine in the growth medium for its survival. The choice of auxotroph is dependent on the amino acid that is selected to be replaced by an amino acid analogue in the target protein (e.g. if methionine is selected, then a methionine auxotroph is employed, if phenylalanine is selected, then a phenylalanine auxotroph is employed).

Suitable auxotrophs include, but are not limited to CAG18491, B834(DE3), AD494, DL41, and ML304d.

Host cells may be either wild type cells or transformants. The term "transformants" as used herein including products of transformation, transfection and transduction. Preferably, the polypeptides of interest to be produced by the cells according to the present invention are those which wild-type cells cannot produce. Thus, it is preferable that the cells to be used in the present invention be transformants.

Host-Vector Systems

The invention further discloses a host-vector system comprising a vector or vectors having nucleic acids encoding the aminoacyl-tRNA synthetase and polypeptide of interest.

The host-vector system is used to produce the polypeptides of interest. The host cell can be either prokaryotic or eukaryotic. Examples of suitable prokaryotic host cells include bacterial strains from genera such as *Escherichia, Bacillus, Pseudomonas, Streptococcus*, and *Streptomyces*. Examples of suitable eukaryotic host cells include a yeast cell, a plant cell, or an animal cell, such as a mammalian cell.

Introduction of the vectors of the present invention into an appropriate cell host is accomplished by well known methods that typically depend on the type of vector used and host system employed. For transformation of prokaryotic host cells, electroporation and salt treatment methods are typically employed, see for example, Cohen et al., 1972 *Proc Acad Sci USA* 69:2110; Maniatis, T., et al., 1989 *Molecular Cloning, A Laboratory Manual*, Cold Spring Harbor Laboratory, Cold Spring Harbor, N.Y. Transformation of vertebrate cells with vectors by electroporation, cationic lipid or salt treatment methods, is typically employed, see, for example, Graham et al., 1973 Virol 52:456; Wigler et al., 1979 *Proc Natl Acad Sci USA* 76:1373–76.

Successfully transformed host cells, i.e., cells that contain a vector of the present invention, are identified by well-known techniques. For example, cells resulting from the introduction of a vector of the present invention are selected and cloned to produce single colonies. Cells from those colonies are harvested, lysed and their nucleic acid content examined for the presence of the vector using a method such as that described by Southern, *J Mol Biol* (1975) 98:503, or Berent et al., *Biotech* (1985) 3:208, or the proteins produced from the cell are assayed via a biochemical assay or immunological method such as Western blotting.

The methods of the invention in which the cloned gene is expressed in a suitable host cell, are preferred if longer polypeptides, higher yield, or a controlled degree of amino acid analogue incorporation is desired. For example, a suitable host cell is introduced with an expression vector having the nucleotide sequence encoding the polypeptide of interest. The host cell is then cultured under conditions that permit in vivo production of the desired polypeptide, wherein one or more naturally occurring amino acids in the desired polypeptide are replaced with the amino acid analogue analogues and derivatives.

A preferred embodiment provides a host-vector system comprising the pQE15 (Qiagen, Santa Clara, Calif.) vector having a sequence encoding the the aminoacyl-tRNA synthetase and target polypeptide of invention, which is introduced along with the pREP4 (Qiagen) vector into an appropriate auxotrophic host cell such as *E. coli* methionine auxotroph CAG18491 strain, which is useful, for example, for producing a polypeptide where a selected natural amino acid is replaced with a amino acid analogue.

An embodiment of the host cells of the present invention are *Escherichia coli* and transformants thereof, and an example of the protein to be produced is dihydrofolate reductase.

Media

Suitable media for growing the host-vector systems of the invention are well known in the art, for example, see Sambrook et al., *Molecular Cloning* (1989), supra. In general, a suitable media contains all the essential nutrients for the growth of the host-vector system. The media can be supplemented with antibiotics that are selected for host-vector system.

The media may contain all 20 natural amino acids or lack a selected natural amino acid. The media may also contain an amino acid analogue in place of a selected natural amino acid.

Potential Uses of Modified Polypeptides

According to the present invention, it is now possible to create entirely new modified polypeptides, in which amino acid analogues, as well as the 20 natural amino acids are used as constituents.

Modified polypeptides can be used to prepare functional drugs, antagonistic drugs or inhibitory agents. Also, using non-natural amino acids in protein engineering expands the potential designs of polypeptides. Since such modified polypeptides are not natural, they may be less susceptible to proteolytic enzymes generally present in cells.

Introduction of amino acid analogues in polypeptides may produce modified polypeptides having a variety of side chains having highly active chemical functional groups. The reactivity of the various types of the functional groups introduced can be exploited to control protein structure and function. For example, polypeptides or proteins may be produced that have undergone site-specific phosphorylation, methylation or addition of sugar chains. It may be possible to produce modified polypeptides as derivatives analogous to specified proteins by the introduction of amino acid analogues having functional groups to form crosslinks so that cellular components which interact with the specified proteins in the cells can be detected. Modified polypeptides with incorporated fluorescent amino acid residues are useful to trace metabolic pathways in organisms or to elucidate mechanisms of biological actions. It is possible to produce modified polypeptides having amino acid analogues which differ in acid dissociation constant from natural amino acids, so as to control properties of the polypeptides that depend on the acidity in aqueous solutions.

It is possible to introduce amino acid analogues into polypeptides that will self-assemble so as to mimic viruses (e.g., coat proteins), muscle fibers (e.g., actin and myosin) or chromatin (e.g., histones) so as to create supra-molecular structures having specified functions. Additionally, the supra-molecular structures can be further modified in a biological system to create other supra-molecular structures having specified functions.

It may be possible to add amino acid analogues according to the methods of the invention to artificial feeds for silk worms that can synthesize silk with the amino acid analogues. Further, it may be possible to produce protein fibers with optical properties from modified polypeptides into which amino acid analogues have been incorporated. In this regard, modified polypeptides with amino acid analogues having functional groups to form crosslinkages can produce supra-molecular structures with silk as supporting construction. Crosslinkages of the modified polypeptides can then produce new proteinaceous structures. Into the structures thus produced, non-natural fluorescent amino acids can be introduced, e.g. to make biochips for photoenergy transduction.

ADVANTAGES OF THE INVENTION

The invention introduces a unique strategy that can be widely applied to incorporate amino acid analogues to substitute for any of the selected natural amino acid residues in polypeptides of interest. A greater range of amino acid analogues can be employed for protein synthesis. In addition, modified polypeptides produced using the methods of this invention can be produced in higher yields and with high levels of replacement of natural amino acids.

The method of this invention changes the building blocks of protein synthesis, leaving the "blueprint" encoding the proteins unchanged. The invention, therefore, permits a rapid and predictable approach to protein design and produces modified polypeptides with significantly increased yields and expansion of amino acid analogues that can serve as substrates for polypeptide synthesis.

This method of this invention is generally applicable to a large range of proteins, enzymes, and peptides, and is not limited by the size or structure of the proteins or polypeptides. Incorporation of amino acid analogues with different functionalities, such as double bonds, can be utilized for further chemical derivatization of the polypeptide of interest. Furthermore, the feasibility of incorporating amino acid analogues using in vivo methods should allow the manipulation of enzymes, signaling molecules, protein ligands, and may prove to be of broad utility in the engineering of more versatile biological assemblies.

The following examples are presented to illustrate the present invention and to assist one of ordinary skill in making and using the same. The examples are not intended in any way to otherwise limit the scope of the invention.

EXAMPLE I

This example demonstrates the selectivity of methionyl t-RNA synthetase for methionine analogues and the efficient incorporation of unsaturated methionine analogues into proteins in vivo.

Synthesis of Amino Acid Analogues

Figure 2:
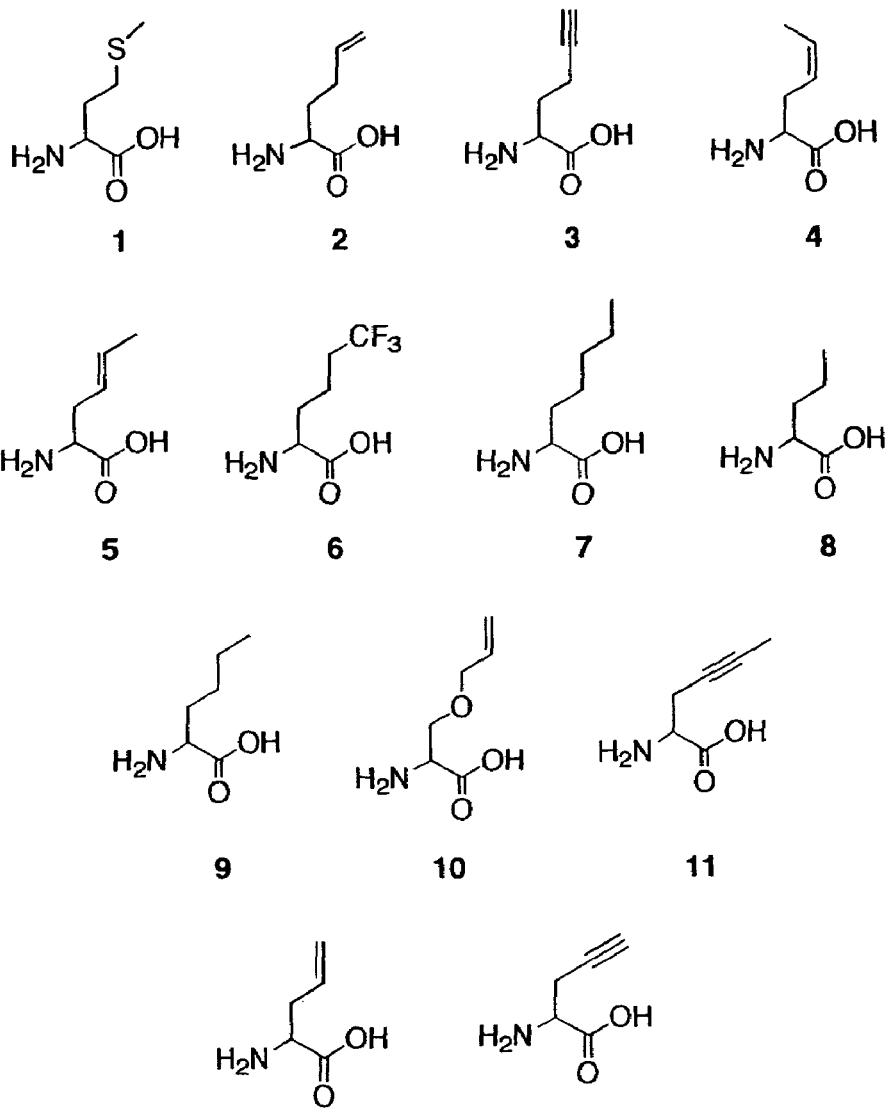
FIG. 2 depicts a set of methionine analogues (2–13), as described in Example I, infra.

Each of the analogues 2–7 and 11 (FIG. 2) was prepared by alkylation of diethyl acetamidomalonate with the appropriate alkyl tosylate followed by decarboxylation and deprotection of the amine function. This section provides information on general synthetic procedures and a detailed protocol for preparation of 2. Similar methods were used to prepare 3–7 and 11. Analogues 8, 9, 12, and 13 are available commercially (Sigma-Aldrich, St. Louis, Mo). Analogue 10 was prepared as described by Blackwell et al (H. E. Blackwell, R. H. Grubbs, *Angew. Chem.* 1998, 110, 3469–3472; *Angew. Chem. Int. Ed.* 1998, 37, 3281–3284.).

General Procedures.

Glassware was dried at 150° C. and cooled under nitrogen prior to use. Tetrahydrofuran (THF) was freshly distilled from Na/benzophenone. N,N-Dimethylformamide (DMF) was distilled and stored over BaO. Pyridine (99.8%, anhydrous, Aldrich) and other reagents and solvents were used as received. $^1$H NMR spectra were recorded on Bruker AC 200 and AMX 500 spectrometers and $^{13}$C NMR spectra were recorded on a Bruker DPX 300 spectrometer. Column chromatography was performed with silica gel 60, 230–400 mesh (EM Science); silica 60-F254 (Riedel-de Haën) was used for thin layer chromatography.

DL-2-amino-5-hexenoic acid (2)

(Drinkwater, D. J.; Smith, P. W. G. *J. Chem. Soc. C* 1971, 1305; Baldwin, J. E.; Hulme, C.; Schofield, C. J. *J. Chem. Res.* (S) 1992, 173).

3-Buten-1-ol 4-methylbenzene Sulfonate.

A solution of 3 g (42 mmol) 3-buten-1-ol in 10 mL dry pyridine was cooled in an ice bath. Tosyl chloride (7.9 g, 42 mmol), was added. After stirring for 3 h the mixture was poured into 30 mL of an ice/concentrated HCl 4/1 v/v solution, extracted with 60 mL diethyl ether and dried overnight in the freezer over MgSO$_4$. The mixture was filtered and the ether evaporated to yield 7.22 g (76%) of 3-buten-1-ol 4-methylbenzene sulfonate as a yellow oil. $^1$H NMR (CDCl$_3$): δ 2.39–2.53 (m, 2H, J=6.5 and 6.9 Hz, C$\underline{H}_2$—CH=CH$_2$; and s, 3H, C$\underline{H}_3$—Ar), 4.08 (t, J=6.5 Hz, 2H, C$\underline{H}_2$OSO$_2$), 5.09–5.15 (m, 2H, $J_Z$=10.4, $J_E$=16.6, $J_{gem}$=3.1 Hz, CH$_2$—CH=C$\underline{H}_2$), 5.57–5.82 (m, 1H, $J_Z$=10.4, $J_E$=16.6, J=6.9 Hz, CH$_2$—C$\underline{H}$=CH$_2$), 7.38 and 7.72 (d,4H, J=8.6 Hz, $\underline{Ar}$).

Acetylamino-3-butenyl-propanedioic Acid Diethyl Ester.

Diethyl acetamidomalonate, 1.56 g (6.9 mmol), was dissolved at room temperature under N$_2$ in 10 mL dry THF. Potassium tert-butoxide (0.80 g, 7 mmol), was added under vigorous stirring. The mixture was heated for 2 h at 60° C. 3-Buten-1-ol 4-methylbenzenesulfonate (1.5 g, 6.9 mmol) was added, and the mixture was heated under reflux for 2 days. The THF was removed, the residue was quenched with 10 mL 1 M HCl, and the crude product was extracted with ethyl acetate (25 mL). The ethyl acetate solution was washed twice with 25 mL water, dried over MgSO$_4$, filtered and concentrated. The crude product was purified by column chromatography (eluent cyclohexane/ethyl acetate 2/1 v/v) to yield 0.82 g (44%) of acetylamino-3-butenyl-propanedioic acid diethyl ester. $^1$H NMR (CDCl$_3$): δ 1.28 (t, 6H, J=7.2 Hz, CH$_1$-CH$_2$), 1.78–2.0 (m, 2H, J=8.3, 6.5 Hz, CH$_2$=CH—C$\underline{H}_2$—CH$_2$), 2.08 (s, 3H, CONH-C$\underline{H}_3$), 2.45 (m, 2H, J=8.3 Hz, CH$_2$=CH—CH$_2$—C$\underline{H}_2$), 4.25 (q, 4H, J=7.2 Hz, CH$_3$—C$\underline{H}_2$), 4.90–5.09 (m, 2H, $J_Z$=10.4, $J_E$=16.6, $J_{gem}$=3.2 Hz, CH$_2$—CH=C$\underline{H}_2$), 5.61–5.90 (m, 1H, $J_Z$=10.4, $J_E$=16.6, J=6.5 Hz, CH$_2$—C$\underline{H}$=CH$_2$), 6.78 (s, 1H, CONH—CH$_3$).

DL-2-amino-5-hexenoic Acid.

The diethyl ester obtained as described above was hydrolyzed to the dicarboxylate by heating under reflux for 4 h in 25 mL 10 w% NaOH. The solution was neutralized with 6 M HCl and the solvent was evaporated. The diacid was extracted with 25 mL of methanol. Following solvent evaporation, 20 mL 1M HCl was added and the solution was refluxed for 3 h. The solvent was evaporated and the product was taken up in 10 mL methanol. Propylene oxide (5 mL) was added and the mixture was stirred overnight at room temperature. The precipitate was filtered and dried, yielding DL-2-amino-5-hexenoic acid (0.47 g, 63%). The product was recrystallized from EtOH/H$_2$O 2/1 v/v (0.28 g, 60%). The $^1$H NMR data were in agreement with those of reference 16 (Hatanaka, S.-I.; Furukawa, J.; Aoki, T.; Akatsuka, H.; Nagasawa, E. *Mycoscience*, 1994, 35, 391). $^1$H NMR (D$_2$O): δ 1.78–2.0 (m, 2H, J=6.4, 6.6 Hz, CH$_2$=CH—C$\underline{H}_2$—CH$_2$), 2.08–2.20 (m, 2H, J=6.1, 6.4 Hz, CH$_2$=CH—CH$_2$—C$\underline{H}_2$), 3.75 (t, 1H, J=6.1 Hz, H$_2$N—C$\underline{H}$—COOH),4.90–5.12 (m, 2H, $J_Z$=10.5, $J_E$=16.7, $J_{gem}$=3.3 Hz, CH$_2$—CH=C$\underline{H}_2$), 5.61–5.90 (m, 1H, $J_Z$=10.5, $J_E$=16.7, J=6.6 Hz, CH$_2$—C$\underline{H}$=CH$_2$). $^{13}$C NMR (D$_2$O): δ 28.9 (CH$_2$=CH—$\underline{C}$H$_2$—CH$_2$), 29.9 (CH$_2$=CH—CH$_2$—$\underline{C}$H$_2$), 54.4 (H$_2$N—$\underline{C}$H—COOH), 116.3 (CH$_2$—CH=$\underline{C}$H$_2$), 137.3 (CH$_2$—$\underline{C}$H=CH$_2$), 174.8 ($\underline{C}$OOH).

Determination of Translational Activity

Buffers and media were prepared according to standard protocols (Sambrook, J.; Fritsch, E. F.; Maniatis, T. *Molecular Cloning: A Laboratory Manual, 2nd Ed*. Cold Spring Harbor Laboratory Press, Cold Spring Harbor, N.Y. 1989; Ausubel, F. M.; Brent, K.; Kingston, K. E.; Moore, D. D.; Scidman, J. G.; Smith, J. A.; Struhl, K. *Current Protocols in Molecular Biology*, John Wiley & Sons, NY 1995). The *E. coli* methionine auxotroph CAG18491 (λ$^-$, rph-1, metE3079.:Tn10) (obtained from the Yale *E. coli* Genetic Stock Center), was transformed with plasmids pREP4 and pQE15 (Qiagen, Valencia, Calif.), to obtain the expression host CAG 18491/pQE15/pREP4.

Protein Expression (5 mL Scale).

M9AA medium (50 mL) supplemented with 1 mM MgSO$_4$, 0.2 wt % glucose, 1 mg/L thiamine chloride and the antibiotics ampicillin (200 mg/L) and kanamycin (25 mg/L) was inoculated with 2 mL of an overnight culture of CAG18491/pQE15/pREP4. When the turbidity of the culture reached an optical density at 600 nm (OD$_{600}$) of 0.8, a.medium shift was performed. The cells were sedimented for 10 min at 3030 g at 4° C., the supernatant was removed, and the cell pellet was washed twice with 20 mL of M9 medium. Cells were resuspended in 50 mL of the M9AA medium described above, without methionine. Test tubes containing 5 mL aliquots of the resulting culture were prepared, and were supplemented with 200 μL 1 mg/mL (0.27 mM) L-methionine (1) (positive control), DL-2-amino-5-hexenoic acid (2) (0.31 mM), DL-homopropargylglycine(3) (0.31 mM), cis- or trans-DL-2-amino-4-hexenoic acid (4 or 5) (0.31 mM), DL-6,6,6-trifluoro-2-amino hexanoic acid (6) (0.22 mM), DL-2-aminoheptanoic acid (7) (0.28 mM), L-norvaline (8) (0.34 mM) or L-norleucine (9) (0.31 mM), respectively. A culture lacking methionine (or any analogue) served as the negative control. Protein expression was induced by addition of isopropyl-β-D-thiogalactopyranoside (IPTG) to a final concentration of 0.4 mM. Samples were taken every hour for 4 h, the OD$_{600}$ was measured, and the samples were sedimented. After the supernatant was decanted, the cell pellets were resuspended in 20 μL distilled H$_2$O. Protein expression was monitored by SDS polyacrylamide gel electrophoresis (12% acrylamide running gel, 12 mA, 14 h), using a normalized OD$_{600}$ of 0.2 per sample.

Protein Expression (1 L Scale)

Similar procedures were used for preparation and isolation of mDHFR from media supplemented with 1, 2 or 3. The example presented is for medium supplemented with 3. M9AA medium (100 mL) supplemented with 1 mM MgSO$_4$ 0.2w% glucose, 1 mg/L thiamine chloride and the antibiotics ampicillin (200 mg/L) and kanamycin (25 mg/L) was inoculated with *E. coli* strain CAG18491/pQE15/pREP4 and grown overnight at 37° C. This culture was used to inoculate 900 mL M9AA medium supplemented as described. The cells were grown to an $OD_{600}$ of 0.94 and the medium shift was performed as described for the small scale experiments, followed by addition of 40 mL of 1 mg/mL DL-homopropargylglycine (3). IPTG (0.4 mM) was added, and samples were taken at 1 hour intervals. $OD_{600}$ was measured, the samples were sedimented and decanted, and the cell pellets were resuspended in 20 1L distilled $H_2O$. Protein expression was monitored by SDS polyacrylamide gel electrophoresis (12% acrylamide running gel, 12 mA, 15 h).

Protein Purification

Approximately 4.5 h after induction, cells were sedimented (9,800 g, 10 min, 4° C.) and the supernatant was removed. The pellet was placed in the freezer overnight. The cells were thawed for 30 min at 37° C., 30 mL of buffer (6 M guanidine-HCl, 0.1 M $NaH_2PO_4$, 0.01 M Tris, pH 8) was added and the mixture was shaken at room temperature for 1 h. The cell debris was sedimented (15,300 g, 20 min, 4° C.) and the supernatant was subjected to immobilized metal affinity chromatography (Ni-NTA resin) according to the procedure described by Qiagen (*The Qiagen Expressionist, Purification Procedure* 7, 1992, 45). The supernatant was loaded on 10 mL of resin which was then washed with 50 mL of guanidine buffer followed by 25 mL of urea buffer (8 M urea, 0.1 M $NaH_2PO_4$ and 0.01 M Tris, pH 8). Similar urea buffers were used for three successive 25 mL washes at pH values of 6.3, 5.9 and 4.5, respectively. Target protein was obtained in washes at pH 5.9 and 4.5. These washes were combined and dialyzed (Spectra/Por membrane 1, MWCO=6–8 kDa) against running distilled water for 4 days, followed by batchwise dialysis against doubly distilled water for one day. The dialysate was lyophilized to yield 70 mg of modified mDHFR (mDHFR-Y). A similar procedure using medium supplemented with 2 yielded 8 mg of mDHFR-E. A control experiment in 2xYT medium afforded 60 mg of mDHFR. Amino acid analyses, electrospray mass spectrometry and N-terminal protein sequencing was performed on the mDHFR isolated.

Enzyme Purification and Activation Assays

The fully active, truncated form of methionyl tRNA synthetase (MetRS) was purified from overnight cultures of JM101 cells carrying the plasmid pGG3. (The plasmid, which encodes the tryptic fragment of MetRS, Ghosh, G.; Brunie, S.; Schulman, L. H. *J. Biol. Chem.* 1991, 266, 17136–17141). The enzyme was purified by size exclusion chromotography as previously described (Mellot, P.; Mechulam, Y.; LeCorre, D.; Blanquet, S.; Fayat, G. *J. Mol. Biol.* 1989, 208, 429). Activation of methionine analogues by MetRS was assayed via the amino-acid-dependent ATP-$PP_i$ exchange reaction, also as previously described (Mellot, P.; Mechulam, Y.; LeCorre, D.; Blanquet, S.; Fayat, G. *J. Mol. Biol.* 1989, 208, 429; Blanquet, S.; Fayat, G.; Waller, J.-P. *Eur. J. Biochem.* 1974, 44, 343; Ghosh, G.; Pelka, H.; Schulman, L. H. *Biochemistry* 1990, 29, 2220). The assay, which measures the $^{32}P$-radiolabeled ATP formed by the enzyme-catalyzed exchange of $^{32}P$-pyrophosphate ($PP_i$) into ATP, was conducted in 150 μl of reaction buffer (pH 7.6, 20 mM imidazole, 0.1 mM EDTA, 10 mM β-mercaptoethanol, 7 MM $MgCl_2$, 2 mM ATP, 0.1 mg/ml BSA, and 2 mM $PP_i$ (in the form of sodium pyrophosphate with a specific activity of approximately 0.18 TBq/mole)). Assays to determine if the methionine analogues 2–13 are recognized by MetRS were conducted in solutions 75 nM in enzyme and 5 mM in the L-isomer of the analogue with a reaction time of 20 minutes. Kinetic parameters for analogue 5 were obtained with an enzyme concentration of 75 nM and analogue concentrations of 100 μM to 10 mM. Parameters for methionine were obtained by using concentrations ranging from 10 μM to 1 mM. $K_m$ values for methionine matched those previously reported (Ghosh, G.; Pelka, H.; Schulman, L. H.; Brunie, S. *Biochemistry* 1991, 30, 9569), though the measured $k_{cat}$ was somewhat lower than the literature value. Aliquots of 20 μl were removed from the reaction mixture at various time points and were quenched in 0.5 ml of a solution comprising 200 mM $PP_i$, 7% w/v $HClO_4$, and 3% w/v activated charcoal. The charcoal was rinsed twice with 0.5 mL of a 10 mM $PP_i$, 0.5% $HClO_4$ solution and was then resuspended in 0.5 mL of this solution and counted via liquid scintillation methods. Kinetic constants were calculated by nonlinear regression analysis.

Computation

Single-point energy ab initio calculations (Hartree-Fock model, 6-31G* basis set) (Hehre, W. J.; Ditchfield, R.; Pople, J. A. *J. Chem. Phys.* 1972, 56, 2257; Hariharan, P. C.; Pople, J. A. *Chem. Phys. Lett.* 1972, 66, 217; Francl, M. M. et al. *J. Chem. Phys.* 1982, 77, 3654) were performed for methionine and for analogues 2, 3 and 5 with fully extended side chains. Electron density maps are shown as surfaces of electron density 0.08 electrons/$au^3$. Isopotential plots are represented as surfaces where the energy of interaction between the amino acid and a point positive charge is equal to −10 kcal/mole. Calculations were performed by using the program MacSpartan (Wavefunction, Inc., Irvine, Calif., USA).

Results and Discussion

Methionine Analogues

Methionine analogues 2–13 were investigated with respect to their capacity to support protein synthesis in *E. coli* cells depleted of methionine. Norvaline (8) and norleucine (9), allylglycine (12), and propargylglycine (13) are commercially available. Analogues 2–7 and 11 were prepared by alkylation of diethyl acetamidomalonate with the corresponding tosylates via standard procedures, and the remaining analogues were prepared as described supra. In the cases of the cis- and trans-crotylglycines (4 and 5) the tosylates were prepared in situ, and because of fast exchange of the tosyl group with chloride ion, mixtures of the chloride and the tosylate were obtained. Hydrolysis of the malonate and conversion to the amino acid had to be performed under mild acidic conditions for analogues 2, 4 and 5; treatment with 6 N HCl, or reflux in 1 N HCl for more than 5 h led to HCl addition to the double bond. In all cases the analogues were obtained as racemates and were used as such.

Protein Expression

*E. coli* strain CAG18491/pQE15/pREP4, which produces the test protein mDHFR upon induction with IPTG, was used as the expression host. The parent strain CAG18491 is dependent on methionine for growth, owing to insertion of transposon Tn10 into the metE gene, which is essential for the final step in the endogenous synthesis of methionine. Cultures were grown in minimal medium supplemented with methionine until a cell density corresponding to $OD_{600}$ 0.8–1.0 was reached. Cells were sedimented, washed and resuspended in minimal medium without methionine. Aliquots of the culture were then supplemented with one of the analogues 2–13. Protein synthesis was induced with IPTG and cell growth and protein expression were followed over a 4 h period. Expression results are presented in FIG. 3, and show clearly that analogues 2 and 3 exhibit translational activity sufficient to allow protein synthesis in the absence of methionine. Analogues 4–8 and 12–13 are not active in the assay reported here, while the known translational activity of norleucine (9) was confirmed. CAG18491/pQE15/pREP4cultures did not grow in minimal media in which methionine was replaced by 2 and 3, at the time of inoculation.

Analysis of Protein Structure

The extent of replacement of methionine by analogues 2 and 3 was determined by an amino acid analysis, N-terminal sequencing, and (for 2) $^1$H nuclear magnetic resonance spectroscopy (Table 1). Proteins containing 2 and 3 were designated mDHFR-E (alkene) and mDHFR-Y (alkyne), respectively.

TABLE 1

Protein Yield and Extent of Methionine Replacement

| Protein | Yield (mg)[a] | Replacement (%) Amino Acid Analysis | Sequencing | $^1$H NMR |
|---|---|---|---|---|
| mDHFR-E | 8 | 86 | 92 | 77 |
| mDHFR-Y | 70 | 100 | 88 | Not determined |

[a]Yield of purified protein obtained from 1 L of CAG18491/pQE15/pREP4culture grown to $OD_{600}$ = 0.94 prior to induction by addition of IPTG. The yield of mDHFR obtained from control cultures supplemented with methionine was approximately 70 mg/L.

MDHFR-E.

Figure 4:
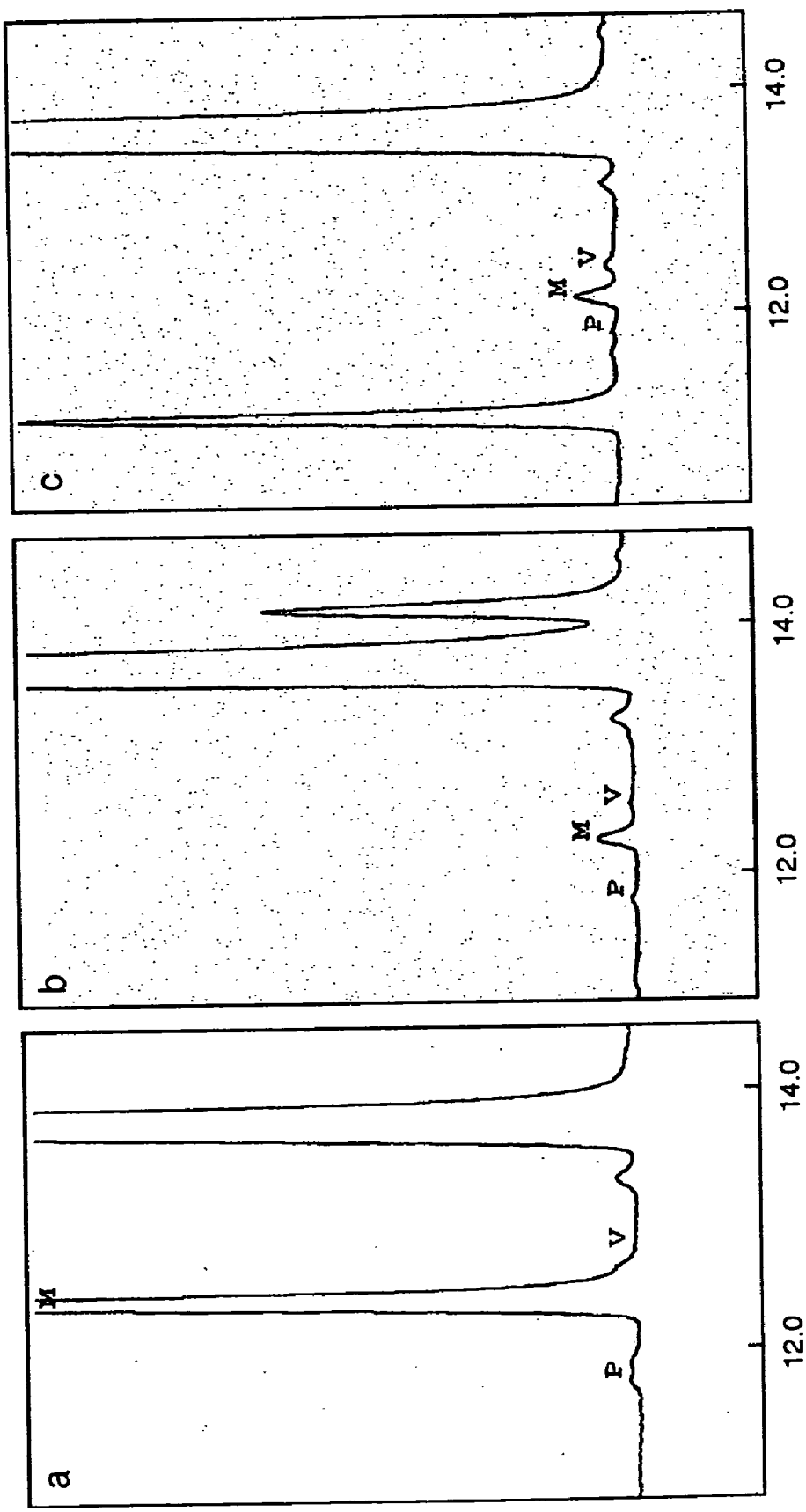
FIG. 4 shows the determination of the occupancy of the initiator site in: a). mDHFR, b). MDHFR-E (alkene) and c). mDHFR-Y(alkyne), as described in Example I, infra. Chromatograms are shown for analysis of the N-terminal residue in each of the three proteins, as determined via Edman degradation. The signals corresponding to methionine, 2 and 3 elute at 12.3, 14.3 and 11.0 min, respectively. The strong signal at 13.8 min is due to piperidylphenylthiourea, a by-product of the analysis. Signals assigned to 2 and 3 were verified by analysis of authentic samples of the analogues.

Amino acid analysis of mDHFR-E showed a methionine content of 0.5 mol % vs. the value of 3.8 mol % expected for mDHFR. Although 2 appears to be unstable under the conditions used to hydrolyze the protein for amino acid analysis, assumption that the decrement in methionine content is due to replacement by 2 affords an estimate of 86% substitution by the analogue. This estimate is consistent with the results of N-terminal sequencing of mDHFR-E (FIG. 4), which indicates 92% occupancy of the initiator site by 2. In the chromatograms shown in FIG. 4, the signal due to methionine appears at a retention time of 12.3 min, while that from 2 elutes at 14.3 min. The retention time of the signal arising from 2 was verified by analysis of an authentic sample of the analogue. Retention of the N-terminal residue in mDHFR was expected on the basis of the known correlation between the extent of methionine excision from E. coli proteins and the identity of the penultimate amino acid residue (Hirel, P. H.; Schmitter, J. M.; Dessen, P.; Fayat, G.; Blanquet, S. Proc. Natl. Acad. Sci. USA 1989, 86, 8247). Finally, direct evidence for incorporation of the alkene function of 2 was obtained from $^1$H NMR spectroscopy. The vinyl CH resonance of 2 appears at a chemical shift of 5.7 ppm in the spectrum of mDHFR-E, and can be integrated to yield an estimate of 77% replacement of methionine by the unsaturated analogue. A yield of 8 mg of mDHFR-E was obtained from a 1 L culture of CAG18491/pQE15/pREP4grown in M9AA medium supplemented with 2, compared with 70 mg obtained from a similar experiment in medium supplemented with methionine.

mDHFR-Y.

Methionine could not be detected via amino acid analysis of mDHFR-Y, suggesting quantitative replacement of methionine by the alkyne analogue 3. N-terminal sequencing (FIG. 4) indicated 88% occupancy of the initiator site by 3. $^1$H NMR analysis of mDHFR-Y was consistent with near-quantitative replacement of methionine, as the thiomethyl resonance at 2.05 ppm—which is prominent in the spectrum of mDHFR—could not be detected. New signals at 2.2–2.3 ppm—which are not observed in the spectrum of mDHFR and which correspond to signals due to the β- and ε-protons of 3—appeared in the spectrum of mDHFR-Y, but were not integrated carefully owing to overlap with neighboring resonances. The yield of mDHFR-Y obtained from M9AA medium supplemented with 3 was essentially identical to that of mDHFR isolated from media supplemented with methionine.

Enzyme Assays

Figure 5:
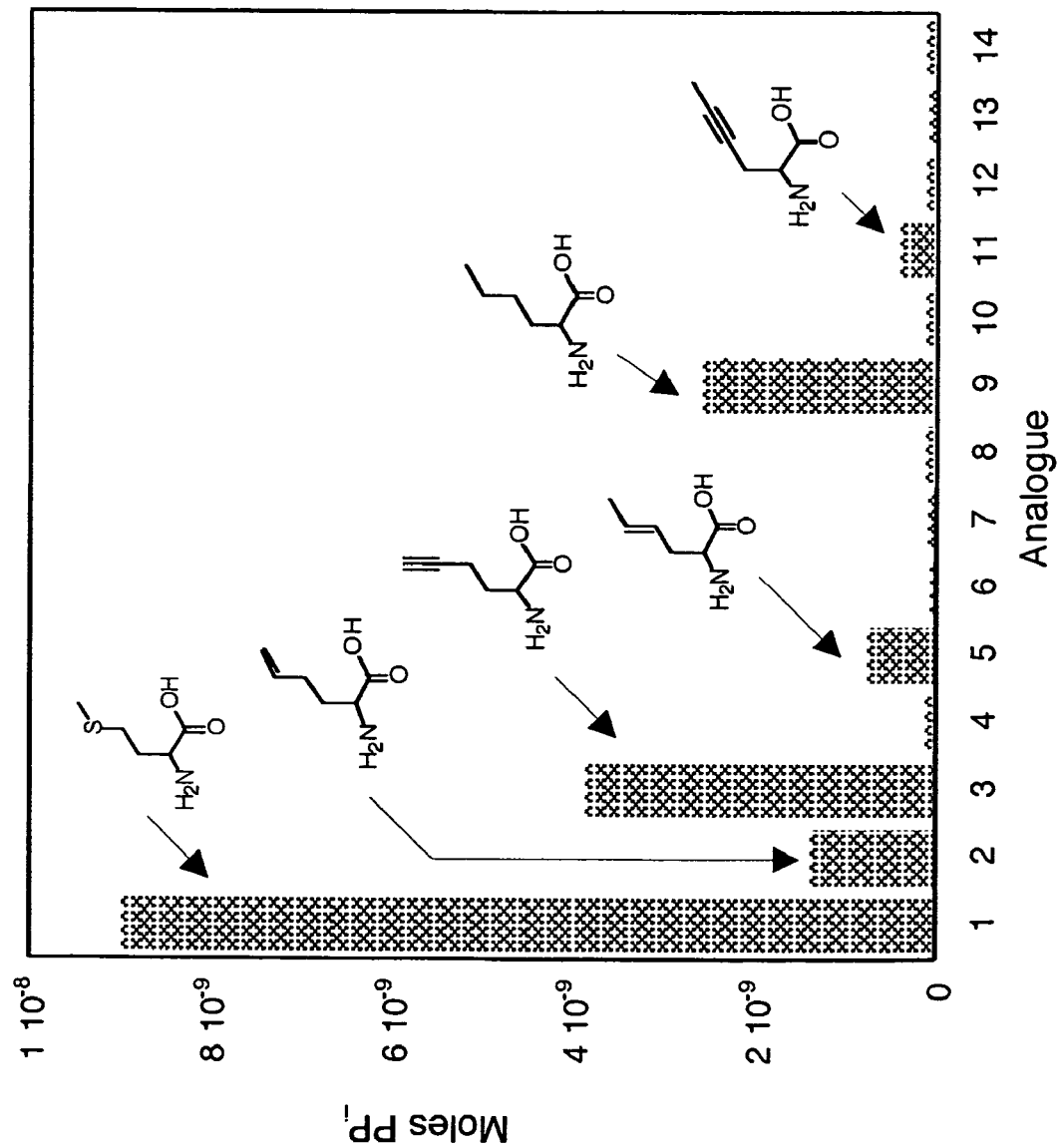
FIG. 5 depicts the activation of methionine and methionine analogues by MetRS-(Methionyl tRNA synthetase), as described in Example 1, infra. The amount of $PP_i$ exchanged in 20 minutes is shown for methionine (1) and for methionine analogues 2–13. The background (14) is given for a reaction mixture lacking both enzyme and amino acid.

The relative rates of activation of methionine and methionine analogues 2–13 by MetRS were estimated by the ATP-$PP_i$ exchange assay. The results shown in FIG. 5 illustrate the amount of $PP_i$ exchanged at a reaction time of 20 minutes under standard assay conditions (see Experimental Section). Methionine (1) is activated most efficiently by the enzyme, causing exchange of 9 nmoles of $PP_i$ over the time course of the reaction. Analogues 2 and 3 cause exchange of $PP_i$ at rates similar to that of norleucine (9), while the remaining analogues 4, 6–8, and 12–13 cause exchange of $PP_i$ at levels no higher than background (FIG. 5, lane14). The background (lane 14) is given for a reaction mixture lacking both the enzyme and the amino acid. Although analogues 5 and 11 effect very slow exchange of $PP_i$, the activation rate is apparently too low to support protein synthesis at a level that is detectable in the in vivo assays. Kinetic parameters were determined for methionine and 5 as outlined in the Experimental Section. Comparison of the $k_{cat}/K_m$ values obtained for methionine (0.54 $s^{-1}$ $\mu M^{-1}$) and 5 ($1.1 \times 10^{-4}$ $s^{-1}$ $\mu M^{-1}$) show that 5 is activated 4700-fold less efficiently than methionine by MetRS. Comparison of the $k_{cat}/K_m$ values obtained for methionine (0.54 $s^{-1}$ $\mu M^{-1}$) and 11 ($3.9 \times 10^{-5}$ $s^{-1}$ $\mu M^{-1}$) show that 11 is activated 13825-fold less efficiently than methionine by MetRS.

Discussion

A bacterial host strain (designated CAG18491/pQE15/pREP4) suitable for testing the translational activity of methionine analogues 2–8 and 10–13 was prepared by transformation of E. coli strain CAG18491, a methionine auxotroph, with the repressor plasmid pREP4 and the expression plasmid pQE 15. pQE 15 encodes mouse dihydrofolate reductase (mDHFR) under control of a bacteriophage T5 promoter, and appends to mDHFR an N-terminal hexahistidine sequence that facilitates purification of the protein by immobilized metal affinity chromatography. mDHFR contains eight methionine residues, each a potential site for substitution by analogues 2–8 and 10–13. The translational activity of each analogue was assayed on the basis of its capacity to support synthesis of mDHFR in cultures of CAG18491/pQE15/pREP4 that had been depleted of methionine. In those instances in which the test protein was detected by gel electrophoresis (i.e., for 2 and 3), the modified mDHFR was purified and analyzed to determine the extent of methionine replacement by the analogue.

Figure 3:
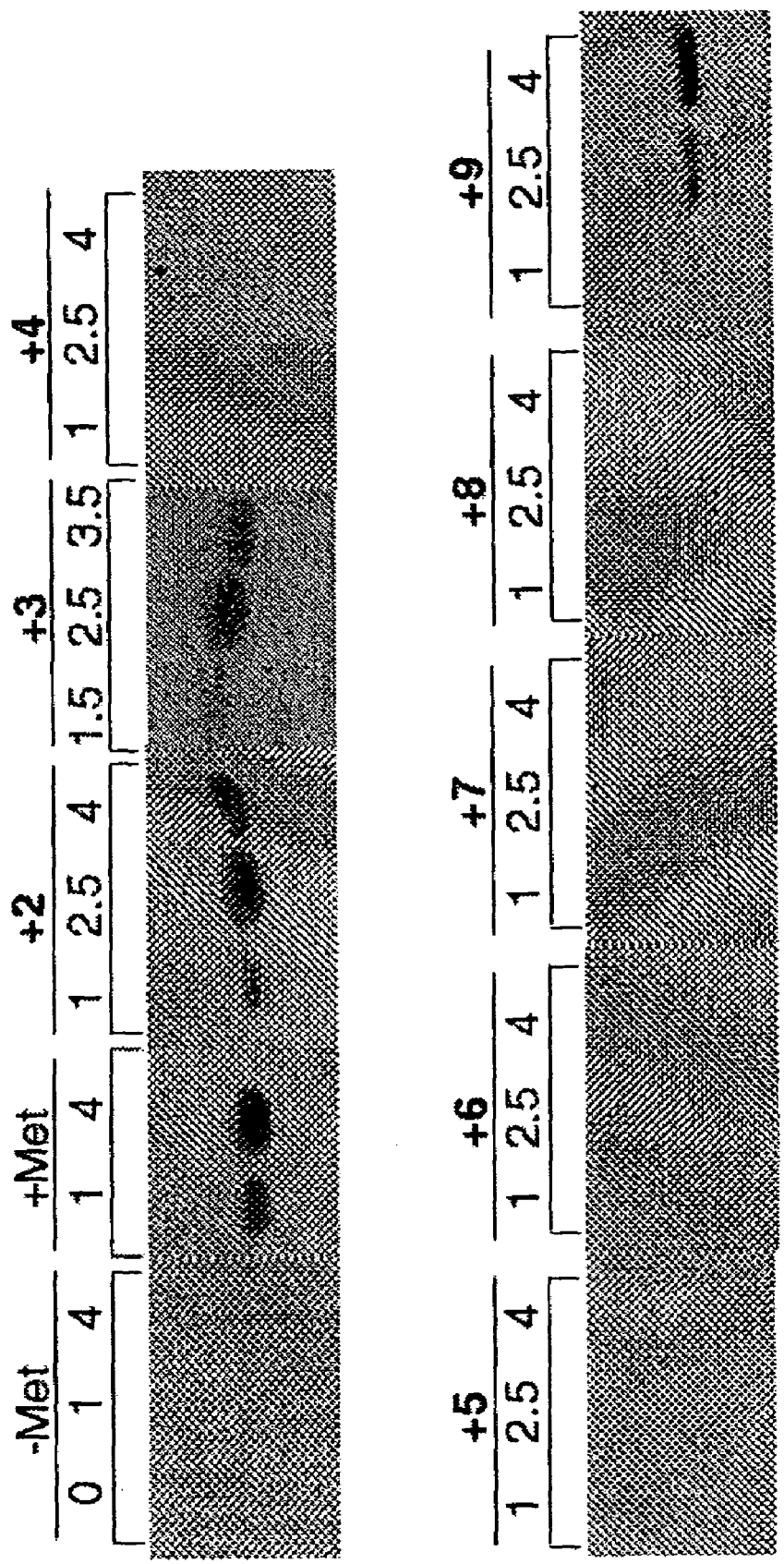
FIG. 3 illustrates the SDS-PAGE analysis of mDHFR synthesis by *E. coli* strain CAG18491/pREP4/pQE15, as described in Example I, infra. Cultures were supplemented with methionine or with one of the analogues 2–9, as indicated. Each lane is identified in terms of the time of analysis subsequent to addition of the inducer IPTG. MDHFR is visualized by staining with Coomassie Brilliant Blue. The target protein can be detected only in cultures supplemented with methionine or with analogues 2, 3, or 9, respectively.

The results of the in vivo assays illustrated in FIG. 3 show clearly that homoallylglycine (2) and homopropargylglycine (3) serve effectively as methionine surrogates in bacterial protein synthesis. In contrast, analogues 4–8 and 10–13 do not support measurable levels of protein synthesis in bacterial cultures depleted of methionine. It is highly unlikely that recognition by the elongation factors of the ribosome or transport into the cell are the limiting factors for incorporation of these analogues. The ribosome is remarkably permissive toward amino acid analogues with widely varying chemical functionality, as has been demonstrated by the numerous analogues incorporated into proteins in in vitro translation experiments (Cornish, V. W.; Mendel, D.; Schultz, P. G. *Angew. Chem. Int. Ed. Engl.* 1995, 34, 621; Robertson, S. A.; Ellman, J. A.; Schultz, P. G. *J. Am. Chem. Soc.* 1991, 113, 2722; Noren, C. J.; Anthony-Cahill, S. J.; Griffith, M. C.; Schultz, P. G. *Science* 1989, 244, 182; Bain, J. D.; Glabe, C. G.; Dix, T. A.; Chamberlin, A. R. *J. Am. Chem. Soc.* 1989, 111, 8013; Bain, J. D. et al. *Nature* 1992, 356, 537; Gallivan, J. P.; Lester, H. A.; Dougherty, D. A. *Chem. Biol.* 1997, 4, 740; Turcatti, et al. *J. Biol. Chem.* 1996, 271, 19991; Nowak, M. W. et al. *Science,* 1995, 268, 439; Saks, M. E. et al. *J. Biol. Chem.* 1996, 271, 23169; Hohsaka, T. et al. *J. Am. Chem. Soc.* 1999, 121, 34).

Transport of several analogues into the cell is indicated by a number of literature reports. Analogue 4 is an antagonist for methionine, inhibiting the growth of *E. coli* cells (Skinner, C. G.; Edelson, J.; Shive, W. *J. Am. Chem. Soc.* 1961, 83, 2281); 5 has been incorporated into proteins in *E. coli* cells with appropriately engineered MetRS activity; and 8 replaces leucine in human hemoglobin expressed in *E. coli* (Apostol, I.; Levine, J.; Lippincott, J.; Leach, J.; Hess, E.; Glascock, C. B.; Weickert, M. J.; Blackmore, R. *J. Biol. Chem.* 1997, 272, 28980). Although there is no similar evidence reported for analogues 6 and 7, the fact that trifluoromethionine and ethionine are incorporated into proteins expressed in *E. coli* (Hendrickson, W. A.; Horton, J. R.; Lemaster, D. M. *EMBO J.* 1990, 9, 1665; Boles, J. O. et al *Nature Struct. Biol.* 1994, 1, 283; Cowie, D. B.; Cohen, G. N.; Bolton, E. T.; de Robichon-Szulmajster, H. *Biochim. Biophys. Acta* 1959, 34, 39; Duewel, H.; Daub, E.; Robinson, R.; Honek, J. F. *Biochemistry* 1997, 36, 3404; Budisa, N.; Steipe, B.; Demange, P.; Eckerskorn, C.; Kellerman, J.; Huber, R. *Eur. J. Biochem.* 1995, 230, 788) suggests that neither the trifluoromethyl group nor the longer side chain will inhibit transport of analogues 6 and 7 into *E. coli* cells.

The results of the in vitro enzyme assays shown in FIG. 5 are consistent with the in vivo results, as the analogues that support the highest rates of $PP_i$ exchange also support protein synthesis in the absence of methionine. Although the in vitro results indicate that 5 and 11 are recognized by MetRS, comparison of the $k_{cat}/K_m$ values of methionine and 5 and 11, demonstrate that 5 is activated 4700-fold and 11 13825-fold less efficiently than methionine; thus it is not surprising that neither 5 or 11 support measurable protein synthesis in the in vivo experiments. Consideration of the in vivo and in vitro results, along with the reports cited earlier, suggests that transport is not limiting and that analogue incorporation is controlled by the MetRS.

Although the crystal structure of an active tryptic fragment of the *E. coli* MetRS (complexed with ATP) has been reported (Brunie, S.; Zelwer, C.; Risler, J. L. *J. Mol. Biol.* 1990, 216, 411; Mechulam, Y.; Schmitt, E.; Maveyraud, L.; Zelwer, C.; Nureki, O.; Yokoyama, S.; Konno, M.; Blanquet, S. *J. Mol. Biol.* 1999, 294, 1287–1297), the corresponding structure with bound methionine is not yet available. Inferences concerning the mechanism of methionine (or analogue) recognition by MetRS have heretofore been made indirectly, on the basis of sequence comparison and site-directed mutagenesis (Ghosh, G.; Pelka, H.; Schulman, L. H.; Brunie, S. *Biochemistry* 1991, 30, 9569; Fourmy, D.; Mechulam, Y.; Brunie, S.; Blanquet, S.; Fayat, G. FEBS Lett. 1991, 292, 259; Kim, H. Y.; Ghosh, G.; Schulman, L. H.; Brunie, S.; Jakubowski, H. *Proc. Natl. Acad. Sci. USA* 1993, 90, 11553).

Figure 6:
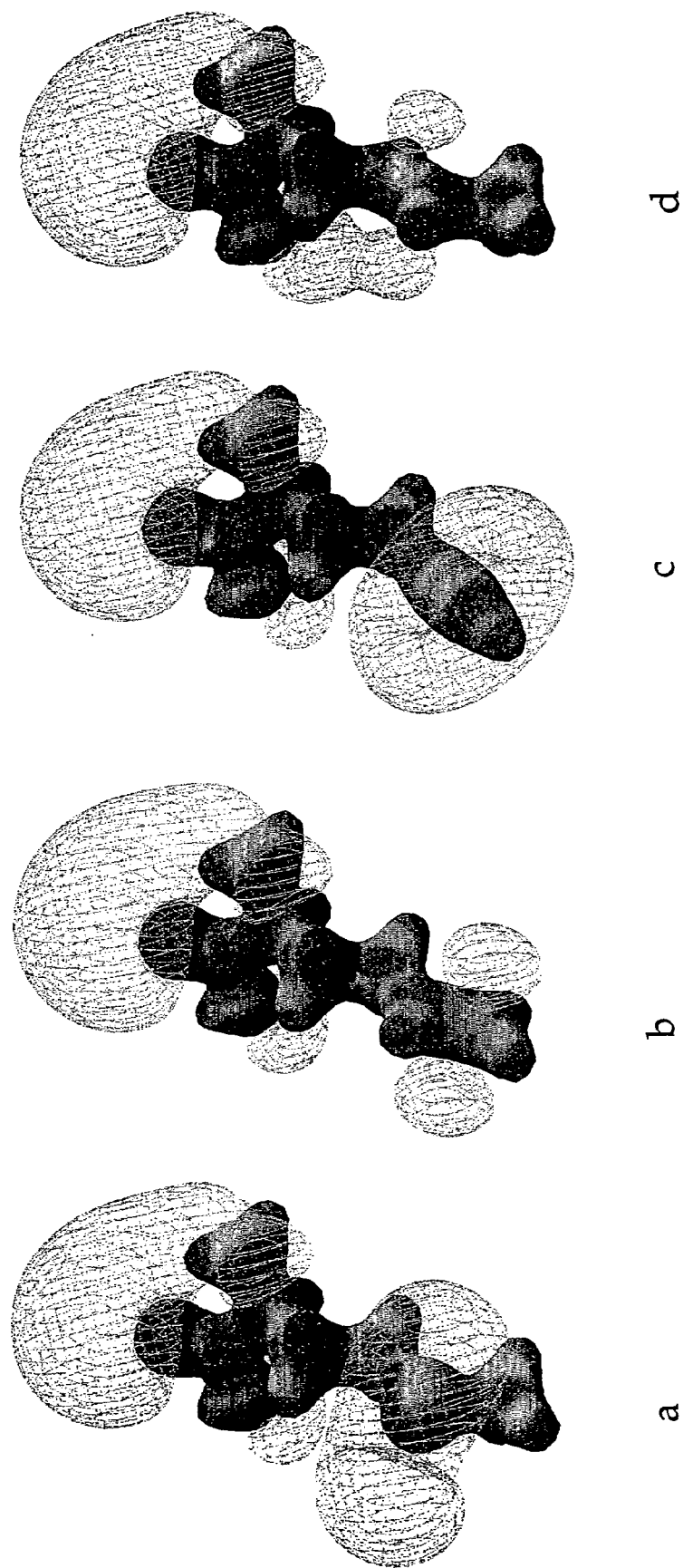
FIG. 6 illustrates the electron density maps (colored surfaces) and negative isopotential surfaces (meshes) for methionine (a) and for analogues 2, 3 and 5 (b–d, respectively), as described in Example I, infra. The electron density maps indicate electron-rich (red) and electron-poor (blue) regions of each molecule. For simplicity, the amino acid form is shown; this avoids representation of the highly extended isopotential surface of the carboxylate anion of the zwitterion and facilitates comparison of side-chain electronic structure.

FIG. 6 compares the equipotential surfaces calculated for methionine and for analogues 2, 3 and 5. That 2 might serve as a substrate for the methionyl-tRNA synthetase is not surprising, given the similar geometries accessible to 1 and 2, the availability of π-electrons near the side-chain terminus of 2, and the known translational activity of norcleucine (9), the saturated analogue of 2. The high translational activity observed for 3, (i.e. near-quantitative replacement of methionine without loss of protein yield), was not anticipated, since the colinearity of side-chain carbons 4–6 imposes on 3 a geometry substantially different from that of methionine. However, the electron density associated with the triple bond of 3 is positioned similarly to that of the thioether of the natural substrate, despite the differences in side-chain geometry. Furthermore, given the important roles assigned to residues Phe197 and Trp305 in the *E. coli* methionyl-tRNA synthetase (Ghosh, G.; Pelka, H.; Schulman, L. H.; Brunie, S. *Biochemistry* 1991, 30, 9569; Fourmy, D.; Mechulam, Y.; Brunie, S.; Blanquet, S.; Fayat, G. *FEBS Lett.* 1991, 292, 259; Kim, H. Y.; Ghosh, G.; Schulman, L. H.; Brunie, S.; Jakubowski, H. *Proc. Natl. Acad. Sci. USA* 1993, 90, 11553), alkynyl C—H/π contacts (Steiner, T.; Starikov, E. B.; Amado, A. M.; Teixeira-Dias, J. J. C. *J. Chem. Soc. Perk. Trans.* 2, 1995, 7, 1321) and the polarizability of the unsaturated side chain may also play significant roles in recognition of 3 by the enzyme. FIG. 6 also compares the geometries of 1 and 5, the latter an analogue neither recognized efficiently by the MetRS in vitro nor translationally active in vivo. Although the geometries of 1 and 5 appear similar in the representation shown, the fixed planarity of the $C_4$–$C_5$ bond may preclude the side-chain conformation required for efficient recognition of 5 by MetRS. Appropriate engineering of the MetRS activities of *E. coli* imparts translational activity to 5.

In conclusion, a set of twelve methionine analogues was assayed for translational activity in *Escherichia coli*. Norvaline and norleucine, which are commercially available, were assayed along with homoallylglycine (2), homopropargylglycine (3), cis-crotylglycine (4), trans-crotylglycine (5), 6,6,6-trifluoro-2-aminohexanoic acid (6) and 2-aminoheptanoic acid (7) and 2-butynylglycine (11), each of which was prepared by alkylation of diethyl acetamidomalonate with the appropriate tosylate, followed by hydrolysis. The other analogues were commercially available or prepared as described supra. The *E. coli* methionine auxotroph CAG18491, transformed with plasmids pREP4 and pQE15, was used as the expression host, and translational activity was assayed by determination of the capacity of the analogue to support synthesis of the test protein dihydrofolate reductase (mDHFR) in the absence of added methionine.

The importance of amino acid side chain length was illustrated by the fact that neither norvaline (8) nor 7 showed translational activity, in contrast to norleucine (9), which does support protein synthesis under the assay conditions. The internal alkene functions of 4 and 5 prevented incorporation of these analogues into test protein, and the fluorinated analogue 6 and 10–13 yielded no evidence of translational activity. The terminally-unsaturated compounds 2 and 3, however, proved to be excellent methionine surrogates: $^1H$ NMR spectroscopy, amino acid analysis and N-terminal sequencing indicated ca 85% substitution of methionine by 2, while 3 showed 90–100% replacement. Both analogues also function efficiently in the initiation step of protein synthesis, as shown by their near-quantitative occupancy of the N-terminal amino acid site in mDHFR. Enzyme kinetics assays were conducted to determine the rate of activation of each of the methionine analogues by methionyl tRNA synthetase (MetRS); results of the in vitro assays corroborate the in vivo incorporation results, suggesting that success or failure of analogue incorporation in vivo is controlled by MetRS.

EXAMPLE II

This example demonstrates the expansion of the scope of methionine analogues for incorporation into proteins in vivo by altering the methionyl-tRNA synthetase activity of a bacterial expression host.

The relative rates of activation of methionine and methionine analogues 2–13 (FIG. 2) by MetRS were characterized in vitro by the ATP-PP$_i$ exchange assay. The fully active, truncated form of MetRS was purified from overnight cultures of JM101 cells carrying the plasmid pGG3. The enzyme was purified by size exclusion chromatography as previously described (P. Mellot, Y. Mechulam, D. LeCorre, S. Blanquet, G. Fayat, *J. Mol. Biol.* 1989, 208, 429–443). Activation of methionine analogues by MetRS was assayed at 25° C. via the amino acid-dependent ATP-PP$_i$ exchange reaction, also as described in Example I (G. Ghosh, H. Pelka, L. H. Schulman, *Biochemistry* 1990, 29, 2220–2225). Assays to determine if the methionine analogues 2–13 were recognized by MetRS were conducted in solutions 75 nM in enzyme and 5 mM in the L-isomer of the analogue with a reaction time of 20 minutes. Kinetic parameters for analogue 5 were obtained with an enzyme concentration of 50 nM and analogue concentrations of 100 µM to 10 mM. Kinetic parameters for analogue 11 were determined using an enzyme concentration of 50 nM and analogue concentrations ranging from 750 µM to 20 mM. Kinetic parameters for analogues 4, 7, 8, and 12 were obtained with an enzyme concentration of 50 or 75 nM and analogue concentrations ranging from 5 to 70 mM. Parameters for methionine were obtained by using concentrations ranging from 10 µM to 1 mM. $K_m$ values for methionine were similar to those previously reported (24±2 µM), though the measured $k_{cat}$ was somewhat lower than the literature value (13.5 s$^{-1}$) (H. Y. Kim, G. Ghosh, L. H. Schulman, S. Brunie, H. Jakubowski, *Proc. Natl. Acad. Sci. USA* 1993, 90, 11553–11557). Kinetic constants were calculated by non-linear regression analysis.

FIG. 5 demonstrates that analogues 2 and 3 are activated by MetRS, as anticipated on the basis of the in vivo experiments (as described in Example I, infra; J. C. M. van Hest, D. A. Tirrell, *FEBS Lett.* 1998, 428, 68–70), although they cause exchange of PP$_i$ at rates several-fold lower than methionine. Analogue 4 does not cause measurable exchange of PP$_i$ by MetRS in vitro, which was expected since neither 4 nor 5 were indicated to be translationally active in vivo.

Analogues 5 and 11, however, were activated by MetRS, causing slow exchange of PP$_i$ under the assay conditions used herein. Table 2 shows the $k_{cat}/K_m$ values obtained for methionine, 2, 3, 5, 9, and 11. Given that $k_{cat}/K_m$ for 5 is 4700-fold and that for 11 is 13825-fold lower than that for methionine (as described in Example I, infra), it is not surprising that neither 5 or 11 support measurable protein synthesis within the time frame of the in vivo experiments.

These results suggest that increasing the MetRS activity of the expression host might allow efficient protein synthesis in cultures supplemented with 5 or 11. This strategy was not employed previously for incorporating amino acid analogues into proteins in vivo, but reports of in vivo misacylation of tRNA substrates by overexpressed aminoacyl-tRNA synthetase supported the viability of the approach (S. Li, N. V. Kumar, U. Varshney, U. L. RajBhandary, *J. Biol.*

*Chem.* 1996, 271, 1022–1028; J. M. Sherman, M. J. Rogers, D. Soll, *Nuc. Acids. Res.* 1992, 20, 2847–2852; U. Varshney, U. L. RajBhandary, *J. Bacteriol.* 1992, 174, 7819–7826; R. Swanson, P. Hoben, M. Sumner-Smith, H. Uemura, L. Watson, D. Soll, *Science* 1988, 242, 1548–1551).

TABLE 2

$k_{cat}/K_m$ values obtained for methionine, 2, 3, 5, 9, and 11

| Analogue | $K_m$ (µM) | $k_{cat}$ (s$^{-1}$) | $k_{cat}/K_m$ (s$^{-1}$µM$^{-1}$) | Protein Yield, mg/L |
|---|---|---|---|---|
| 1 | 24.3 ± 2 | 13.3 ± 0.2 | 5.47 × 10$^{-1}$ | 35 |
| 3 | 2415 ± 170 | 2.60 ± 0.3 | 1.08 × 10$^{-3}$ | 35 |
| 9 | 4120 ± 900 | 2.15 ± 0.6 | 5.22 × 10$^{-4}$ | 20 |
| 2 | 4555 ± 200 | 1.35 ± 0.1 | 2.96 × 10$^{-4}$ | 10 |
| 5 | 15,675 ± 250 | 1.82 ± 0.6 | 1.16 × 10$^{-4}$ | 0 |
| 11 | 38,650 ± 2000 | 1.51 ± 0.5 | 3.91 × 10$^{-5}$ | 0 |

Generation of Host-Vector System

A bacterial host capable of overexpressing MetRS was produced by transforming *E. coli* strains B834(DE3) (Novagen, Inc., Madison, Wis., USA), a methionine auxotroph, with repressor plasmid pREP4 and expression plasmid pQE15-MRS (FIG. 19) (SEQ ID NO.: 1). A gene encoding a mutant MetRS was removed from plasmid pBSM547W305F (D. Fourmy, Y. Mechulam, S. Brunie, S. Blanquet, G. Fayat, *FEBS Lett.* 1991, 292, 259–263) by treatment with restriction enzymes Sac I and Kpn I. The Sac I/Kpn I fragment (2450 bp) was ligated into the cloning vector pUC19-Nhelink, which was constructed to permit the cohesive ends of the mutant MetRS gene to be changed to Nhe I. The MetRS gene with Nhe I cohesive ends was then ligated into the unique Nhe I site of the plasmid pQE15 (Qiagen, Inc., Santa Clarita, Calif., USA) to yield plasmid pQE15-W305F (FIG. 20) (SEQ ID NO.: 2). Transformation of pQE15-W305F (SEQ ID NO.: 2) into a recA positive cell strain resulted in genetic recombination of the mutant MetRS gene with the chromosomal copy of the wild-type MetRS gene, yielding plasmid pQE15-MRS (SEQ ID NO.: 1).

Expression plasmid pQE15-MRS (SEQ ID NO.: 1) and repressor plasmid pREP4 were transformed into the expression host B834(DE3) to yield B834(DE3)/pQE15-MRS/pREP4. Plasmid DNA from all B834(DE3)/pQE15-MRS/pREP4 cultures used for protein expression experiments was sequenced to confirm that it encoded wild-type MetRS. The expression plasmid pQE15-MRS (SEQ ID NO.: 1) encodes MetRS under control of the *E. coli* promoter metG p1 (Genbank accession number X55791) (F. Dardel, M. Panvert, G. Fayat, *Mol. Gen. Genet.* 1990, 223, 121–133) as well as the target protein murine dihydrofolate reductase (mDHFR) under control of a bacteriophage T5 promoter. The expression plasmid also encodes an N-terminal hexahistidine sequence for MDHFR which permits purification of the target protein by immobilized metal chelate affinity chromatography (*The Qiagen Expressionist,* 1992, p. 45). Furthermore, mDHFR contains 8 methionine residues which can be replaced by methionine analogues. A control bacterial host, which produces only mDHFR and normal cellular levels of MetRS, was prepared by transforming B834(DE3) with pREP4 and pQE15.

Similarly, a bacterial host capable of overexpressing MetRS was produced by transforming *E. coli* strains CAG18491 (Novagen, Inc., Madison, Wis., USA), a methionine auxotroph, with repressor plasmid pREP4 and expression plasmid pQE15-MRS, as described for the B834

(DE3) strain. A control bacterial host, which produces only mDHFR and normal cellular levels of MetRS, was prepared by transforming CAG18491 with pREP4 and pQE15.

Methionine analogues 2–13 were tested for translational activity in both bacterial hosts. Methionine analogues were synthesized via alkylation of diethylacetamidomalonate, as previously described (As described in Example I, infra; J. C. M. van Hest, D. A. Tirrell, *FEBS Lett.* 1998, 428, 68–70). Cultures of B834(DE3)/pQE15-MRS/pREP4 or B834 (DE3)/pQE15/pREP4 or CAG18491/pQE15-MRS/pREP4 or CAG18491/pQE15/pREP4 in M9AA media were grown to an optical density of 0.90, and the cells were sedimented by centrifugation. The M9AA medium was prepared by supplementing sterile M9 medium with 60 mg/ml of each of the amino acids, 1 mM $MgSO_4$, 0.2 wt % glucose, 1 mg/ml thiamine chloride, and 1 mg/ml calcium chloride. The antibiotics ampicillin and kanamycin were added at concentrations of 200 mg/ml and 35 mg/l, respectively.

Cells were washed three times with M9 salts and resuspended to an optical density of 0.90 in M9 test media containing 19 amino acids plus 1) neither methionine nor analogue (negative control); 2) methionine (60 mg/liter, positive control); or 3) an analogue of interest (60 mg/liter). To test the effect of increasing the level of supplementation of the analogues, a set of experiments was also conducted in which the medium was supplemented with 500 mg/liter of methionine or the amino acid analogue. Expression of mDHFR was induced by addition of 0.4 mM isopropyl β-D-thiogalactopyranoside (IPTG), and protein synthesis was monitored after 4.5 hours. Expression of mDHFR was monitored by SDS-polyacrylamide gel electrophoresis (SDS-PAGE); accumulation of target protein was taken as evidence for translational activity of the methionine analogue.

For cultures supplemented with amino acids at 60 mg/liter, the target protein was not observed in the negative control culture of B834(DE3)/pQE15/pREP4, CAG18491/pQE15/pREP4 or in cultures supplemented with Ccg (4), 6,6,6-trifluoro-2-aminohexanoic acid (6), 2-aminoheptanoic acid (7), norvaline (8) o-allylserine (10), allylgylcine (12) or propargylglycine (13). In contrast, mDHFR was detected in both bacterial host cultures supplemented with methionine (1), Hag (2), Hpg (3), and norleucine (9), as indicated by the appearance of a protein band at the position expected for mDHFR in SDS-PAGE.

Figure 7:
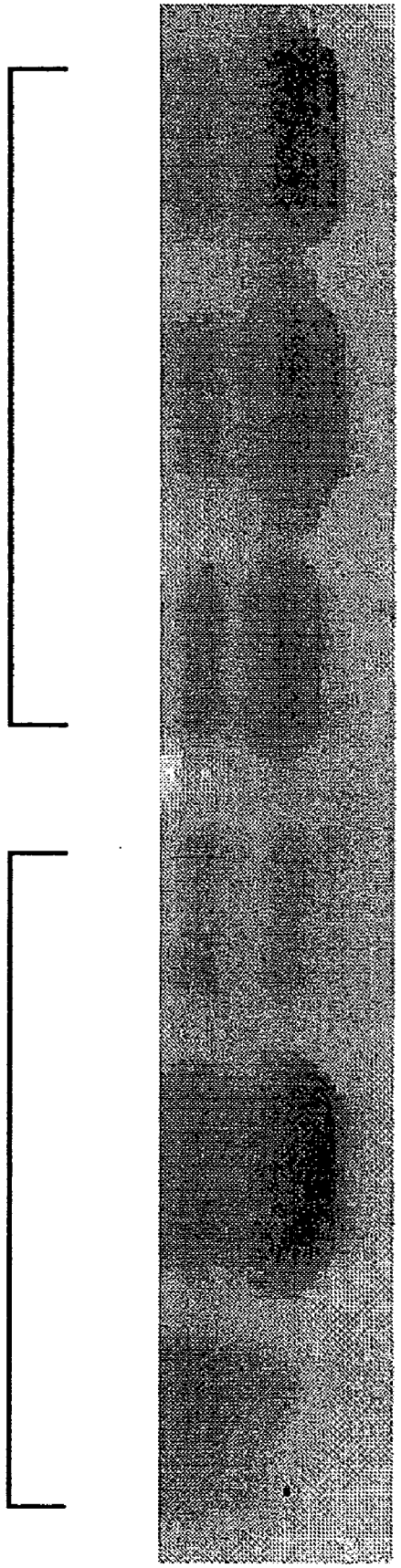
FIG. 7 shows the SDS-PAGE analysis of mDHFR synthesis by *E. coli* strains B834(DE3)/pQE15/pREP4 (designated pQE15) and B834(DE3)/pQE15-MRS/pREP4 (designated pQE15-MRS), as described. in Example II, infra. Cultures (M9+19AA) were supplemented with nothing (−Met), methionine (Met) or trans-crotylglycine (60 mg/L) (Tcg), as indicated.

For the negative control cultures and for cultures supplemented with Tcg however, the behavior of the bacterial hosts differed, as shown in FIG. 7. mDHFR was not detected in the B834(DE3)/pQE15/pREP4 culture supplemented with Tcg, while strong induction of mDHFR was observed for B834 (DE3)/pQE15-MRS/pREP4 under the same conditions. Even the unsupplemented control culture of B834(DE3)/pQE15-MRS/pREP4 shows evidence of mDHFR synthesis, suggesting that introduction of pQE15-MRS (SEQ ID NO.: 1) does indeed increase the rate of activation of methionine in the modified host.

B834(DE3)/pQE15-MRS/pREP4 cells, which overexpress MetRS, have sufficient MetRS activity to synthesize measurable levels of protein from the very low intracellular levels of methionine in the negative control culture. Interestingly, aminoacyl-tRNA synthetase overexpression is induced by amino acid starvation in some gram-positive bacteria, presumably to permit continued protein synthesis (D. Luo, J. Leautey, M. Grunberg-Manago, H. Putzer, *J. Bacteriol.* 1997, 179, 2472–2478). B834(DE3)/pQE15/pREP4 cultures, which lack the increased MetRS activity, do not show background expression of protein in negative control cultures.

Figure 8:
FIG. 8 depicts the SDS-PAGE analysis of DHFR synthesis by *E. coli* strains CAG18491/pQE15/pREP4 and CAG18491/pQE15-MRS/pREP4, as described in Example II, infra. Cultures (M9+19AA) were supplemented with nothing (−Met), methionine (+Met), or 2-butynylglycine (60 mg/L) (+2bg), as indicated.

Similar results were observed for the CAG18491/pQE15/pREP4 and CAG18491/pQE15-MRS/pREP4 cultures supplemented with 11 (FIG. 8). While mDHFR was not detected in the CAG18491/pQE15/pREP4 cultures supplemented with 11, strong induction of nDHFR was observed for CAG18491/pQE15-MRS/pREP4 under the same conditions. The unsupplemented control culture of CAG18491/pQE15-MRS/pREP4 showed little evidence of mDHFR synthesis, which may be due to lower levels of MetRS activity in these cell strains versus that in the B834(DE3)/pQE15-MRS/pREP4.

Figure 9:
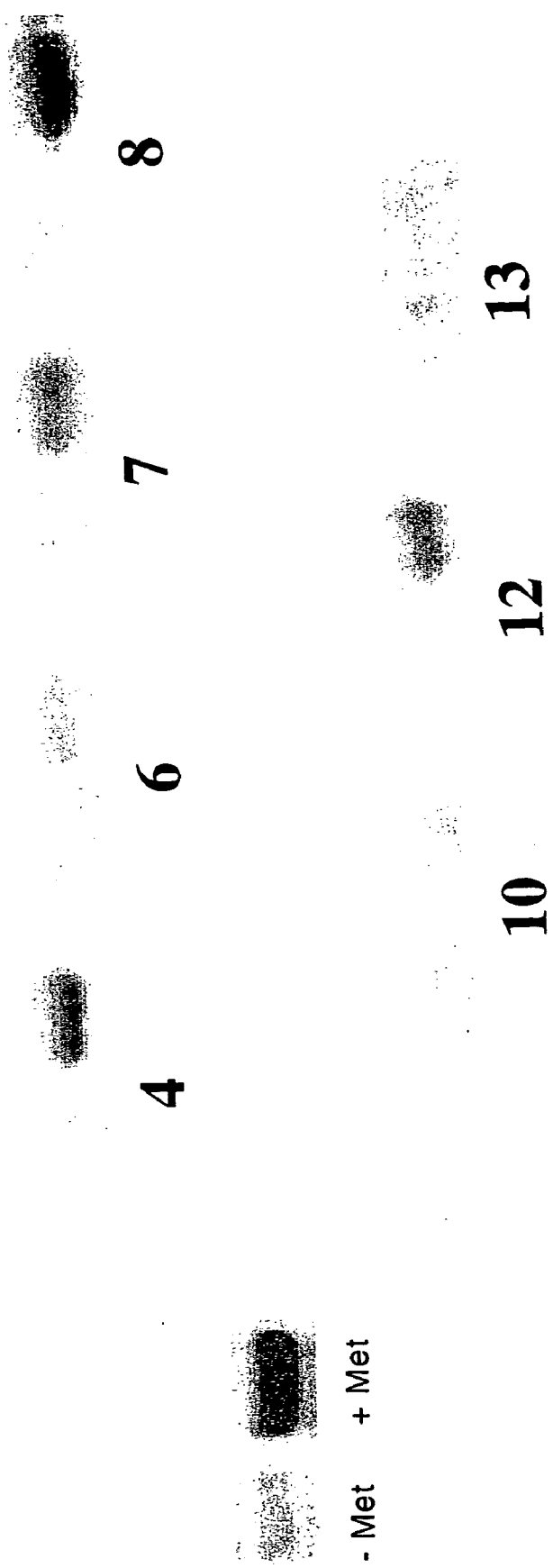
FIG. 9 shows the SDS-PAGE analysis of mDHFR synthesis by *E. coli* strains CAG18491/pQE15/pREP4 (the left panel in each pair, pQE15) and CAG18491/pQE15-MRS/pREP4 (the right panel in each pair, pQE15-MRS), as described in Example II, infra. Cultures (M9+19AA) were supplemented with the analogues 4, 6, 7, 8, 10, 12, and 13 at 500 mg/l, as indicated. Negative (−Met) and positive (+Met) controls of CAG18491/pQE15-MRS/pREP4 cultures are also shown for comparison

For cultures supplemented with amino acids at 500 mg/liter, however, the target protein mDHFR could be observed for certain amino acid analogues only in cultures of cellular hosts containing the MetRS (FIG. 9). FIG. 9 demonstrates that the modified bacterial hosts CAG18491/pQE15-MRS/pREP4 are able to produce the target protein in cultures supplemented with 500 mg/liter of 4, 7, 8, and 12. Quantitative characterization of the kinetic parameters of these analogues demonstrates that although the analogues do not support measurable levels of $PP_i$ exchange after 20 minutes, they are activated by the MetRS in vitro (FIG. 10). Due to the very slow rate of activation supported by these analogues, increasing the concentration of the analogues in the medium must be combined with introduction of pQE15-MRS (SEQ ID NO.: 1) into the bacterial host in order to raise the rate of activation of these analogues sufficiently to permit protein biosynthesis.

Figure 11:
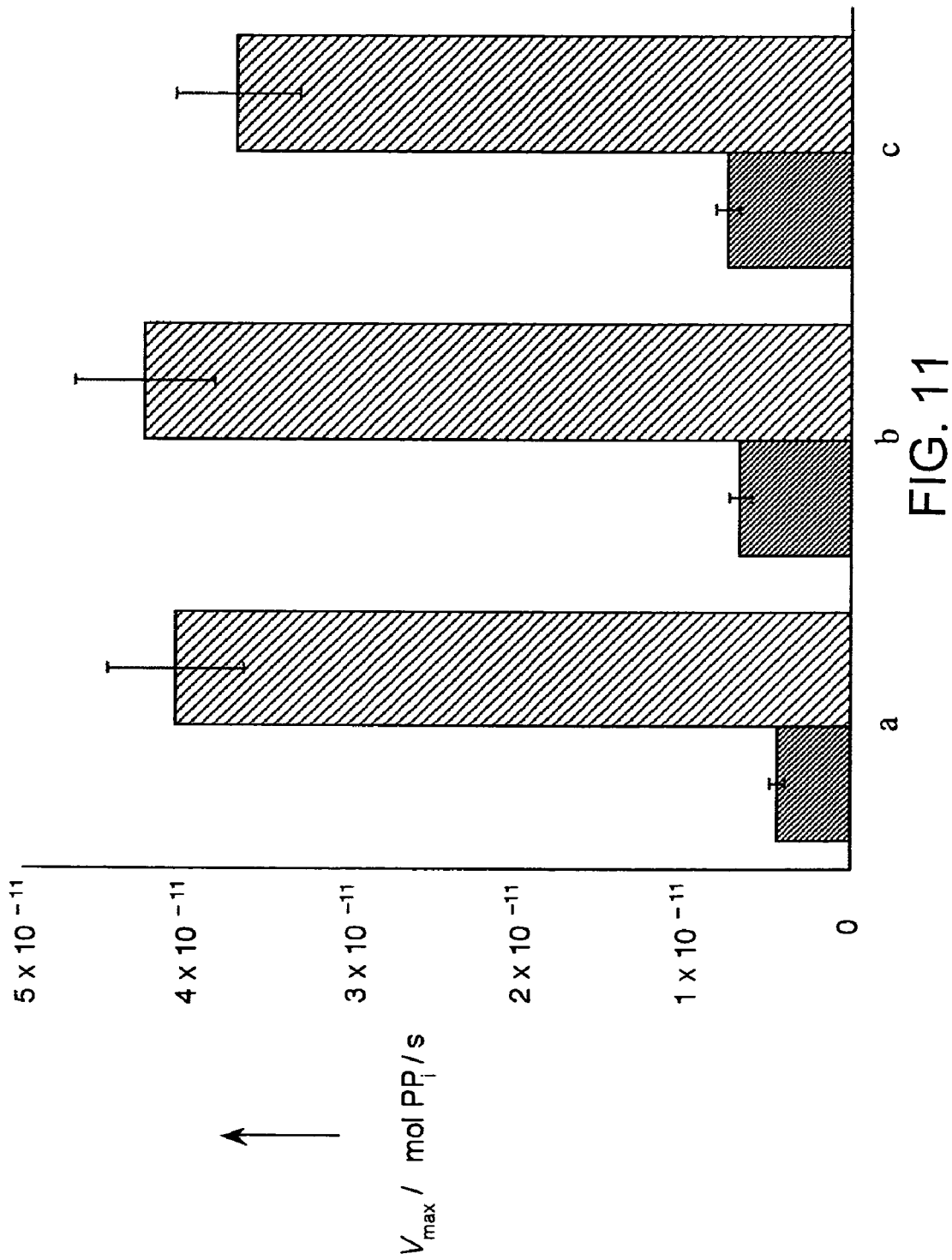
FIG. 11 illustrates the activation rates of methionine by whole cell lysates, as described in Example II, infra. Maximum ATP-$PP_i$ exchange velocities, measured at a saturating concentration of methionine (750 μM), are shown for whole cell lysates of B834(DE3)/pQE15/pREP4 (solid) and of B834(DE3)/pQE15-MRS/pREP4 (striped). Rates were measured for (a) cell lysates obtained from cultures prior to protein expression, (b) cell lysates obtained from cultures supplemented with methionine during protein expression, and (c) cell lysates obtained from cultures supplemented with transcrotylglycine during protein expression.

To confirm the supposition that the MetRS activity of a cellular host is increased by the introduction of pQE15-MRS, direct measurement of the MetRS activities of whole cell lysates was conducted. B834(DE3)/pQE15-MRS/pREP4 exhibits a $V_{max}$ for methionine activation approximately 30-fold higher than that observed for the control host B834(DE3)/pQE15/pREP4 (FIG. 11). Similarly, CAG18491/pQE15-MRS/pREP4 exhibits a $V_{max}$ for methionine activation approximately 50-fold higher than that observed for the control host CAG18491/pQE15/pREP4. ATP-$PP_i$ exchange assays were conducted using the methods as described supra. A 50-µl aliquot of whole cell lysate with a normalized $OD_{600}$ of 20 was prepared by one freeze-thaw cycle and added to the assay mixture to yield a final volume of 150 µl. A saturating concentration of methionine (750 µM) was used to determine the maximum exchange velocity for each cell lysate.

These results show clearly that increasing the MetRS activity of the host is necessary and sufficient to observe translational activity of 4, 5, 7, 8, 11, and 12 under convenient conditions in vivo. Protein yields (mDHFR-Tcg) of approximately 8.5 mg/liter were observed for B834(DE3)/pQE15-MRS/pREP4 cultures supplemented with Tcg, compared with yields of approximately 35 mg/liter for both B834(DE3)/pQE15-MRS/pREP4 and B834(DE3)/pQE15/pREP4 cultures supplemented with methionine. Amino acid analysis of protein containing Tcg shows a decrease in methionine content to 0.3 mol % from the expected value of 3.8 mol %. It was not possible to detect Tcg directly by amino acid analysis, owing to instability of the analogue under the analysis conditions. If depletion of methionine is assumed to result from replacement by Tcg, the observed analysis corresponds to an overall extent of incorporation of the analogue of 91±2%. Amino acid analysis of MDHFR containing the other analogues (4, 7, 8, 11, and 12), showed 92–98% replacement of methionine.

Figure 12:
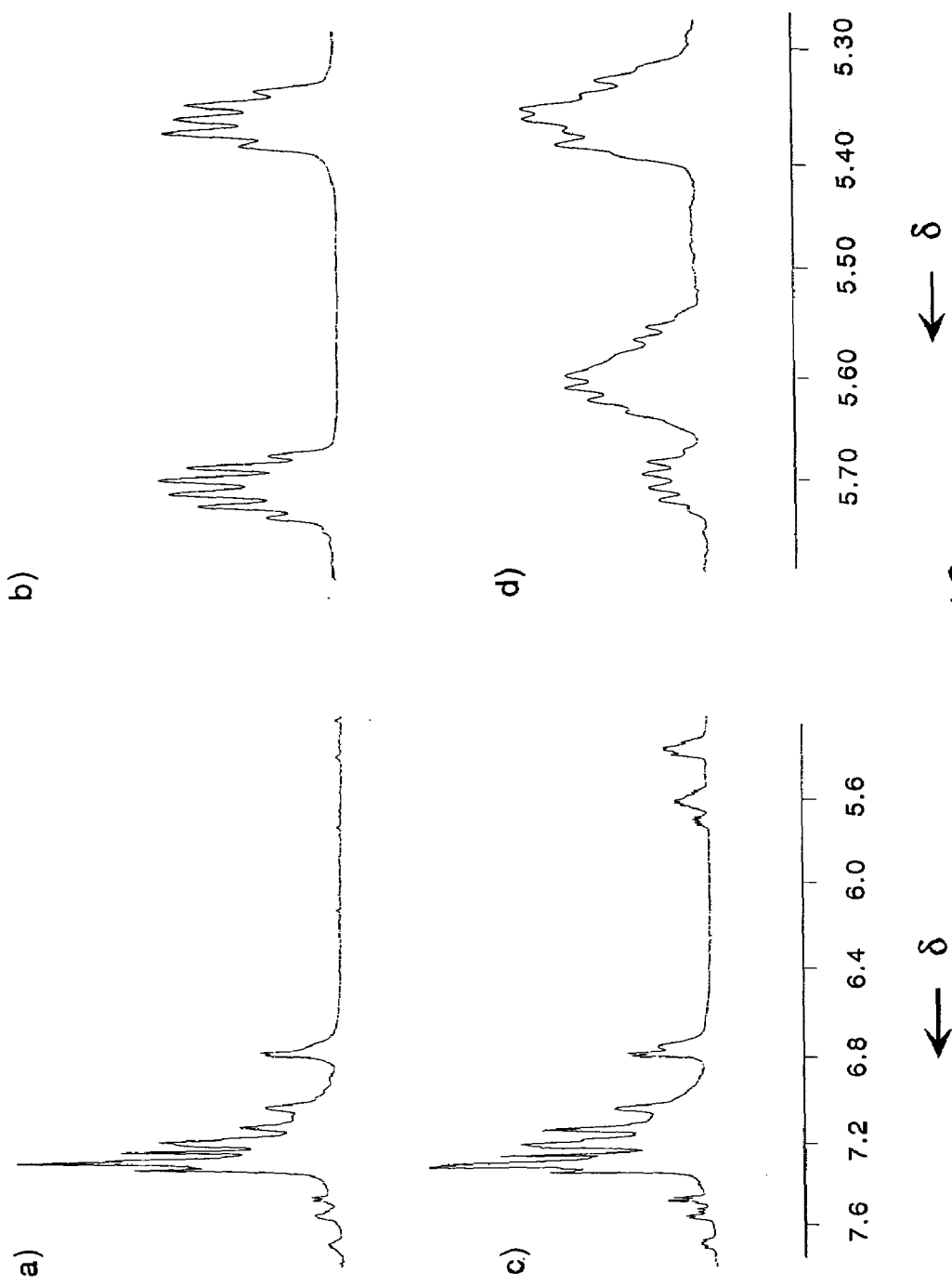
FIG. 12 shows the Proton NMR spectra (599.69 MHz) of (a) MDHFR, (b) Tcg, (c and d) mDHFR-Tcg, as described in Example II, infra. Samples were dissolved at concentrations of approximately 10 mg/ml in $D_2O$ containing 2% d-formic-d-acid and spectra were collected at 25° C. overnight.

A direct assessment of the extent of incorporation of Tcg into mDHFR was provided by NMR spectroscopy. Proton NMR spectra were recorded using a Varian Inova NMR spectrometer with proton acquisition at 599.69 MHz. Spectra were recorded at 25° C. overnight. A simple presaturation pulse was used for water suppression. Comparisons of the 600 MHz proton NMR spectra (FIG. 12) of mDHFR, Tcg, and mDHFR-Tcg indicate the appearance, in the mDHFR-Tcg spectrum (FIG. 12c), of the Tcg vinylene protons at $\delta=5.35$ ($\delta$-CH) and $\delta=5.60-5.70$ ($\gamma$-CH). The resonances at $\delta=5.35$ and $\delta=5.70$ occur at the same chemical shift values as in free Tcg and are clearly due to incorporation of Tcg into mDHFR. That the resonance at $\delta=5.60$ arises from the $\gamma$-CH vinylene proton of Tcg is suggested by the fact that the integrated intensity of the resonance at $\delta=5.35$ equals the sum of the integrations of the resonances at $\delta=5.60$ and $\delta=5.70$. This assignment is confirmed by 1D TOCSY (Total Correlation Spectroscopy) experiments which indicate that the protons at both $\delta=5.60$ and $\delta=5.70$ are members of the same spin system (and therefore the same amino acid) as those at $\delta=5.35$. More importantly, the 1D TOCSY experiments also show that the protons at $\delta=5.35$ (and therefore those at $\delta=5.60$ and $\delta=5.70$) are associated with the spin system of the entire Tcg side chain (1D TOCSY spectra were recorded on a Varian Inova NMR spectrometer with proton acquisition at 599.69 MHz).

A 1D TOCSY pulse sequence (D. Uhrin, P. N. Barlow, *J. Magn. Reson.* 1997, 126, 248–255) with selective irradiation of the resonance at $\delta=5.35$ (E. Kupce, J. Boyd, I. D. Campbell, *J. Magn. Reson. Ser. B.* 1995, 106, 300–303) was used to identify which protons belonged to the spin system of the $\delta=5.35$ resonance. The selectivity of the pulse is demonstrated in a separate, simple 1D experiment in which the selective pulse was applied alone; no other resonances were observed in the spectrum under these conditions. Observation after a mixing time of 60 ms, however, showed the protons at $\delta=5.60$ and $\delta=5.70$, indicating that those protons are members of the same spin system (and therefore the same amino acid residue) as those corresponding to the resonance at $\delta=5.35$. The $\alpha$-carbon and side chain $\beta$- and $\epsilon$-carbon protons were also observed at chemical shift values characteristic of the free amino acid ($\delta=4.3$ ($\alpha$-CH), 2.5 ($\beta$-CH2), and 1.6 ($\delta$-CH3)). Integration of the spectrum suggests that 5 of the 8 methionine positions (occupied by Tcg) are represented by the resonance at $\delta=5.60$; these protons must reside in a magnetically-distinct environment from the protons at $\delta=5.70$. These results unequivocally demonstrate the translational activity of Tcg in the host strain outfitted with elevated MetRS activity. Integration of the NMR spectrum indicates 90±6% replacement of methionine.

Figure 13:
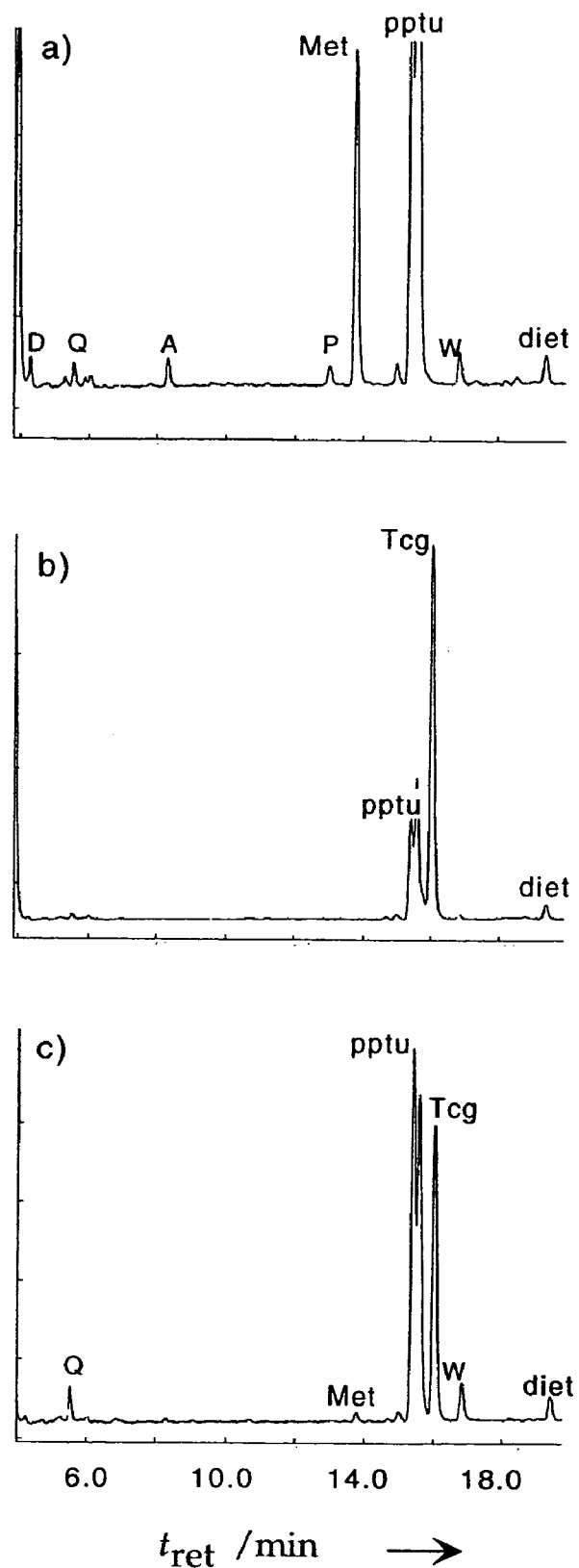
FIG. 13 depicts the N-terminal sequencing results indicating occupancy of the initiator site in mDHFR-Tcg, as described in Example II, infra. Chromatograms are shown for (a) the N-terminal residue of mDHFR, (b) Tcg control, and (c) the N-terminal residue of mDHFR-Tcg, as determined via Edman degradation.
Figure 14:
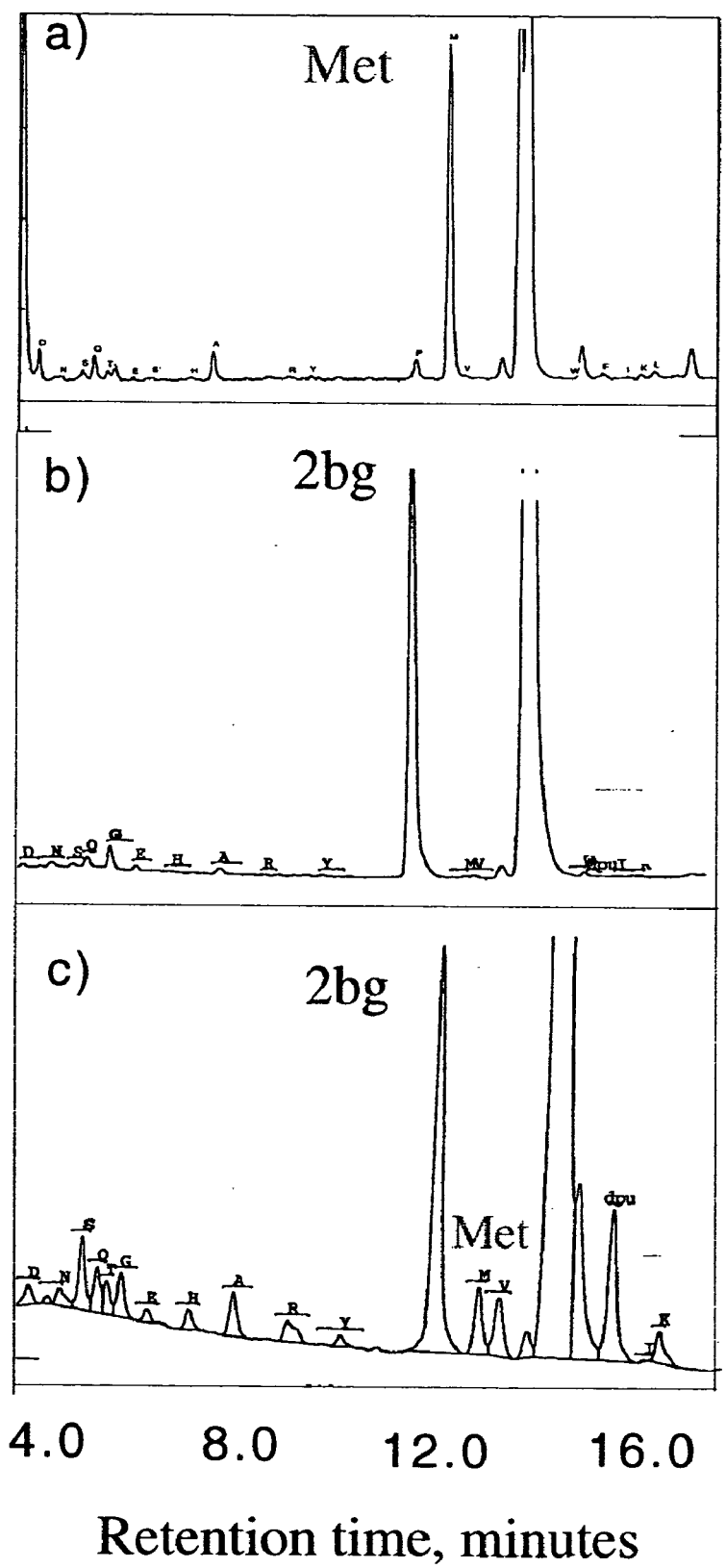
FIG. 14 depicts the N-terminal sequencing results indicating occupancy of the initiator site in mDHFR-bg, as described in Example II, infra. Chromatograms are shown for (a) the N-terminal residue of mDHFR, (b) 2bg control, and (c) the N-terminal residue of mDHFR-2bg, as determined via Edman degradation.

Retention of the N-terminal (initiator) methionine in mDHFR was expected on the basis of the identity of the penultimate amino acid (P. H. Hirel, J. M. Schmitter, P. Dessen, G. Fayat, S. Blanquet, *Proc. Natl. Acad. Sci. USA* 1989, 86, 8247–8251), so N-terminal sequencing provided a third means of assessing the extent of replacement of methionine by analogues 4, 5, 7, 8, 11, and 12. Because the analogues were not degraded under the analysis conditions, they could be detected directly. Comparison of chromatograms of the N-terminal residues of mDHFR and mDHFR-Tcg (FIG. 13) demonstrate that the methionine that normally occupies the initiator position of mDHFR (FIG. 13a) was nearly completely replaced with Tcg (FIG. 13b) in mDHFR-Tcg (FIG. 13c). The signal corresponding to methionine eluted at 13.8 min while that corresponding to Tcg eluted at 16.0 min. The large peaks (pptu) which elute at approximately 15.4 min correspond to piperidylphenylthiourea, a product of the analysis resulting from the buffer, and the small peak (diet) at 19.4 min corresponds to diethylphthalate, an internal standard. These results clearly indicate the incorporation of Tcg at the initiator site of mDHFR-Tcg and corroborate the NMR results. Integration of the peak areas corresponding to Tcg and to methionine indicates 96±2% incorporation of the analogue at the initiator position. Similar analysis of mDHFR-2bg (2-butynylglycine) by N-terminal sequencing indicates 98±2% replacement of methionine (FIG. 14). Analysis of mDHFR containining analogues 8 and 12 shows replacement of methionine by these analogues at levels of 85–90%.

The incorporation of 4, 5, 7, 8, 11, and 12 into proteins in vivo constitutes the first example of broadening the amino acid substrate range of the *E. coli* translational apparatus via overproduction of MetRS in a bacterial host. The utilization of 4, 5, 7, 8, 11, and 12 in all stages of protein synthesis (including initiation) indicates the appropriateness of targeting the aminoacyl-tRNA synthetase in studies aimed at in vivo incorporation of amino acid analogues into proteins. Transport into the cell, recognition by methionyl-tRNA formylase, and recognition by the elongation factors and the ribosome are less likely to be limiting factors.

These results indicate that this simple strategy of overexpression of aminoacyl-tRNA synthetase may be used to modify proteins by incorporation of amino acid analogues that are poor substrates for aminoacyl-tRNA synthetase and that would be essentially inactive in conventional expression hosts.

Overexpression of mutant forms of the aminoacyl-tRNA synthetase prepared via site-directed mutagenesis or directed evolution (F. H. Arnold, J. C. Moore, *Adv. Biochem. Eng. Biotech.* 1997, 58, 1–14; F. H. Arnold, *Chem. Eng. Sci.* 1996, 51, 5091–5102) should provide additional strategies for incorporating amino acid analogues into proteins in vivo.

The results reported here also suggest new opportunities for macromolecular synthesis via protein engineering. The versatile chemistry of unsaturated functional groups (B. M. Trost, I. Fleming, *Comprehensive Organic Synthesis*, Pergamom Press, Oxford, 1991) can be used to control protein structure and function through chemical derivatization, an especially intriguing possibility in this case given the important role of methionine in protein-protein recognition processes. For example, ruthenium-catalyzed olefin metathesis (D. M. Lynn, B. Mohr, R. H. Grubbs, *J. Am. Chem. Soc.* 1998, 120, 1027–1028; E. L. Dias, T. N. SonBinh, R. H. Grubbs, *J. Am. Chem. Soc.* 1997, 119, 3887–3897) of homoallylglycine (T. D. Clark, M. R. Ghadiri, *J. Am. Chem. Soc.* 1995, 117, 12364–12365) and o-allylserine (H. E. Blackwell, R. H. Grubbs, *Angew. Chem.* 1998, 110, 3469–3472; *Angew. Chem. Int. Ed,* 1998, 37, 3281–3284) side chains has been used to produce covalently-modified peptide structures of various kinds. The incorporation of Tcg may be singularly useful in this regard as the internal olefin is active in aqueous-phase ring closing metathesis reactions, whereas terminally-unsaturated groups (such as those previously used to replace methionine in vivo) are not (T. A. Kirkland, D. M. Lynn, R. H. Grubbs, *J. Org. Chem.* 1998, 63, 9904–9909).

EXAMPLE III

This example demonstrates that activation of methionine analogues in vitro correlates well with the ability of these analogues to support protein synthesis in vivo, substantiating the critical role of aminoacyl-tRNA synthetase in controlling the incorporation of amino acid analogues into proteins.

Reagents

Each of the analogues 2–7 and 11 (FIG. 2) was prepared by alkylation of diethyl acetamidomalonate with the appropriate tosylate followed by decarboxylation and deprotection of the amine function (as described in Example I). Methionine and analogues 8, 9, 12 and 13 were obtained from Sigma (St. Louis, Mo). Radiolabeled sodium pyrophosphate was purchased from NEN Life Science Products, Inc., and isopropyl-β-D-thiogalactopyranoside was obtained from Calbiochem. The RGS-His antibody and anti-mouse IgG horseradish peroxidase conjugate used for Western blotting procedures were obtained from Qiagen and Amersham Life Sciences, respectively. All other reagents used during protein biosynthesis and purification and for activation assays were commercially available from Sigma, Aldrich, and Qiagen, and were used as received.

In Vitro Activation Assays

The fully active, truncated form of MetRS was purified from overnight cultures of E. coli JM101 cells carrying the plasmid pGG3 (Kim, H. Y.; Ghosh, G.; Schulman, L. H.; Brunie, S.; Jakubowski, H. Proc. Natl. Acad. Sci. USA 1993, 90, 11553–11557), by using size exclusion methods previously reported (Mellot, P.; Mechulam, Y.; LeCorre, D.; Blanquet, S.; Fayat, G. J. Mol. Biol. 1989, 208, 429–443). Purified enzyme solutions (in 10 mM phosphate, pH 6.7, 10 mM β-mercaptoethanol) were concentrated to at least 3 μM prior to their storage in 40% glycerol at −20° C. Concentrations of enzyme stocks were determined by the Bradford method, using samples of MetRS quantified by amino acid analysis as standards.

Activation of methionine analogues by MetRS was assayed via the amino acid-dependent ATP-PP$_i$ exchange reaction at room temperature, also as previously described (Mellot, P.; Mechulam, Y.; LeCorre, D.; Blanquet, S.; Fayat, G. J. Mol. Biol. 1989, 208, 429–443; Ghosh, G.; Pelka, H.; Schulman, L. D. Biochemistry 1990, 29, 2220–2225). The assay, which measures the $^{32}$P-radiolabeled ATP formed by the enzyme-catalyzed exchange of $^{32}$P-pyrophosphate (PP$_i$) into ATP, was conducted in 150 μl of reaction buffer (pH 7.6, 20 mM imidazole, 0.1 mM EDTA, 10 mM β-mercaptoethanol, 7 mM MgCl$_2$, 2 mM ATP, 0.1 mg/ml BSA, and 2 mM PP$_i$ (in the form of sodium pyrophosphate with a specific activity of approximately 0.5 TBq/mole)).

Kinetic parameters for methionine analogues 2, 3, 5, 9 and 11 were obtained with an enzyme concentration of 75 nM and analogue concentrations of 100 μM to 20 mM. Parameters for methionine were obtained by using methionine concentrations ranging from 10 μM to 1 mM. Aliquots (20 μl) were removed from the reaction mixture at various time points and quenched in 0.5 ml of a solution comprising 200 mM PP$_i$, 7% w/v HClO$_4$, and 3% w/v activated charcoal. The charcoal was rinsed twice. with 0.5 mL of a 10 mM PP$_i$, 0.5% HClO$_4$ solution and then resuspended in 0.5 mL of this solution and counted via liquid scintillation methods. Kinetic constants were calculated by a nonlinear regression fit of the data to the Michaelis-Menten model.

In Vivo Incorporation of Amino Acid Analogues

Buffers and media were prepared according to standard protocols (Ausubel, F. M.; Brent, R.; Kingston, R. E.; Moore, D. D.; Seidman, J. G.; Smith, J. A.; Struhl, K., Eds. Current Protocols in Molecular Biology; John Wiley and Sons: New York, 1998). The E. coli methionine auxotroph CAG18491 (λ$^-$; rph-1, metE3079.:Tn10) was transformed with plasmids pQE15 and pREP4 (Qiagen), to obtain the expression host CAG18491/pQE15/pREP4. The auxotroph was transformed with the plasmids pQE15-MRS (SEQ ID NO.: 1) and pREP4 to obtain the modified bacterial expression host CAG18491/pQE15-MRS/pREP4. Both bacterial expression hosts produce the target protein mDHFR under control of a bacteriophage T5 promoter; the modified host also expresses extra copies of the MetRS gene under control of the constitutive metG pl promoter (Dardel, F.; Panvert, M.; Fayat, G. Mol. Gen. Genet. 1990, 223, 121–133).

Protein Expression (1 Liter Scale).

Similar procedures were used for preparation and isolation of mDHFR from media supplemented with the L-isomers of 1, 2, 3, or 9. M9AA medium (100 mL) supplemented with 1 mM MgSO$_4$ 0.2w% glucose, 1 mg/L thiamine chloride and the antibiotics ampicillin (200 mg/L) and kanamycin (35 mg/L) was inoculated with the appropriate E. coli strain (CAG18491/pQE15/pREP4 or CAG18491/pQE15-MRS/pREP4) and grown overnight at 37° C. This culture was used to inoculate 900 mL M9AA medium supplemented as described. The cells were grown to an optical density at 600 nm (OD$_{600}$) of approximately 0.9 and a medium shift was performed. The cells were sedimented for 10 min at 3030 g at 4° C., the supernatant was removed, and the cell pellet was washed twice with 600 mL of M9 medium. Cells were resuspended in 1000 mL of the M9AA medium described above, without methionine, and supplemented with 20 mg/L of the L-isomer of either 1, 2, 3, or 9. Protein synthesis was induced by addition of isopropyl-β-D-thiogalactopyranoside (IPTG) to a final concentration of 0.4 mM. Samples (1 mL) were collected after 4.5 hours, the OD$_{600}$ measured, and cells resuspended with distilled water to yield a normalized OD$_{600}$ of 20. Protein expression was monitored by SDS polyacrylamide gel electrophoresis (12% acrylamide running gel); accumulation of MDHFR could be observed at an apparent molar mass of approximately 28 kDa after Coomassie staining.

Protein Purification.

Approximately 4.5 h after induction, cells were sedimented (9,800 g, 10 min, 4° C.) and the supernatant was removed. The pellet was placed in the freezer overnight. The cells were thawed for 30 min at 37° C., 30 mL of buffer (6 M guanidine-HCl, 0.1 M NaH$_2$PO$_4$, 0.01 M Tris, pH 8) was added and the mixture was shaken at room temperature for 1 h. The cell debris was sedimented (15,300 g, 20 min, 4° C.) and the supernatant was subjected to immobilized metal affinity chromatography (Ni-NTA resin) according to the procedure described by Qiagen (The Qiagen Expressionist; Qiagen; Valencia, Calif., 2000). The supernatant was loaded on 10 mL of resin which was then washed with 50 mL of guanidine buffer followed by 25 mL of urea buffer (8 M urea, 0.1 M NaH$_2$PO$_4$ and 0.01 M Tris, pH 8). Similar urea buffers were used for three successive 25 mL washes at pH values of 6.3, 5.9 and 4.5, respectively. Target protein was obtained in washes at pH 5.9 and 4.5. These washes were combined and dialyzed (Spectra/Por membrane 1, MWCO=6–8 kDa) by batchwise dialysis against doubly distilled water for 4 days with at least 12 total changes of water. The dialysate was lyophilized to a purified powder of mDHFR. Experiments in M9AA medium afford approximately 30 mg of mDHFR for each of the bacterial expression hosts, while a control experiment in 2xYT medium afforded approximately 60 mg of mDHFR. Protein yields are reported as mg protein obtained per liter of bacterial culture;

approximately 5–6 g of wet cells are obtained per liter of culture regardless of the identity of the analogue used to supplement the medium.

Protein Expression (5 mL Scale).

M9AA medium (50 mL) supplemented with 1 mM $MgSO_4$, 0.2 wt % glucose, 1 mg/L thiamine chloride and the antibiotics ampicillin (200 mg/L) and kanamycin (35 mg/L) was inoculated with 5 mL of an overnight culture of the appropriate bacterial expression host. When the turbidity of the culture reached an $OD_{600}$ of 0.8, a medium shift was performed. The cells were sedimented for 10 min at 3030 g at 4° C., the supernatant was removed, and the cell pellet was washed twice with 25 mL of M9 medium. Cells were resuspended in 50 mL of the M9AA medium described above, without methionine. Test tubes containing 5 mL aliquots of the resulting culture were prepared, and were supplemented with 10 μL of 10 mg/mL L-methionine (1) (positive control), L-homoallylglycine (2), L-homopropargylglycine (3), or L-norleucine (9), respectively. A culture lacking methionine (or any analogue) served as the negative control. Protein expression was induced by addition of IPTG to a final concentration of 0.4 mM. After 4 h, the $OD_{600}$ was measured, and the samples were sedimented. After the supernatant was decanted, the cell pellets were resuspended in distilled water to yield a normalized OD of 20.

Protein expression was monitored by SDS polyacrylamide gel electrophoresis (12% acrylamide running gel), followed by Western blotting. After transfer to a nitrocellulose membrane, Western blots were developed by treatment with a primary RGS-His antibody, followed by treatment with a secondary anti-mouse IgG conjugated to horseradish peroxidase to provide detection by chemiluminescence. Films were checked to ensure that band intensity was not saturated. Levels of protein synthesis were estimated by the intensity of the band on the gel, as determined using a Pharmacia Ultrascan XL laser densitometer and analysis by Pharmacia GelScan XL software. The accumulation of target protein is taken as evidence for incorporation of the amino acid analogue, as 2, 3, 5, 9 and 11 have been shown to replace methionine, even in modified bacterial hosts, at levels of 92–98% (van Hest, J. C. M.; Tirrell, D. A. *FEBS Lett.* 1998, 428, 68–70; as described in Example I, infra; Budisa, N.; Steipe, B.; Demange, P.; Eckerskorn, C.; Kellermann, J.; Huber, R. *Eur. J. Biochem.* 1995, 230, 788–796).

Results and Discussion

Studies with methionine analogues 2–13 (as described in Example I, infra), demonstrated that 2 and 3 can be incorporated into proteins with extents of substitution up to 98%. The incorporation of 9 had been previously reported (Budisa, N.; Steipe, B.; Demange, P.; Eckerskom, C.; Kellermann, J.; Huber, R. *Eur. J. Biochem.* 1995, 230, 788–796). In contrast, 4–8 and 10–13 do not support protein synthesis in the absence of methionine in a conventional bacterial expression host; investigation of the activation of the analogues by methionyl-tRNA synthetase (MetRS) indicated that 4–8 and 10–13 are not efficiently activated by the enzyme.

Overproduction of MetRS in the bacterial host, however, permits incorporation of 4, 5, 7, 8, 11 and 12, which show very slow exchange of $PP_i$ in in vitro activation assays (Example II, infra). These results indicate that the aminoacyl-tRNA synthetase are appropriate targets for studies aimed at the incorporation of amino acid analogues into proteins in vivo. The results also suggest that neither transport into the cell nor recognition by the elongation factors or the ribosome limits the incorporation of these amino acid analogues into proteins in vivo.

In this example, the in vitro activation of 2–13 by MetRS was characterized in order to determine the roles of the synthetase in controlling analogue incorporation and protein yield in media supplemented with amino acid analogues. Furthermore, the analogues 2 and 3, which replace methionine in vivo, may be useful for chemical modification of proteins by olefin metathesis (Clark, T. D.; Kobayashi, K.; Ghadiri, M. R. *Chem. Eur. J.* 1999, 5, 782–792; Blackwell, H. E.; Grubbs, R. H. *Angew. Chem. Int. Ed. Engl.* 1998, 37, 3281–3284), palladium-catalyzed coupling (Amatore, C.; Jutand, A. *J. Organomet. Chem.* 1999, 576, 255–277; Tsuji, J. *Palladium Reagents and Catalysts: Innovations in Organic Synthesis*; John Wiley and Sons: New York, 1995; Schoenberg, A.; Heck, R. F. *J. Org. Chem.* 1974, 39, 3327–3331), and other chemistries (Trost, B. M.; Fleming, I., Eds. *Comprehensive Organic Synthesis*; Pergamon Press: Oxford, 1991).

Figure 18:
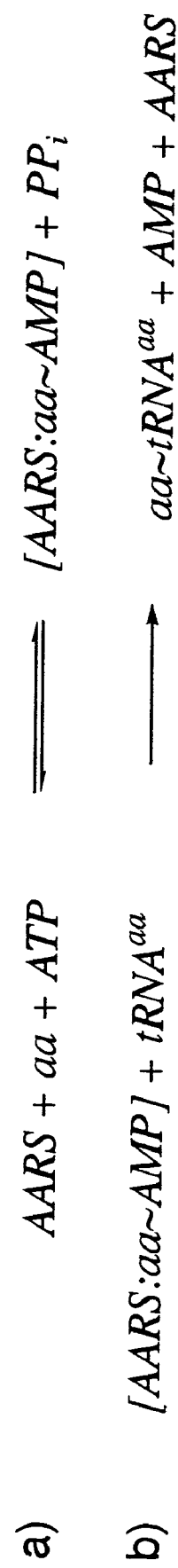
FIG. 18 illustrates the activation (a) and aminoacylation (b) steps of amino acid attachment to tRNA, as described in Example III, infra.

The attachment of an amino acid to its cognate tRNA proceeds in two steps (FIG. 18). Activation, the first step, involves the enzyme-catalyzed formation of an aminoacyl adenylate (designated αα~AMP in FIG. 18) and can be examined by monitoring the rate of exchange of radiolabeled pyrophosphate ($^{32}P-PP_i$) into ATP (Fersht, A. *Structure and Mechanism in Protein Science*; W. H. Freeman and Company: New York, 1999). Aminoacylation, the second step, can be evaluated by monitoring the amount of radiolabeled amino acid attached to tRNA in the presence of the enzyme. Because initial recognition of an amino acid by its aminoacyl-tRNA synthetase is perhaps the most critical step in the incorporation of amino acid analogues into proteins in vivo. Thus, the focus has been on the in vitro activation of methionine analogues by MetRS was evaluated and the results compared to those obtained in studies of in vivo incorporation.

The rates of activation of 2–13 by MetRS were determined by the $ATP-PP_i$ exchange assay, and were found to correlate well with the results of the in vivo studies; analogues 2–5, 7–9, 11 and 12 (those which had been shown to support protein synthesis) exhibited measurable exchange of $PP_i$ (Example I and II, infra). The kinetic parameters $k_{cat}$ and $K_m$ were determined for each of these analogues; the results for analogues 2, 3, 5, 9 and 11 are summarized in FIG. 15. The measured $K_m$ for methionine matched previously reported values (Kim, H. Y.; Ghosh, G.; Schulman, L. H.; Brunie, S.; Jakubowski, H. *Proc. Natl. Acad. Sci. USA* 1993, 90, 11553–11557). The value determined for $k_{cat}$ was slightly lower than the literature value. Comparison of the $k_{cat}/K_m$ values for each of the analogues with that for methionine showed that these analogues were 500-fold to 13825-fold poorer substrates for MetRS than methionine.

FIG. 15 also demonstrates that methionine analogues that are activated up to 2000-fold more slowly by MetRS than methionine can support protein synthesis in a conventional bacterial host in the absence of methionine. (Poorer substrates, such as 5, require modification of the MetRS activity of the bacterial host in order to support protein synthesis (Example II, infra). These results are comparable to those reported previously for the activation and in vivo incorporation of phenylalanine analogues (Gabius, H. J.; von der Haar, F.; Cramer, F. *Biochemistry* 1983, 22, 2331–2339; Kothakota, S.; Mason, T. L.; Tirrell, D. A.; Fournier, M. J. *J. Am. Chem. Soc.* 1995, 117, 536–537; Ibba, M.; Kast, P.; Hennecke, H. *Biochemistry* 1994, 33, 7107–7112). Comparisons for other amino acids have been limited by a lack of in vitro activation data. The data suggested that amino acid analogues can support protein synthesis in vivo even with surprisingly inefficient activation of the amino acid by its aminoacyl-tRNA synthetase. Activation of methionine analogues by MetRS governs their ability to support protein synthesis in vivo.

Based on these results, it seemed likely that the kinetics of analogue activation would limit the rate and yield of protein synthesis in bacterial cultures supplemented with methionine analogues that are poor substrates for MetRS. This correlation was investigated by comparing the kinetic constants for analogue activation by MetRS with the yield of the target protein murine dihydrofolate reductase (mDHFR) obtained from 1-liter cultures of the bacterial host CAG18491/pQE15/pREP4.

The CAG18491/pQE15/pREP4 bacterial host was produced by transforming the *E. coli* methionine auxotroph CAG18491 with the expression plasmid pQE15 and the repressor plasmid pREP4. The expression plasmid pQE15 encodes mDHFR under control of a bacteriophage T5 promoter and an N-terminal hexahistidine sequence that permits purification of the target protein by immobilized metal chelate affinity chromatography (*The Qiagen Expressionist*; Qiagen; Valencia, Calif., 2000).

Figure 16:
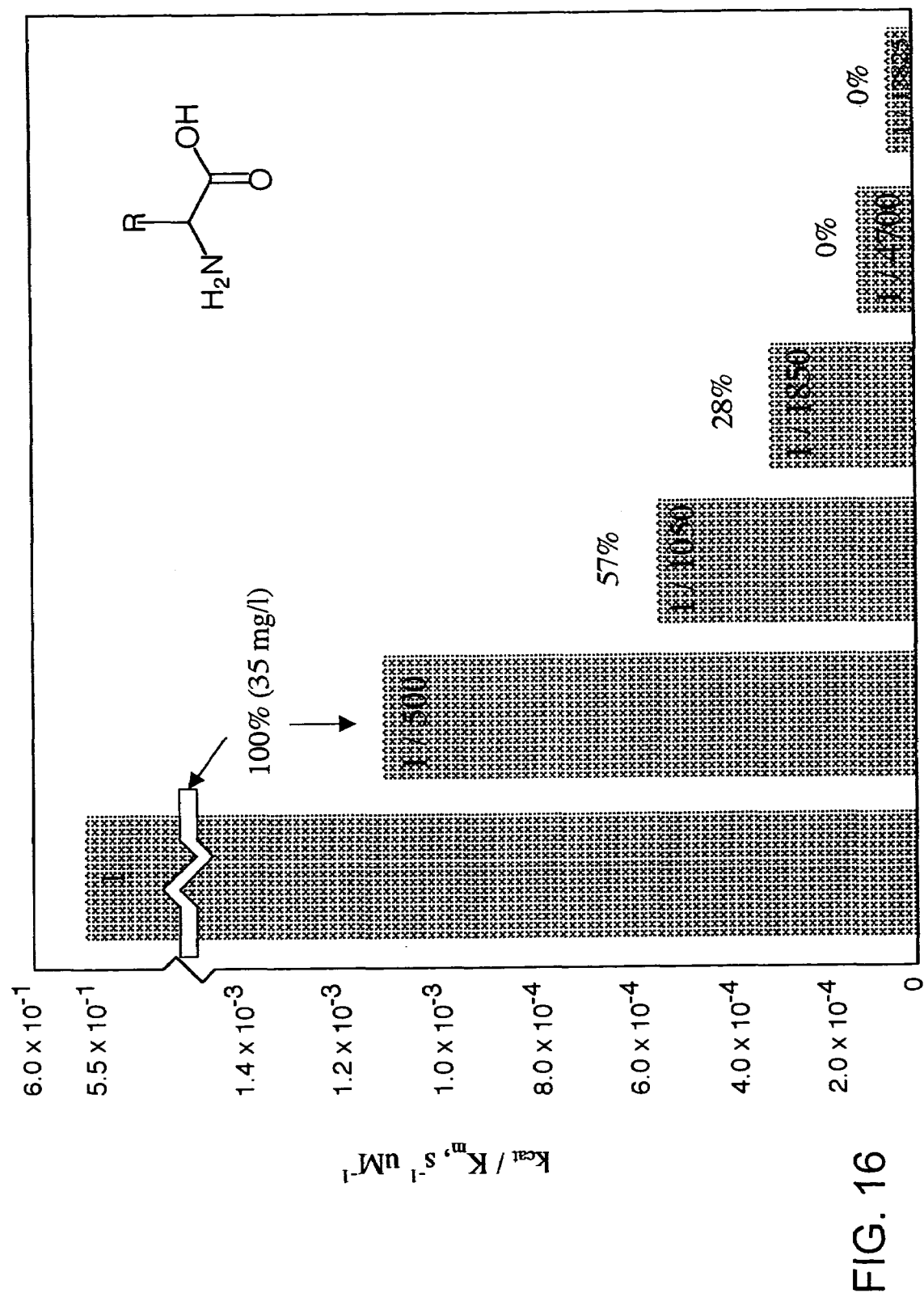
FIG. 16 shows the comparison of the kinetic parameters for methionine analogues in the ATP-$PP_i$ exchange reaction and relative protein yields from conventional bacterial host cultures supplemented with the analogues, as described in Example III, infra.

The kinetic constants for analogue activation and the corresponding protein yields are listed in FIG. 15 and shown in FIG. 16. Analogues with the highest $k_{cat}/K_m$ values also support the highest levels of protein synthesis; the protein yields scale remarkably well with $k_{cat}/K_m$, at least for the poorer substrates. Analogue 3 supported protein synthesis with yields equivalent to those obtained with methionine, despite the fact that 3 is a 500-fold poorer substrate for MetRS than methionine.

Bacterial cultures supplemented with 9 (1050-fold lower $k_{cat}/K_m$) produce 57% as much mDHFR as cultures supplemented with methionine, and cultures supplemented with 2 (1850-fold lower $k_{cat}/K_m$) produce 28% of the control yield of protein. Bacterial cultures supplemented with 5 (4700-fold lower $k_{cat}/K_m$) and 11 (13825-fold lower $k_{cat}/K_m$) did not support measurable levels of protein synthesis in this expression host; however, bacterial hosts exhibiting approximately 30-fold higher MetRS activity produce 23% as much mDHFR in cultures supplemented with 5 as cultures supplemented with methionine (Example II, infra).

These results demonstrate that the rate of methionine analogue activation in vitro does indeed correlate with protein yield in vivo. The results suggest that the kinetics of activation can play a critical role in controlling the rate of protein synthesis in methionine-depleted cultures supplemented with analogues that are poor substrates for MetRS.

Protein yields obtained from bacterial cultures supplemented with methionine analogues might be improved by increasing the MetRS activity of the bacterial host. To test this, the yields of protein prepared were compared in the conventional bacterial expression host, CAG18491/pQE15/pREP4, to those obtained from a modified host, CAG18491/pQE15-MRS/pREP4.

The modified CAG18491/pQE15-MRS/pREP4 host was prepared by transforming *E. coli* strain CAG18491 with the expression plasmid pQE15-MRS (SEQ ID NO.: 1) (Example II, infra) and the repressor plasmid pREP4. The expression plasmid pQE15-MRS (SEQ ID NO.: 1) encodes MetRS under control of the *E. coli* promoter metG p1 (Genbank accession number X55791) (Dardel, F.; Panvert, M.; Fayat, G. *Mol. Gen. Genet.* 1990, 223, 121–133) as well as the target protein mDHFR. The MetRS activity of the bacterial hosts was determined as previously described (Example II, infra), with the modified host exhibiting 50-fold higher MetRS activity than the conventional strain.

Figure 17:
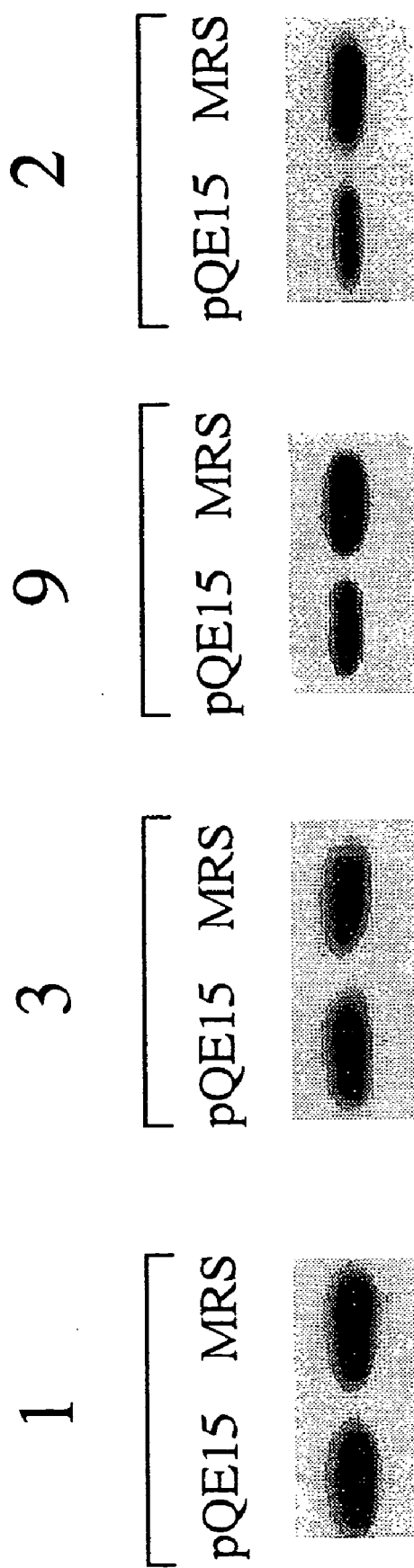
FIG. 17 depicts the Western blot analysis of protein synthesis by bacterial expression hosts CAG18491/pQE15/pREP4 (pQE15) and CAG18491/pQE15-MRS/pREP4 (MRS). Bacterial cultures were supplemented with methionine, 2, 3 or 9, as described in Example III, infra.

Protein synthesis was monitored for 5-ml cultures of these hosts supplemented with methionine or analogues 2, 3, or 9. Western blot analyses of protein synthesis are shown in FIG. 17. Although very low levels of protein synthesis were observed for negative control cultures of CAG18491/pQE15-MRS/pREP4, amino acid analyses, N-terminal sequencing, and NMR analyses of proteins produced in cultures of the modified host supplemented with 5 and 11 (the poorest of the substrates) still showed 90–96% replacement of methionine by 5 and 11 (Example II, infra). Thus, the level of protein synthesis shown in FIG. 17 resulted from the incorporation of the analogue and was not due to incorporation of residual methionine.

For cultures supplemented with methionine or 3, the modified host, CAG18491/pQE15-MRS/pREP4, does not exhibit higher levels of protein synthesis than the conventional host CAG18491/pQE15/pREP4. Analysis by laser densitometry confirmed these results, and revealed approximately equal accumulation of target protein for both strains; identical results have been obtained for large-scale expressions and purification of mDHFR. Activation of the analogue by MetRS does not appear to limit protein synthesis in cultures supplemented with 3. For cultures supplemented with 2 or 9, however, the modified bacterial host exhibits significantly increased levels of protein synthesis in comparison with the conventional host. Laser densitometry analysis indicates that the level of protein synthesis in the modified host is increased approximately 1.5-fold over that in the conventional host for cultures supplemented with 2, and approximately 1.4-fold for cultures supplemented with 9. Activation of these analogues by MetRS appears to limit protein synthesis in the conventional host, such that increasing the MetRS activity of the host is sufficient to restore high levels of protein synthesis. Preliminary results indicated that the yield of mDHFR obtained from large-scale cultures of CAG18491/pQE15-MRS/pREP4 supplemented with 2 or 9 are increased to approximately 35 mg/L (from 10 mg/L obtained from cultures of CAG 18491/pQE15/pREP4 (FIG. 15)).

The results indicate that overexpression of MetRS can improve protein yields for cultures supplemented with methionine analogues that are poor substrates for MetRS, and provide an attractive general method for efficient production of chemically novel protein materials in vivo.

Quantitative assessment of the kinetics of activation by MetRS have indicated that even very poor substrates for the synthetase can be utilized by the protein synthesis machinery of a bacterial expression host. The correlation, shown herein, between the in vitro and in vivo results indicates the important role of the aminoacyl-tRNA synthetase and suggests that site-directed mutatgenesis and/or directed evolution of this class of enzymes may be used to increase further the number of amino acid analogues that can be incorporated into proteins in vivo.

These results also indicate that the kinetics of activation of methionine analogues by MetRS in vitro correlate with the level of protein synthesis supported by the analogues in vivo. The activity of the MetRS in the bacterial host can be manipulated, by overexpression of the MetRS, to improve the yields of proteins containing methionine analogues that are poor substrates for the MetRS. Overexpression of aminoacyl-tRNA synthetase used to improve yields of proteins containing other amino acid analogues, as well as proteins rich in particular natural amino acids. Manipulation of the aminoacyl-tRNA synthetase activities of a bacterial host broadens the scope of protein engineering, by permitting production of natural and artificial proteins, with novel chemical and physical properties.

What is claimed:

1. A method for producing a modified polypeptide, the polypeptide being modified by replacing a selected amino acid with a desired amino acid analogue, which method comprises:
   a. transforming a host cell with:
      i. a vector having a polynucleotide sequence encoding an aminoacyl-tRNA synthetase for the amino acid analogue; and
      ii. a vector having a polynucleotide sequence encoding a polypeptide molecule of interest so as to produce a host vector system; wherein the vectors of (i) and (ii) may be the same or different
   b. growing the host-vector system in a medium which comprises the selected amino acid so that the host vector system overexpresses the aminoacyl-tRNA synthetase c. replacing the medium with a medium which lacks the selected amino acid and has the desired amino acid analogue or adding the desired amino acid analogue to the medium d. growing the host vector system in the medium which has the desired amino acid analogue under conditions so that the host vector system overexpresses the polypeptide molecule of interest and the selected amino acid is replaced with the desired amino acid analogue thereby producing the modified polypeptide.

2. The method of claim 1 wherein the overexpression of an aminoacyl-tRNA synthetase results in an increase in the activity of the aminoacyl-tRNA synthetase.

3. The method of claim 1 wherein said host cell is from an organism which is selected from the group consisting of bacterial, yeast, mammalian, insect, and plant.

4. The method of claim 1 wherein said host cell is an auxotroph.

5. The method of claim 1, wherein said aminoacyl-tRNA synthetase is naturally occurring or genetically engineered.

6. The method of claim 1, wherein said aminoacyl-tRNA synthetase is methionyl tRNA synthetase.

7. The method of claim 1, wherein said desired amino acid analogue comprises side chain functionalities different from its corresponding natural amino acid.

8. The method of claim 1, wherein the selected amino acid is methionine; and the desired amino acid analogue is selected from the group consisting of homoallyglycine, homoproparglycine, norvaline, norleucine, cis-crotylglycine, trans-crotylglycine, 2-aminoheptanoic acid, 2-butynylglycine, allylglycine, azidoalanine and azidohomoalanine.

9. The method of claim 4 wherein said auxotroph is from an organism which is selected from the group consisting of bacterial, yeast, mammalian, insect, and plant.

10. The method of claim 7, wherein said amino acid analogue is a hydrophobic amino acid analogue.

11. The method of claim 10, wherein the hydrophobic amino acid analogue is selected from the group consisting of fluorinated, electroactive, and unsaturated amino acids.

* * * * *

SEQUENCE LISTING

<160> NUMBER OF SEQ ID NOS: 2

<210> SEQ ID NO 1
<211> LENGTH: 6501
<212> TYPE: DNA
<213> ORGANISM: Artificial Sequence
<220> FEATURE:
<223> OTHER INFORMATION: Description of Artificial Sequence: pQEI5-MRS

<400> SEQUENCE: 1

| | | | | | |
|---|---|---|---|---|---|
| ctcgagaaat | cataaaaaat | ttatttgctt | tgtgagcgga | taacaattat | aatagattca | 60 |
| attgtgagcg | gataacaatt | tcacacagaa | ttcattaaag | aggagaaatt | aactatgaga | 120 |
| ggatcgcatc | accatcacca | tcacggatcc | ggcatcatgg | ttcgaccatt | gaactcgatc | 180 |
| gtcgccgtgt | cccaaaatat | ggggattggc | aagaacggag | acctaccctg | gcctccgctc | 240 |
| aggaacgagt | tcaagtactt | ccaaagaatg | accacaacct | cttcagtgga | aggtaaacag | 300 |
| aatctggtga | ttatgggtag | gaaaacctgg | ttctccattc | ctgagaagaa | tcgacccttta | 360 |
| aaggacagaa | ttaatatagt | tctcagtaga | gaactcaaag | aaccaccacg | aggagctcat | 420 |
| tttcttgcca | aaagtttgga | tgatgcctta | agacttattg | aacaaccgga | attggcaagt | 480 |
| aaagtagaca | tggtttggat | agtcggaggc | agttctgttt | accaggaagc | catgaatcaa | 540 |
| ccaggccacc | ttagactctt | tgtgacaagg | atcatgcagg | aatttgaaag | tgacacgttt | 600 |
| ttcccagaaa | ttgatttggg | gaaatataaa | cttctcccag | aatacccagg | cgtcctctct | 660 |
| gaggtccagg | aggaaaaagg | catcaagtat | aagtttgaag | tctacgagaa | gaaaggttgg | 720 |
| aagatcttaa | gcttaattag | ctgagcttgg | actcctgttg | atagatccag | taatgacctc | 780 |
| agaactccat | ctggatttgt | tcagaacgct | cggttgccgc | cgggcgtttt | ttattggtga | 840 |
| gaatccaagc | tagctctaga | gacgtccggc | cggagctcca | ccgcggtggc | ggccgctcta | 900 |
| gagtcactta | cttaacattt | tcccatttgg | tactatctaa | cccctttttca | ctattaagaa | 960 |
| gtaatgccta | ctatgactca | agtcgcgaag | aaaattctgg | tgacgtgcgc | actgccgtac | 1020 |
| gctaacggct | caatccacct | cggccatatg | ctggagcaca | tccaggctga | tgtctgggtc | 1080 |
| cgttaccagc | gaatgcgcgg | ccacgaggtc | aacttcatct | gcgccgacga | tgcccacggt | 1140 |
| acaccgatca | tgctgaaagc | tcagcagctt | ggtatcaccc | cggagcagat | gattggcgaa | 1200 |
| atgagtcagg | agcatcagac | tgatttcgca | ggctttaaca | tcagctatga | caactatcac | 1260 |
| tcgacgcaca | gcgaagagaa | ccgccagttg | tcagaactta | tctactctcg | cctgaaagaa | 1320 |
| aacggttta | ttaaaaaccg | caccatctct | cagctgtacg | atccggaaaa | aggcatgttc | 1380 |
| ctgccggacc | gttttgtgaa | aggcacctgc | ccgaaatgta | atccccgga | tcaatacggc | 1440 |
| gataactgcg | aagtctgcgg | cgcgacctac | agcccgactg | aactgatcga | gccgaaatcg | 1500 |
| gtggtttctg | gcgctacgcc | ggtaatgcgt | gattctgaac | acttcttctt | tgatctgccc | 1560 |
| tctttcagcg | aaatgttgca | ggcatggacc | cgcagcggtg | cgttgcagga | gcaggtggca | 1620 |
| aataaaatgc | aggagtggtt | tgaatctggc | ctgcaacagt | gggatatctc | ccgcgacgcc | 1680 |
| ccttacttcg | gttttgaaat | tccgaacgcg | ccgggcaaat | atttctacgt | ctggctggac | 1740 |
| gcaccgattg | gctacatggg | ttcttttcaag | aatctgtgcg | acaagcgcgg | cgacagcgta | 1800 |
| agcttcgatg | aatactggaa | gaaagactcc | accgccgagc | tgtaccactt | catcggtaaa | 1860 |
| gatattgttt | acttccacag | cctgttctgg | cctgccatgc | tggaaggcag | caacttccgc | 1920 |
| aagccgtcca | acctgtttgt | tcatggctat | gtgacggtga | acggcgcaaa | gatgtccaag | 1980 |

```
tctcgcggca cctttattaa agccagcacc tggctgaatc attttgacgc agacagcctg   2040
cgttactact acactgcgaa actctcttcg cgcattgatg atatcgatct caacctggaa   2100
gatttcgttc agcgtgtgaa tgccgatatc gttaacaaag tggttaacct ggcctcccgt   2160
aatgcgggct ttatcaacaa gcgttttgac ggcgtgctgg caagcgaact ggctgacccg   2220
cagttgtaca aaaccttcac tgatgccgct gaagtgattg gtgaagcgtg ggaaagccgt   2280
gaatttggta agccgtgcg cgaaatcatg gcgctggctg atctggctaa ccgctatgtc   2340
gatgaacagg ctccgtgggt ggtggcgaaa caggaaggcc gcgatgccga cctgcaggca   2400
atttgctcaa tgggcatcaa cctgttccgc gtgctgatga cttacctgaa gccggtactg   2460
ccgaaactga ccgagcgtgc agaagcattc ctcaatacgg aactgacctg gatggtatc    2520 cagcaaccgc tgctgggcca aaagtgaat ccgttcaagg cgctgtataa ccgcatcgat    2580
atgaggcagg ttgaagcact ggtggaagcc tctaaatgag aagtaaaagc cgctgccgcg   2640
ccggtaactg gcccgctggc agatgatccg attcaggaaa ccatcacctt tgacgacttc   2700
gctaaagttg acctgcgcgt ggcgctgatt gaaaacgcag agtttgttga aggttctgac   2760
aaactgctgc gcctgacgct ggatctcggc ggtgaaaaac gcaatgtctt ctccggtatt   2820
cgttctgctt acccggatcc gcaggcactg attggtcgtc acaccattat ggtggctaac   2880
ctggcaccac gtaaaatgcg cttcggtatc tctgaaggca tggtgatggc tgccggtcct   2940
ggcgggaaag atattttcct gctaagcccg gatgccggtg ctaaaccggg tcatcaggtg   3000
aaataatccc ccttcaaggc gctgcatcga cagccttttg ctttataaat tcctaaagtt   3060
gttttcttgc gattttgtct ctctctaacc cgcataaata ctggtagcat ctgcattcaa   3120
ctggataaaa ttacagggat gcagaatgag acactttatc tatcaggacg aaaaatcaca   3180
taaattcagg gcagttgagc aacagggaaa cgagttgcat atcagttggg gaaaagttgg   3240
caccaaaggc aaagccagat aaaaagtttt tcagatgctg cggcagcggc aaaagcggag   3300
cccgacctcg aggggggggcc cggtacccgg ccggacgtct ctagagctag cttggcgaga   3360
ttttcaggag ctaaggaagc taaaatggag aaaaaaatca ctggatatac caccgttgat   3420
atatcccaat ggcatcgtaa agaacatttt gaggcatttc agtcagttgc tcaatgtacc   3480
tataaccaga ccgttcagct ggatattacg gcctttttaa agaccgtaaa gaaaaataag   3540
cacaagtttt atccggcctt tattcacatt cttgcccgcc tgatgaatgc tcatccggaa   3600
tttcgtatgg caatgaaaga cggtgagctg gtgatatggg atagtgttca cccttgttac   3660
accgttttcc atgagcaaac tgaaacgttt tcatcgctct ggagtgaata ccacgacgat   3720
ttccggcagt ttctacacat atattcgcaa gatgtggcgt gttacggtga aaacctggcc   3780
tatttcccta aagggtttat tgagaatatg ttttttcgtct cagccaatcc ctgggtgagt   3840
ttcaccagtt ttgatttaaa cgtggccaat atggacaact tcttcgcccc cgttttcacc   3900
atgggcaaat attatacgca aggcgacaag gtgctgatgc cgctggcgat tcaggttcat   3960
catgccgtct gtgatggctt ccatgtcggc agaatgctta atgaattaca acagtactgc   4020
gatgagtggc agggcggggc gtaattttt taaggcagtt attggtgccc ttaaacgcct   4080
ggggtaatga ctctctagct tgaggcatca aataaaacga aaggctcagt cgaaagactg   4140
ggcctttcgt tttatctgtt gtttgtcggt gaacgctctc ctgagtagga caaatccgcc   4200
gctctagagc tgcctcgcgc gtttcggtga tgacggtgaa aacctctgac acatgcagct   4260
cccggagacg gtcacagctt gtctgtaagc ggatgccggg agcagacaag cccgtcaggg   4320
```

-continued

```
cgcgtcagcg ggtgttggcg ggtgtcgggg cgcagccatg acccagtcac gtagcgatag    4380
cggagtgtat actggcttaa ctatgcgcca tcagagcaga ttgtactgag agtgcaccat    4440
atgcggtgtg aaataccgca cagatgcgta aggagaaaat accgcatcag gcgctcttcc    4500
gcttcctcgc tcactgactc gctgcgctcg tctgtcggc tgcggcgagc ggtatcagct     4560
cactcaaagg cggtaatacg gttatccaca gaatcagggg ataacgcagg aaagaacatg    4620
tgagcaaaag gccagcaaaa ggccaggaac cgtaaaaagg ccgcgttgct ggcgtttttc    4680
cataggctcc gcccccctga cgagcatcac aaaaatcgac gctcaagtca gaggtggcga    4740
aacccgacag gactataaag ataccaggcg tttccccctg gaagctccct cgtgcgctct    4800
cctgttccga ccctgccgct taccggatac ctgtccgcct ttctcccttc gggaagcgtg    4860
gcgctttctc aatgctcacg ctgtaggtat ctcagttcgg tgtaggtcgt tcgctccaag    4920
ctgggctgtg tgcacgaacc ccccgttcag cccgaccgct gcgccttatc cggtaactat    4980
cgtcttgagt ccaacccggt aagacacgac ttatcgccac tggcagcagc cactggtaac    5040
aggattagca gagcgaggta tgtaggcggt gctacagagt tcttgaagtg gtggcctaac    5100
tacggctaca ctagaaggac agtatttggt atctgcgctc tgctgaagcc agttaccttc    5160
ggaaaagag ttggtagctc ttgatccggc aaacaaacca ccgctggtag cggtggtttt     5220
tttgtttgca agcagcagat tacgcgcaga aaaaaaggat ctcaagaaga tcctttgatc    5280
ttttctacgg ggtctgacgc tcagtggaac gaaaactcac gttaagggat tttggtcatg    5340
agattatcaa aaaggatctt cacctagatc cttttaaatt aaaaatgaag ttttaaatca    5400
atctaaagta tatatgagta aacttggtct gacagttacc aatgcttaat cagtgaggca    5460
cctatctcag cgatctgtct atttcgttca tccatagctg cctgactccc cgtcgtgtag    5520
ataactacga tacgggaggg cttaccatct ggccccagtg ctgcaatgat accgcgagac    5580
ccacgctcac cggctccaga tttatcagca ataaaccagc cagccggaag ggccgagcgc    5640
agaagtggtc ctgcaacttt atccgcctcc atccagtcta ttaattgttg ccgggaagct    5700
agagtaagta gttcgccagt taatagtttg cgcaacgttg ttgccattgc tacaggcatc    5760
gtggtgtcac gctcgtcgtt tggtatggct tcattcagct ccggttccca acgatcaagg    5820
cgagttacat gatcccccat gttgtgcaaa aaagcggtta gctccttcgg tcctccgatc    5880
gttgtcagaa gtaagttggc cgcagtgtta tcactcatgg ttatggcagc actgcataat    5940
tctcttactg tcatgccatc cgtaagatgc ttttctgtga ctggtgagta ctcaaccaag    6000
tcattctgag aatagtgtat gcggcgaccg agttgctctt gcccggcgtc aatacgggat    6060
aataccgcgc cacatagcag aactttaaaa gtgctcatca ttggaaaacg ttcttcgggg    6120
cgaaaactct caaggatctt accgctgttg agatccagtt cgatgtaacc cactcgtgca    6180
cccaactgat cttcagcatc ttttactttc accagcgttt ctgggtgagc aaaaacagga    6240
aggcaaaatg ccgcaaaaaa gggaataagg gcgacacgga aatgttgaat actcatactc    6300
ttcctttttc aatattattg aagcatttat cagggttatt gtctcatgag cggatacata    6360
tttgaatgta tttagaaaaa taaacaaata ggggttccgc gcacatttcc ccgaaaagtg    6420
ccacctgacg tctaagaaac cattattatc atgacattaa cctataaaaa taggcgtatc    6480
acgaggccct ttcgtcttca c                                              6501
```

<210> SEQ ID NO 2
<211> LENGTH: 6501
<212> TYPE: DNA
<213> ORGANISM: Artificial Sequence
<220> FEATURE:
<223> OTHER INFORMATION: Description of Artificial Sequence: pQEI5-W305F

<400> SEQUENCE: 2

| | | | | | |
|---|---|---|---|---|---|
| ctcgagaaat | cataaaaaat | ttatttgctt | tgtgagcgga | taacaattat | aatagattca | 60 |
| attgtgagcg | gataacaatt | tcacacagaa | ttcattaaag | aggagaaatt | aactatgaga | 120 |
| ggatcgcatc | accatcacca | tcacggatcc | ggcatcatgg | ttcgaccatt | gaactcgatc | 180 |
| gtcgccgtgt | cccaaaatat | ggggattggc | aagaacggag | acctaccctg | gcctccgctc | 240 |
| aggaacgagt | tcaagtactt | ccaaagaatg | accacaacct | cttcagtgga | aggtaaacag | 300 |
| aatctggtga | ttatgggtag | gaaaacctgg | ttctccattc | ctgagaagaa | tcgacccttta | 360 |
| aaggacagaa | ttaatatagt | tctcagtaga | gaactcaaag | aaccaccacg | aggagctcat | 420 |
| tttcttgcca | aaagtttgga | tgatgcctta | agacttattg | aacaaccgga | attggcaagt | 480 |
| aaagtagaca | tggtttggat | agtcggaggc | agttctgttt | accaggaagc | catgaatcaa | 540 |
| ccaggccacc | ttagactctt | tgtgacaagg | atcatgcagg | aatttgaaag | tgacacgttt | 600 |
| ttcccagaaa | ttgatttggg | gaaatataaa | cttctcccag | aatacccagg | cgtcctctct | 660 |
| gaggtccagg | aggaaaaagg | catcaagtat | aagtttgaag | tctacgagaa | gaaaggttgg | 720 |
| aagatcttaa | gcttaattag | ctgagcttgg | actcctgttg | atagatccag | taatgacctc | 780 |
| agaactccat | ctggatttgt | tcagaacgct | cggttgccgc | cgggcgtttt | ttattggtga | 840 |
| gaatccaagc | tagctctaga | gacgtccggc | cggagctcca | ccgcggtggc | ggccgctcta | 900 |
| gagtcactta | cttaacattt | tcccatttgg | tactatctaa | cccctttca | ctattaagaa | 960 |
| gtaatgccta | ctatgactca | agtcgcgaag | aaaattctgg | tgacgtgcgc | actgccgtac | 1020 |
| gctaacggct | caatccacct | cggccatatg | ctggagcaca | tccaggctga | tgtctgggtc | 1080 |
| cgttaccagc | gaatgcgcgg | ccacgaggtc | aacttcatct | gcgccgacga | tgcccacggt | 1140 |
| acaccgatca | tgctgaaagc | tcagcagctt | ggtatcaccc | cggagcagat | gattggcgaa | 1200 |
| atgagtcagg | agcatcagac | tgatttcgca | ggctttaaca | tcagctatga | caactatcac | 1260 |
| tcgacgcaca | gcgaagagaa | ccgccagttg | tcagaactta | tctactctcg | cctgaaagaa | 1320 |
| aacggtttta | ttaaaaaccg | caccatctct | cagctgtacg | atccggaaaa | aggcatgttc | 1380 |
| ctgccggacc | gttttgtgaa | aggcacctgc | ccgaaatgta | atccccggga | tcaatacggc | 1440 |
| gataactgcg | aagtctgcgg | cgcgacctac | agcccgactg | aactgatcga | gccgaaatcg | 1500 |
| gtggtttctg | gcgctacgcc | ggtaatgcgt | gattctgaac | acttcttctt | tgatctgccc | 1560 |
| tctttcagcg | aaatgttgca | ggcatggacc | cgcagcggtg | cgttgcagga | gcaggtggca | 1620 |
| aataaaatgc | aggagtggtt | tgaatctggc | ctgcaacagt | gggatatctc | ccgcgacgcc | 1680 |
| ccttacttcg | gttttgaaat | tccgaacgcg | ccgggcaaat | atttctacgt | ctggctggac | 1740 |
| gcaccgattg | gctacatggg | ttcttttcaag | aatctgtgcg | acaagcgcgg | cgacagcgta | 1800 |
| agcttcgatg | aatactggaa | gaaagactcc | accgccgagc | tgtaccactt | catcggtaaa | 1860 |
| gatattgttt | acttccacag | cctgttcttc | cctgccatgc | tggaaggcag | caacttccgc | 1920 |
| aagccgtcca | acctgtttgt | tcatggctat | gtgacggtga | acggcgcaaa | gatgtccaag | 1980 |
| tctcgcggca | cctttattaa | agccagcacc | tggctgaatc | attttgacgc | agacagcctg | 2040 |
| cgttactact | acactgcgaa | actctcttcg | cgcattgatg | atatcgatct | caacctggaa | 2100 |
| gatttcgttc | agcgtgtgaa | tgccgatatc | gttaacaaag | tggttaacct | ggcctcccgt | 2160 |
| aatgcgggct | ttatcaacaa | gcgttttgac | ggcgtgctgg | caagcgaact | ggctgacccg | 2220 |

-continued

```
cagttgtaca aaaccttcac tgatgccgct gaagtgattg gtgaagcgtg ggaaagccgt      2280
gaatttggta agccgtgcg cgaaatcatg gcgctggctg atctggctaa ccgctatgtc      2340
gatgaacagg ctccgtgggt ggtggcgaaa caggaaggcc gcgatgccga cctgcaggca      2400
atttgctcaa tgggcatcaa cctgttccgc gtgctgatga cttacctgaa gccggtactg      2460
ccgaaactga ccgagcgtgc agaagcattc ctcaatacgg aactgacctg ggatggtatc      2520
cagcaaccgc tgctgggcca caaagtgaat ccgttcaagg cgctgtataa ccgcatcgat      2580
atgaggcagg ttgaagcact ggtggaagcc tctaaatgag aagtaaaagc cgctgccgcg      2640
ccggtaactg gcccgctggc agatgatccg attcaggaaa ccatcacctt tgacgacttc      2700
gctaaagttg acctgcgcgt ggcgctgatt gaaaacgcag agtttgttga aggttctgac      2760
aaactgctgc gcctgacgct ggatctcggc ggtgaaaaac gcaatgtctt ctccggtatt      2820
cgttctgctt acccggatcc gcaggcactg attggtcgtc acaccattat ggtggctaac      2880
ctggcaccac gtaaaatgcg cttcggtatc tctgaaggca tggtgatggc tgccggtcct      2940
ggcgggaaag atattttcct gctaagcccg gatgccggtg ctaaaccggg tcatcaggtg      3000
aaataatccc ccttcaaggc gctgcatcga cagccttttg ctttataaat tcctaaagtt      3060
gttttcttgc gattttgtct ctctctaacc cgcataaata ctggtagcat ctgcattcaa      3120
ctggataaaa ttacagggat gcagaatgag acactttatc tatcaggacg aaaaatcaca      3180
taaattcagg gcagttgagc aacagggaaa cgagttgcat atcagttggg gaaaagttgg      3240
caccaaaggc aaagccagat aaaaagtttt tcagatgctg cggcagcggc aaaagcggag      3300
cccgacctcg aggggggggcc cggtacccgg ccggacgtct ctagagctag cttggcgaga      3360
ttttcaggag ctaaggaagc taaaatggag aaaaaaatca ctggatatac caccgttgat      3420
atatcccaat ggcatcgtaa agaacatttt gaggcatttc agtcagttgc tcaatgtacc      3480
tataaccaga ccgttcagct ggatattacg gcctttttaa agaccgtaaa gaaaaataag      3540
cacaagtttt atccggcctt tattcacatt cttgcccgcc tgatgaatgc tcatccggaa      3600
tttcgtatgg caatgaaaga cggtgagctg gtgatatggg atagtgttca cccttgttac      3660
accgttttcc atgagcaaac tgaaacgttt tcatcgctct ggagtgaata ccacgacgat      3720
ttccggcagt ttctacacat atattcgcaa gatgtggcgt gttacggtga aaacctggcc      3780
tatttcccta aagggtttat tgagaatatg ttttttcgtct cagccaatcc ctgggtgagt      3840
ttcaccagtt ttgatttaaa cgtggccaat atggacaact tcttcgcccc cgttttcacc      3900
atgggcaaat attatacgca aggcgacaag gtgctgatgc cgctggcgat tcaggttcat      3960
catgccgtct gtgatggctt ccatgtcggc agaatgctta atgaattaca acagtactgc      4020
gatgagtggc agggcgggc gtaatttttt taaggcagtt attggtgccc ttaaacgcct      4080
ggggtaatga ctctctagct tgaggcatca aataaaacga aaggctcagt cgaaagactg      4140
ggcctttcgt tttatctgtt gtttgtcggt gaacgctctc ctgagtagga caaatccgcc      4200
gctctagagc tgcctcgcgc gtttcggtga tgacggtgaa aacctctgac acatgcagct      4260
cccggagacg gtcacagctt gtctgtaagc ggatgccggg agcagacaag cccgtcaggg      4320
cgcgtcagcg ggtgttggcg ggtgtcgggg cgcagccatg acccagtcac gtagcgatag      4380
cggagtgtat actggcttaa ctatgcggca tcagagcaga ttgtactgag agtgcaccat      4440
atgcggtgtg aaataccgca cagatgcgta aggagaaaat accgcatcag gcgctcttcc      4500
gcttcctcgc tcactgactc gctgcgctcg gtctgtcggc tgcggcgagc ggtatcagct      4560
```

-continued

```
cactcaaagg cggtaatacg gttatccaca gaatcagggg ataacgcagg aaagaacatg    4620
tgagcaaaag gccagcaaaa ggccaggaac cgtaaaaagg ccgcgttgct ggcgttttc     4680
cataggctcc gcccccctga cgagcatcac aaaaatcgac gctcaagtca gaggtggcga    4740
aacccgacag gactataaag ataccaggcg tttccccctg gaagctccct cgtgcgctct    4800
cctgttccga ccctgccgct taccggatac ctgtccgcct ttctcccttc gggaagcgtg    4860
gcgctttctc aatgctcacg ctgtaggtat ctcagttcgg tgtaggtcgt tcgctccaag    4920
ctgggctgtg tgcacgaacc ccccgttcag cccgaccgct gcgccttatc cggtaactat    4980
cgtcttgagt ccaacccggt aagacacgac ttatcgccac tggcagcagc cactggtaac    5040
aggattagca gagcgaggta tgtaggcggt gctacagagt tcttgaagtg gtggcctaac    5100
tacggctaca ctagaaggac agtatttggt atctgcgctc tgctgaagcc agttaccttc    5160
ggaaaaagag ttggtagctc ttgatccggc aaacaaacca ccgctggtag cggtggtttt    5220
tttgtttgca agcagcagat tacgcgcaga aaaaaggat ctcaagaaga tcctttgatc     5280
ttttctacgg ggtctgacgc tcagtggaac gaaaactcac gttaagggat tttggtcatg    5340
agattatcaa aaaggatctt cacctagatc cttttaaatt aaaaatgaag ttttaaatca    5400
atctaaagta tatatgagta aacttggtct gacagttacc aatgcttaat cagtgaggca    5460
cctatctcag cgatctgtct atttcgttca tccatagctg cctgactccc cgtcgtgtag    5520
ataactacga tacgggaggg cttaccatct ggccccagtg ctgcaatgat accgcgagac    5580
ccacgctcac cggctccaga tttatcagca ataaccagc cagccggaag ggccgagcgc     5640
agaagtggtc ctgcaacttt atccgcctcc atccagtcta ttaattgttg ccgggaagct    5700
agagtaagta gttcgccagt taatagtttg cgcaacgttg ttgccattgc tacaggcatc    5760
gtggtgtcac gctcgtcgtt tggtatggct tcattcagct ccggttccca acgatcaagg    5820
cgagttacat gatcccccat gttgtgcaaa aaagcggtta gctccttcgg tcctccgatc    5880
gttgtcagaa gtaagttggc cgcagtgtta tcactcatgg ttatggcagc actgcataat    5940
tctcttactg tcatgccatc cgtaagatgc ttttctgtga ctggtgagta ctcaaccaag    6000
tcattctgag aatagtgtat gcggcgaccg agttgctctt gcccggcgtc aatacgggat    6060
aataccgcgc cacatagcag aactttaaaa gtgctcatca ttggaaaacg ttcttcgggg    6120
cgaaaactct caaggatctt accgctgttg agatccagtt cgatgtaacc cactcgtgca    6180
cccaactgat cttcagcatc ttttactttc accagcgttt ctgggtgagc aaaaacagga    6240
aggcaaaatg ccgcaaaaaa gggaataagg gcgacacgga aatgttgaat actcatactc    6300
ttcctttttc aatattattg aagcatttat cagggttatt gtctcatgag cggatacata    6360
tttgaatgta tttagaaaaa taaacaaata ggggttccgc gcacatttcc ccgaaaagtg    6420
ccacctgacg tctaagaaac cattattatc atgacattaa cctataaaaa taggcgtatc    6480
acgaggccct ttcgtcttca c                                              6501
```